US011638792B2

(12) United States Patent
Hyde et al.

(10) Patent No.: US 11,638,792 B2
(45) Date of Patent: May 2, 2023

(54) COLLAPSIBLE, DISPOSABLE MEDICATION INHALATION SPACER AND METHOD

(71) Applicant: THAYER MEDICAL CORPORATION, Tucson, AZ (US)

(72) Inventors: Joel Hyde, Tucson, AZ (US); James Strickland, Tucson, AZ (US); Jennifer Johnson, Tucson, AZ (US)

(73) Assignee: THAYER MEDICAL CORPORATION, Tucson, AZ (US)

( * ) Notice: Subject to any disclaimer, the term of this patent is extended or adjusted under 35 U.S.C. 154(b) by 0 days.

(21) Appl. No.: 17/599,401

(22) PCT Filed: Mar. 30, 2020

(86) PCT No.: PCT/US2020/025714
§ 371 (c)(1),
(2) Date: Sep. 28, 2021

(87) PCT Pub. No.: WO2020/198736
PCT Pub. Date: Oct. 1, 2020

(65) Prior Publication Data
US 2022/0211957 A1 Jul. 7, 2022

Related U.S. Application Data

(63) Continuation-in-part of application No. 16/777,529, filed on Jan. 30, 2020, now Pat. No. 11,383,051, and
(Continued)

(51) Int. Cl.
*A61M 15/00* (2006.01)
*F16F 1/36* (2006.01)

(52) U.S. Cl.
CPC ...... *A61M 15/0021* (2014.02); *A61M 15/009* (2013.01); *A61M 15/0013* (2014.02);
(Continued)

(58) Field of Classification Search
CPC .......... A61M 15/0021; A61M 15/0013; A61M 15/0018; A61M 15/0086; A61M 15/0088;
(Continued)

(56) References Cited

U.S. PATENT DOCUMENTS

| 4,951,661 A | 8/1990 | Sladek | 128/202.27 |
| 4,953,545 A | 9/1990 | McCarty | 128/200.23 |

(Continued)

FOREIGN PATENT DOCUMENTS

| CA | 2212642 | 8/1996 | ............. A63B 23/18 |
| CA | 2223518 | 12/1996 | ............. A63B 23/18 |

(Continued)

OTHER PUBLICATIONS

Australian Certificate of Registration of Trademark, No. 1751570 for LiteAire, filed Feb. 10, 2016 (1 pg).
(Continued)

*Primary Examiner* — Elliot S Ruddie
(74) *Attorney, Agent, or Firm* — Hayes Soloway P.C.

(57) ABSTRACT

A medication inhalation apparatus preferably formed of a single, unitary sheet of stock, includes an outer housing, movable between collapsed and expanded states, encompassing a first volume. An inner housing within the outer housing encompasses an inner or second volume. An inhaler opening to the first volume is within a wall of the outer housing at a first location. A mouth opening to the inner volume is within a wall of the outer housing and the inner housing at a second location. A one-way inhalation valve connecting the first volume and the inner volume is within a wall of the inner housing. A one-way exhalation valve connecting the inner volume and the exterior of the outer housing is within a wall of the outer housing and inner housing at a third location. The valve preferably includes an elongated spring body formed of a semi-pliant material with
(Continued)

a strength and rigidity providing limited flexibility. A first separation is perpendicular to the elongate axis of the spring body, and extends from a first edge of the spring body across at least a portion of a width of the spring body. A second separation perpendicular to the elongate axis of the spring body extends from a second edge of the spring body across at least a portion of the width of the spring body.

17 Claims, 28 Drawing Sheets

Related U.S. Application Data a continuation-in-part of application No. 16/368,585, filed on Mar. 28, 2019, now Pat. No. 10,589,040, and a continuation-in-part of application No. 16/368,581, filed on Mar. 28, 2019, now Pat. No. 11,266,797.

(52) U.S. Cl.
 CPC .... *A61M 15/0018* (2014.02); *A61M 15/0088* (2014.02); *F16F 1/3605* (2013.01); *A61M 2207/00* (2013.01); *F16F 2234/06* (2013.01)

(58) Field of Classification Search
 CPC ............. A61M 15/009; A61M 2207/00; F16F 1/3605; F16F 2234/06
 See application file for complete search history.

(56) References Cited

U.S. PATENT DOCUMENTS

| | | | |
|---|---|---|---|
| D335,175 S | 4/1993 | Sladek | D24/110 |
| 5,427,089 A | 6/1995 | Kraemer | A61M 11/00 |
| D362,500 S | 9/1995 | Cook et al. | D24/110 |
| 5,474,058 A | 12/1995 | Lix | 128/200.18 |
| 6,014,972 A | 1/2000 | Sladek | 128/203.12 |
| 6,039,042 A | 3/2000 | Sladek | 128/200.23 |
| 6,098,619 A | 8/2000 | Britto | A61M 11/003 |
| 6,202,643 B1 | 3/2001 | Sladek | 128/200.23 |
| 6,435,176 B1 | 8/2002 | Berg et al. | 128/200.23 |
| 6,463,929 B1 | 10/2002 | Scheuch | A61M 15/00 |
| 6,550,473 B1 | 4/2003 | Sladek | 128/200.23 |
| 6,679,252 B2 | 1/2004 | Sladek | 128/200.23 |
| 7,347,203 B2 | 3/2008 | Marler et al. | 128/201.13 |
| 7,360,537 B2 | 4/2008 | Snyder et al. | 128/200.23 |
| 7,921,846 B1 | 4/2011 | Marler et al. | 128/205.24 |
| 2002/0129814 A1* | 9/2002 | Sladek | A61M 15/0086 |
| | | | 128/200.23 |
| 2004/0267185 A1 | 12/2004 | Weaver et al. | A61M 37/00 |
| 2008/0210225 A1 | 9/2008 | Geiger | A61M 11/00 |
| 2009/0032019 A1* | 2/2009 | Green | A61M 15/0086 |
| | | | 128/203.29 |
| 2010/0163045 A1 | 7/2010 | Powell | A61M 11/00 |
| 2013/0276781 A1 | 10/2013 | Steelman | |
| 2016/0045686 A1 | 2/2016 | Jaroslavsky | A61M 15/0088 |
| 2019/0151578 A1 | 5/2019 | Dennis | A61M 15/0088 |
| 2019/0231994 A1 | 8/2019 | Jaroslavsky | A61M 15/0086 |
| 2019/0358415 A1 | 11/2019 | Taghavi | A61M 15/0021 |
| 2020/0282158 A1 | 9/2020 | Friel | A61M 15/0096 |

FOREIGN PATENT DOCUMENTS

| | | | |
|---|---|---|---|
| CN | 107243102 | 10/2017 | A61M 15/00 |
| EP | 1204437 | 2/2005 | A61M 11/04 |
| WO | WO 96/3 7249 | 11/1996 | A61M 15/00 |
| WO | WO0105458 | 1/2001 | A61M 11/04 |
| WO | WO2015111015 | 7/2015 | B31D 1/02 |
| WO | WO2017205907 | 12/2017 | A61M 15/00 |
| WO | WO2019007968 | 1/2019 | A61M 15/00 |

OTHER PUBLICATIONS

LiteAire® sales literature downloaded from http://thayermedical.com on Apr. 18, 2019 (20 pgs).
Notice of Allowance issued in U.S. Appl. No. 16/368,585, dated Nov. 14, 2019 (9 pgs).
Office Action issued in U.S. Appl. No. 16/368,585, dated Jul. 31, 2019 (16 pgs).
Office Action issued in U.S. Appl. No. 16/368,581, dated Apr. 19, 2021 (10 pgs).
International Search Report and Written Opinion issued in PCT International Patent Application Serial No. PCT/US20/25714, dated Aug. 12, 2020 (14 pages).
International Preliminary Report on Patentability issued in PCT International Patent Application Serial No. PCT/US20/25714, dated Sep. 28, 2021 (10 pages).
Invitation to Pay Additional Fees issued in related PCT International Patent Application Serial No. PCT/US20/25714, dated Jun. 17, 2020 (2 pages).
Office Action issued in U.S. Appl. No. 16/777,529, dated Dec. 6, 2021 (14 pgs).
Notice of Allowance issued in U.S. Appl. No. 16/368,581, dated Nov. 5, 2021 (10 pgs).
U.S. Appl. No. 16/368,585, filed Mar. 28, 2019.
U.S. Appl. No. 16/368,581, filed Mar. 28, 2019, Hyde et al.
U.S. Appl. No. 16/777,529, filed Jan. 30, 2020, Hyde et al.
LiteAire® sales literature, downloaded from http://thayermedical.com. (Wayback Machine) on Sep. 12, 2015 (2 pgs).
Search Report issued in related European Application Serial No. 20776692.4, dated Dec. 5, 2022, 14 pgs.

\* cited by examiner

Method of expanding a medication inhalation apparatus from an initially flat, collapsed state 610 — Providing, in the collapsed state, an outer housing, an inner housing positioned within the outer housing, wherein the outer housing and the inner housing are substantially airtight when expanded, an inhaler opening formed at least partially within a sidewall of the outer housing at a first location, a mouth opening positioned within a sidewall of the outer housing and the inner housing at a second location, a one-way inhalation valve positioned within a sidewall of the inner housing, and a one-way exhalation valve positioned within a sidewall of the outer housing and the inner housing at a third location;

620 — Pressing a pair of opposite sidewall panels on the outer housing;

630 — Manually expanding the outer housing and inner housing to create a first volume encompassed by the outer housing and an inner volume encompassed by the inner housing, wherein the inhaler opening is in fluid communication with the first volume, wherein the mouth opening is in fluid communication with the inner volume, wherein the inhalation valve connects the first volume and the inner volume, wherein the exhalation valve connects the inner volume and the exterior of the outer housing, and wherein gas is flowable from the metered dose inhaler to the first volume, from the first volume to the inner volume, and from the inner volume to the mouth of a patient.

FIG. 6

Method of Expanding a Medication Inhalation Apparatus from an Initially Flat, Collapsed State Providing, in the collapsed state, an outer housing, an inner flap located within the outer housing, wherein the outer housing and the inner flap are substantially airtight when expanded, an inhaler opening formed at least partially within a sidewall of the outer housing at a first location, a mouth opening positioned within a sidewall of the outer housing at a second location, a one-way inhalation valve positioned within a sidewall of the inner flap, and a one-way exhalation valve positioned within a sidewall of the outer housing at a third location;

1310

↓

Pressing a pair of opposite sidewall panels on the outer housing;

1320

↓

Manually expanding the outer housing and inner flap to create a first volume encompassed by the outer housing and a second volume encompassed by the inner flap and the outer housing, wherein the inhaler opening is in fluid communication with the first volume, wherein the mouth opening is in fluid communication with the second volume, wherein the inhalation valve connects the first volume and the second volume, wherein the exhalation valve connects the second volume and the exterior of the outer housing, and wherein gas is flowable from the inhaler to the first volume, from the first volume to the second volume, and from the second volume to the mouth of a patient.

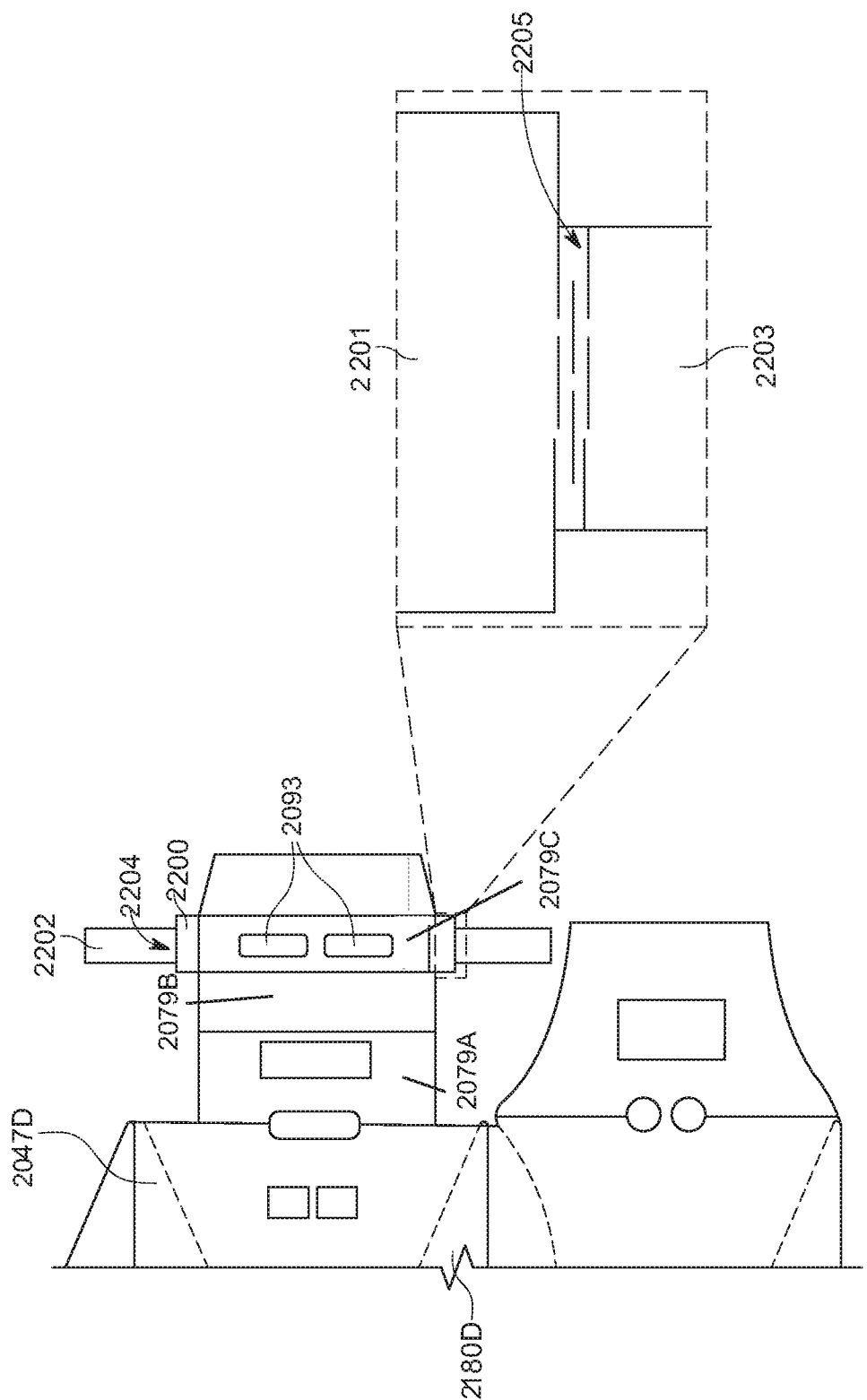

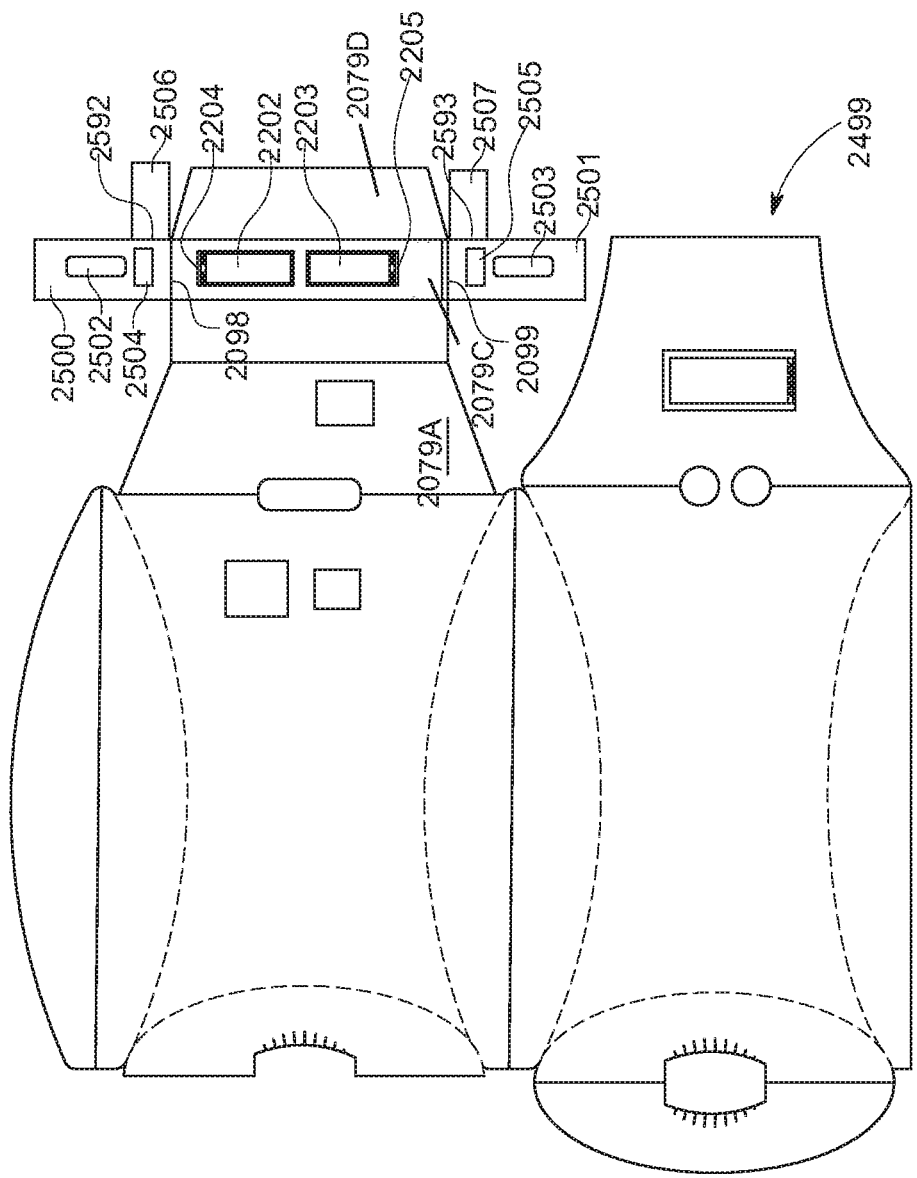

Method of expanding a medication inhalation apparatus from an initially flat, collapsed state

2600

2610 — Providing, in the collapsed state, an outer housing, an inner barrier positioned within the outer housing, an inhaler opening formed at least partially within a sidewall of the outer housing at a first location, a mouth opening positioned within a sidewall of the outer housing at a second location, a one-way inhalation valve positioned within a sidewall of the inner barrier and formed from the inner barrier, and a one-way exhalation valve positioned within a sidewall of the outer housing and the inner housing at a third location, wherein the exhalation valve is formed from the outer housing;

2620 — Manually pressing a pair of opposite sidewall panels on the outer housing towards one another;

2630 — Manually expanding the outer housing and inner barrier to create a first volume encompassed by the outer housing and a second volume delineated by the inner barrier and a mouth opening end of the outer housing, wherein the inhaler opening is in fluid communication with the first volume, wherein the mouth opening is in fluid communication with the second volume, wherein the inhalation valve connects the first volume and the second volume, wherein the exhalation valve connects the and the exterior of the outer housing, and wherein gas is flowable from the metered dose inhaler to the first volume, from the first volume to the second volume and from the second volume to the mouth of a user.

FIG. 23

COLLAPSIBLE, DISPOSABLE MEDICATION INHALATION SPACER AND METHOD

CROSS REFERENCE TO RELATED APPLICATION

This application is a continuation-in-part of co-pending U.S. patent application Ser. No. 16/777,529, filed Jan. 30, 2020, which is a continuation-in-part of co-pending U.S. patent application Ser. No. 16/368,581, filed Mar. 28, 2019. This application also claims priority to U.S. patent application Ser. No. 16/368,585, filed Mar. 28, 2019, the contents of which are incorporated herein by reference.

The present disclosure is generally related to aerosol medication inhalers and more particularly is related to valved chambers for delivering aerosol medication from an MDI canister.

Pressurized Metered Dose Inhaler (MDI) canisters, which have been used since 1956, ordinarily are sold with a dispenser or so-called "boot" that includes an actuator, a nozzle, and a mouthpiece. The user can self-administer the MDI medicament using the boot alone; however, the user must place the mouthpiece of the boot in or near his/her mouth and inhale at essentially the same time the MDI canister is actuated. Some users, like young children and the elderly, find it difficult to coordinate their inhalation with the actuation of the MDI, and even if the user is able to coordinate their inhalation with MDI inhalation, a lot of medicament is deposited into the oropharynx, leading to undesirable side-effects, such as hoarseness or thrush when using corticosteroids.

At first, "Spacers" were created to address the undesirable oropharyngeal deposition; however, these devices do not address the need for coordinated breathing technique. Medical device manufacturers have since created valved holding chambers (VHCs) to address both issues. To combat oropharyngeal deposition, VHCs (like spacers) have a chamber that holds the aerosol plume. This chamber lets the aerosol plume decelerate giving medicament particles the volume needed to aerosolize, and it allows particles that would normally impact on the user's oropharynx to deposit on the inside of the chamber instead. To help alleviate issues with the synchronization of a user's breath with MDI actuation, VHCs also employ a valving system that permits the user's inhalation to draw the medicament from the chamber but re-directs the user's exhalation to be vented out of the mouthpiece of the VHC such that the remaining aerosolized medicament inside the chamber is not blown backwards out of the chamber. This allows patients who can't synchronize their inhalation with MDI actuation to get a significant dose of medicament. It also allows the patient to continue breathing through the VHC throughout the treatment, as the presence of the exhalation valve means there is no need to remove the VHC from the patient's mouth during exhalation. Ultimately, the patient can take in the full dose, while breathing as normally as possible, over multiple breaths if necessary. These devices have now become the recommended as the best-practice accessory to an MDI for patients of all ages.

Many commercially available VHCs, like the Aerochamber Plus® Z-Stat® device available from Monaghan Medical Corporation, and Optichamber® Diamond device available from Philips Respironics, are made of rigid plastic and are substantially cylindrical in shape with a diameter of a couple inches and a length of roughly half a foot, which presents problems to users that need to carry MDI canisters with them all day in case of an emergency asthma attack. Also, in facilities that store large numbers of holding chambers, like hospitals or spirometry testing facilities, the cylindrical shape of most VHCs means that the storage of many VHCs takes up a significant amount of space. Some VHC manufacturers have identified these issues and have partially addressed them by creating collapsible cylindrical VHCs. Many of these collapsible VHCs, however, don't offer a significant advantage to a non-collapsible chamber. For example, the BreatheRite™ collapsible device available from Medline Industries, Inc., shortens the length of the device by a couple inches when collapsed, but the device is still a rigid cylinder with the same diameter. The cylindrical shape still means that the device can't fit comfortably in a user's pocket, as well as meaning that storing large quantities of these devices would still take large amounts of space. The Thayer Medical LiteAire® spacer device collapses to a substantially flat configuration and the dimensions of the VHC allow the device to be carried unobtrusively in a shirt pocket or purse. Also, many LiteAire® spacer devices can be stored in a relatively small area because the packaged devices can be stacked flat on top of each other with very little empty space between devices, which is not possible with cylindrically shaped devices like the BreatheRite™ collapsible device.

Conventional VHCs, like the Aerochamber Plus® Z-Stat® device and Optichamber® Diamond device, cost in the range of $10-20. Some medical applications, like spirometry testing, only require a VHC to be used during a brief testing period by a patient, and this price offers a barrier to the use of a VHC in these settings. While lower cost plastic VHCs have recently been introduced to the market, the recent awareness of the need for environmental sustainability identified another problem with the rigid cylindrical plastic solution. Plastic taxes the environment when disposed of with the frequency required in higher-usage clinical environments like spirometry testing facilities. The LiteAire® offers a solution to this problem as well, with 98% of the device being made from paperboard, the environmental impact upon disposal of the device is substantially reduced.

Another benefit of the LiteAire®'s collapsible device construction is that the device is made of a paperboard which is inherently an antistatic material. The fact that the traditional plastic construction of other VHCs creates a large amount of medicament deposition due to static build up on the inside surface of the VHC has been established by multiple sources, including some patents. Multiple patents have been filed for VHCs or spacers made from antistatic materials. For example, U.S. Pat. Nos. 6,435,176 and 7,360,537, which describe devices made from metal and antistatic plastic, respectively, seek to address this problem. These patents offer solutions to electrostatic deposition but run into some of the same rigidity, cost, and disposal problems mentioned above; and they remain bulky and/or expensive. The LiteAire® collapsible device is able to reduce electrostatic deposition as well as being inexpensive, easily portable and environmentally friendly.

While the current LiteAire® collapsible device offers an inexpensive, disposable, collapsible, and antistatic VHC, the current LiteAire® collapsible device employs plastic valves, which creates certain manufacturing challenges. The valves being a different material than paperboard, require a special form of adhesion. Adhesion could come in the form of solvent bonding, heat bonding, pressure bonding, vibration bonding or an actual adhesive, but regardless of the type of adhesion used, related extra steps and expenses in the manufacturing process are required. The replacement of separate plastic valves with valves made from the same sheet material as the rest of the device simplifies not only the manufacturing of the device, but also simplifies the selection of materials and bonding methods available for manufacturing, considering that bonding a material to itself requires less considerations than bonding two potentially dissimilar materials.

In addition to potential time and expense improvements made to the LiteAire® collapsible device manufacturing process, the replacement of the plastic valves with paperboard means that the disposal of the device in an ecologically friendly way, becomes much faster. This means that the replacement of the plastic valves with valves made of the same paperboard material as the body allows the new LiteAire® collapsible device to be made with 100% renewable resources.

Also, the current iteration of the LiteAire requires the user or caregiver to pinch the sides of the barrier wall during the process of administering the dose of medicament. Anytime a use detail such as this is conveyed in the instructions (also known as a labeling control), if it can affect dose delivery, a design control is preferred. The more intended and reproducible medicament delivery is dependent upon the device design (not on the user), the better.

Further advantage can be gained by achieving near totality of the separation between the chamber holding the aerosolized medicament and the mouthpiece section without the assistance of the user's "pinch". As such, a redesign of the mouthpiece configuration can do away with any holding requirement for the user by disabling any affect the user's exhaled breath might otherwise have on aerosol plume in the chamber.

The present application addresses these above challenges and potential variants in the LiteAire design. These variants would continue to provide the same advantages that the LiteAire already offers over the prior art discussed above and would supplement those advantages.

A redesigned mouthpiece may make use of several elements cut from paperboard for a more cost-effective design. Among these elements may be valves and hinges, which may be applied separately or as monolithic, unitary elements together with the mouthpiece body. A living hinge made from some material as the MDI, i.e., typically paperboard, is known in the art. However, this type of hinge experiences reduced effectiveness after use. Over time, the living hinge may see reduced robustness, i.e., the ability to maintain its original shape and flexibility. Thus, the living hinge may lose its ability to return to a closed position and adequately seal a vent from air flow. Additionally, if the hinge is extended too far, it may lose its ability to return to a closed position. This living hinge may provide a limited spring return; however, it is desirable to provide a more robust spring return for valves in use with the present design.

Accordingly, it is an object of the invention to improve the efficiency of a collapsible/expandable valved chamber device for delivering MDI medications for the like.

It is another object of the invention to reduce the amount of MDI medication lost from a user exhaling into the chamber by preventing a user using a collapsible/expandable valved chamber from inadvertently blowing MDI medication out of the collapsible/expandable valved chamber if the user inadvertently exhales while actuating an MDI canister that introduces the medication into the collapsible/expandable valved chamber, or the user takes in the dose over multiple breaths.

It is another object of the invention to provide an inexpensive, disposable, collapsible valved chamber for delivering MDI medications or other inhaled treatments.

It is another object of the invention to provide an inexpensive, disposable valved chamber which is collapsible to a flat configuration.

It is another object of the invention to provide a valved chamber which is sufficiently inexpensive that it can be used as a discardable diagnostic dosing aid, temporary medication delivery aid, or training aid by means of which a health care provider can demonstrate proper techniques for using a permanent valved chamber.

It is another object of the invention to provide a valved chamber which can pop up from a collapsed configuration to an expanded configuration ready for use.

It is another object of the invention to provide a valved chamber which can pop up from a collapsed configuration to an expanded configuration ready for use and retain the expanded configuration.

It is another object of the invention to provide a valved chamber which can be "popped up" or erected from a collapsed configuration by a user with a minimal amount of effort.

Yet another object of the invention to improve the cost of manufacturing a collapsible/expandable valved chamber device for delivering MDI medications for the like.

The present disclosure can be viewed as providing a medication inhalation apparatus. Briefly described, in architecture, one embodiment of the system, among others, can be implemented as follows. The apparatus includes an outer housing collapsible into a substantially flat configuration and expandable to bound a first volume adapted to receive a plume of medication particles ejected by an MDI inhaler. The apparatus also includes a fully contained inner housing also collapsible into a substantially flat configuration, located within the outer housing and expandable to bound a second volume. A first opening is formed through a wall of the outer housing at a first location, in fluid communication with the first volume, and adapted to accommodate a mouthpiece of an MDI inhaler. Second and third openings are formed through walls of the outer housing and the inner housing adapted to form an user mouth opening in fluid communication with the second volume. A one-way inhalation valve is located within a wall of the inner housing. The inhalation valve connects the first volume and the second volume. A one-way exhalation valve is located within a wall of the outer housing and the inner housing. The exhalation valve connects the inner volume and the exterior of the outer housing. When the apparatus is in an expanded state, gas is flowable from a connected MDI to the first volume, from the first volume to the second volume, and from the inner volume to the mouth of a user.

The present disclosure can also be viewed as providing methods of expanding a medication inhalation apparatus from an initially flat, collapsed state to an expanded state by providing a medication inhalation apparatus as above described, and manually pressing a pair of opposite sidewall panels on the outer housing towards one another, whereby to force the opposite sidewall panels into positions approximately perpendicular to top and bottom panels of the outer housing, and inserting a mouthpiece of an MDI inhaler into an inhaler opening in the outer housing, whereupon the apparatus is ready for use by a patient.

The present disclosure can also be viewed as providing a medication inhalation apparatus. Briefly described, in architecture, one embodiment of the apparatus, among others, can be implemented as follows. The apparatus includes an outer housing, collapsible into a substantially flat configuration and expandable to bound a first volume adapted to receive a plume of medication particles ejected by an MDI inhaler. An inner flap is located within the outer housing and, together with the outer housing, is expandable to bound a second volume within the outer housing. A first opening is formed through a wall of the outer housing at a first location. The first opening is in fluid communication with the first volume, and is adapted to accommodate a mouthpiece of an MDI inhaler. A second opening is formed through a wall of the outer housing at a second location. The second opening is adapted to form a user mouth opening in fluid communication with the second volume. A one-way inhalation valve is located within the inner flap, the inhalation valve connecting the first volume and the second volume. A one-way exhalation valve is located within a wall of the outer housing, the exhalation valve connecting the second volume and an exterior of the outer housing. In an expanded state, gas is flowable from a connected MDI to the first volume, from the first volume to the second volume, and from the second volume to the mouth of a user.

In one aspect of the apparatus, the outer housing and the inner flap are constructed from a single piece of stock. In a particular aspect of the apparatus, the inner flap is connected to the outer housing at a fold. In another particular aspect of the apparatus, the single piece is sheet stock, and the outer housing and the inner flap are formed by folding the sheet. In another particular aspect, the outer housing is connected to the inner flap adjacent the mouth opening side of the sheet stock. In another particular aspect, at least two corners on a bottom panel of the outer housing are receded corners. In another aspect of the apparatus, the outer housing and the inner housing are at least partially constructed from antistatic material.

In another aspect of the apparatus, the inner flap comprises a plurality of panels having a plurality of tension relief lines.

In another aspect of the apparatus, the inner flap is adhesively attached to a bottom panel of the outer housing along at least three adhesive lines.

In another aspect of the apparatus, the inner flap comprises an adhesive panel adjacent to a top panel of the outer housing, wherein the adhesive panel is adhesively attached to the top panel of the outer housing. In a particular aspect, the adhesive panel extends substantially across a width of the inner flap.

The present disclosure can also be viewed as providing a medication inhalation apparatus. Briefly described, in architecture, one embodiment of the apparatus, among others, can be implemented as follows. The apparatus includes an outer housing, collapsible into a substantially flat configuration and expandable to bound a first volume adapted to receive a plume of medication particles ejected by an MDI inhaler. An inner flap is located within the outer housing and is expandable to bound a second volume within the outer housing. An edge panel of the inner flap is adhesively affixed to a portion of the outer housing to secure the second volume. A first opening is formed through a wall of the outer housing at a first location. The first opening is in fluid communication with the first volume and is adapted to accommodate a mouthpiece of an MDI inhaler. A second opening is formed through a wall of the outer housing at a second location and is adapted to form a user mouth opening in fluid communication with the second volume. A one-way inhalation valve is located within a central panel of the inner flap, the inhalation valve connecting the first volume and the second volume. A one-way exhalation valve is located within an outer panel of the inner flap and a wall of the outer housing, the exhalation valve connecting the second volume and an exterior of the outer housing. In an expanded state, gas is flowable from a connected MDI to the first volume, from the first volume to the second volume, and from the second volume to the mouth of a user.

In one aspect of the apparatus, the outer housing and the inner flap are constructed from a single piece of stock. In a particular aspect of the apparatus, the inner flap is connected to the outer housing at a fold. In another particular aspect of the apparatus, the single piece is sheet stock, and the outer housing and the inner flap are formed by folding the sheet. In another particular aspect, the outer housing is connected to the inner flap adjacent the mouth opening side of the sheet stock.

In another aspect of the apparatus, the outer housing and the inner housing are at least partially constructed from antistatic material.

In another aspect of the apparatus, the one-way exhalation valve comprises an exhalation valve located within the inner flap and a valve opening located within a wall of the outer housing.

The present disclosure can also be viewed as providing methods of expanding a medication inhalation apparatus from an initially flat, collapsed state to an expanded state. In this regard, one embodiment of such a method, among others, can be broadly summarized by the following steps: providing, in the collapsed state, an outer housing, an inner flap located within the outer housing, wherein the outer housing and the inner flap are substantially airtight when expanded, an inhaler opening formed at least partially within a sidewall of the outer housing at a first location, a mouth opening positioned within a sidewall of the outer housing at a second location, a one-way inhalation valve positioned within a sidewall of the inner flap, and a one-way exhalation valve positioned within a sidewall of the outer housing at a third location; pressing a pair of opposite sidewall panels on the outer housing; and manually expanding the outer housing and inner flap to create a first volume encompassed by the outer housing and a second volume encompassed by the inner flap and the outer housing, wherein the inhaler opening is in fluid communication with the first volume, wherein the mouth opening is in fluid communication with the second volume, wherein the inhalation valve connects the first volume and the second volume, wherein the exhalation valve connects the second volume and the exterior of the outer housing, and wherein gas is flowable from the inhaler to the first volume, from the first volume to the second volume, and from the second volume to the mouth of a patient.

The present disclosure can also be viewed as providing a spring apparatus. Briefly described, in architecture, one embodiment of the apparatus, among others, can be implemented as follows. A spring includes a spring body formed of a semi-pliant material with a strength and rigidity providing limited flexibility. The spring body has an elongate axis. A first separation is perpendicular to the elongate axis of the spring body. The first separation extends from a first edge of the spring body across at least a portion of a width of the spring body. A second separation is perpendicular to the elongate axis of the spring body. The second separation extends from a second edge of the spring body across at least a portion of the width of the spring body.

In one aspect of the spring, the first separation extends across a substantial portion of the width of the spring body.

In another aspect of the spring, the second separation extends across a substantial portion of the width of the spring body.

In another aspect of the spring, the spring body is formed from first and second adjacent layers fixed together along a plane. In a particular aspect, the first layer comprises the first and second separations. In a further particular aspect, the first and second separations extend through a thickness of the first layer. In another particular aspect, the second layer comprises at least one cutout adjacent to the first and second separations.

In another aspect of the spring, the first and second separations are spaced apart by a spaced distance. In a particular aspect, the spaced distance is substantially less than a length of the first and second separations.

In another aspect of the spring, a length of the first separation is different from a length of the second separation.

In another aspect of the spring, the first and second separations extend at least partially through a thickness of the spring body.

The present disclosure can also be viewed as providing a valve flap apparatus. Briefly described, in architecture, one embodiment of the apparatus, among others, can be implemented as follows. The valve flap includes a spring body formed of a semi-pliant material with a strength and rigidity providing limited flexibility. The spring body has an elongate axis. A first separation is perpendicular to the elongate axis of the spring body. The first separation extends from a first edge of the spring body across at least a portion of a width of the spring body. A second separation is perpendicular to the elongate axis of the spring body. The second separation extends from a second edge of the spring body across at least a portion of the width of the spring body. A living hinge is formed in the spring body and located a spaced distance from the first and second separations. An uncut section is located in the spaced distance between the living hinge and the first and second separations. The uncut section is positionable to prevent the flow of gas through a valve opening.

In one aspect of the valve flap, the living hinge comprises a plurality of central separations disposed between a plurality of edge separations, wherein the central separations extend perpendicular to the elongate axis of the spring body across a center of the width of the spring body, and wherein the edge separations extend perpendicular to the elongate axis of the spring body from the first and second edges of the spring body.

In another aspect of the valve flap, the first and second separations extend across a substantial portion of the width of the spring body.

In another aspect of the valve flap, the spring body is formed from first and second adjacent layers fixed together along a plane. In a particular aspect, the second layer comprises at least one cutout adjacent to the spring.

In another aspect of the valve flap, the first and second separations are spaced apart by a spaced distance. In a particular aspect, the spaced distance between the first and second separations is substantially less than a length of the first and second separations.

In another aspect of the valve flap, a second living hinge is formed in the spring body and located a spaced distance from the first and second separations opposite the first living hinge. A second uncut section is located in the spaced distance between the second living hinge and the first and second separations. The second uncut section is positionable to prevent the flow of gas through a valve opening. In a particular aspect, an end of the spring body near the first living hinge and an end of the spring body near the second living hinge are affixed to a valve surface.

The present disclosure also can be viewed as providing a medication inhalation apparatus. Briefly described, in architecture, one embodiment of the system, among others, can be implemented as follows. The apparatus is formed of a one piece cut and folded stock, includes an outer housing, movable between a collapsed state and an expanded state. The collapsed state has a substantially flat configuration. The expanded state encompasses a first volume. The apparatus also includes an inner barrier positioned within the outer housing, which together with portions of the outer housing, delineates a second volume. A first opening is formed at least partially within a wall of the outer housing at a first location, and adapted to accommodate a mouthpiece of an MDI inhaler, in fluid communication with the first volume. A second opening is positioned within a sidewall of the outer housing at a second location in fluid communication with the second volume. A one-way inhalation valve is positioned within a wall of the inner barrier. The inhalation valve connects the first volume and the second volume. A one-way exhalation valve is positioned within a wall of the outer housing and the inner barrier at a third location. The one-way exhalation valve connects the second volume to the exterior of the outer housing. The inhalation valve and the exhalation valve are both formed integrally with the housing, i.e., as one piece. When the apparatus is in an expanded state, gas is flowable from the metered dose inhaler to the first volume, from the first volume to the second volume, and from the second volume to the mouth of a user.

The present disclosure can also be viewed as providing methods of expanding a medication inhalation apparatus from an initially flat, collapsed state to an expanded state by providing a medication apparatus as above described, and manually pressing a pair of opposite sidewall panels on the outer housing towards one another, whereby to force the opposite sidewall panels into positions approximately perpendicular to top and bottom panels of the outer housing, and inserting a mouthpiece of an MDI inhaler into the mouthpiece opening in the outer housing, whereupon the apparatus is ready for use by a patient.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 6 is a flowchart describing a method of expanding a medication inhalation apparatus from an initially flat, collapsed state, in accordance with a first embodiment of the present disclosure.

FIG. 13 is a flowchart describing a method of expanding a medication inhalation apparatus from an initially flat, collapsed state, in accordance with a first embodiment of the present disclosure.

FIG. 20A is a close-up plan view of the sheet of FIG. 19, in accordance with a first exemplary embodiment of the present disclosure.

FIG. 22 is a plan view of a sheet from which the apparatus is constructed, in accordance with a second exemplary embodiment of the present disclosure.

FIG. 23 is a flowchart describing a method of expanding a medication inhalation apparatus from an initially flat, collapsed state, in accordance with a first embodiment of the present disclosure.

Figure 1A:
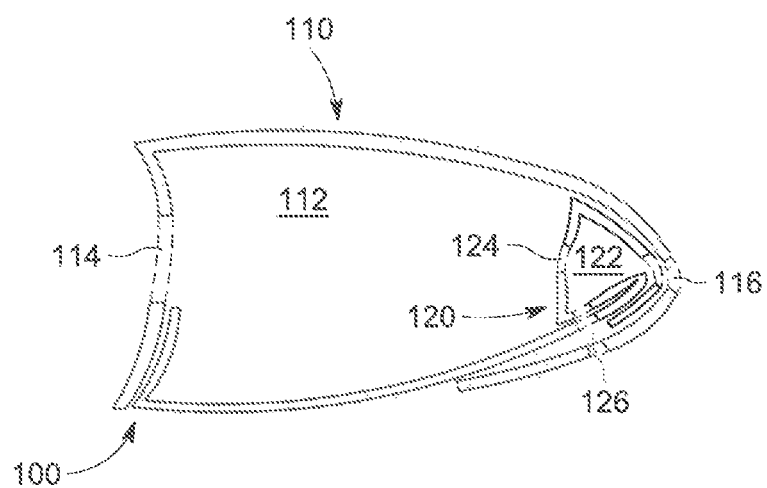
FIG. 1A is a longitudinal cross-sectional view of the apparatus in an expanded state, in accordance with a first exemplary embodiment of the present disclosure.

FIG. 1A is a longitudinal cross-sectional view of the apparatus 100 in an expanded state, in accordance with a first exemplary embodiment of the present disclosure. The apparatus 100 includes an outer housing 110, movable between a collapsed state and an expanded state. The collapsed state has a substantially flat configuration. The expanded state encompasses a first volume 112. The apparatus also includes an inner housing 120 positioned within the outer housing 110 and encompassing an inner volume 122. Housing 110 has perforations on the side and openings on the side that render it not airtight. Housing 120 has holes at the corners. The interface between volume 122 and 112 is the substantially airtight portion.

An inhaler opening 114 is formed at least partially within a sidewall of the outer housing 110 at a first location. The inhaler opening 114 is in fluid communication with the first volume 112, and the mouthpiece of a metered dose inhaler (see FIG. 3) can be inserted within the inhaler opening 114. A mouth opening 116 is positioned within a sidewall of the outer housing 110 and the inner housing 120 at a second location. The mouth opening 116 is in fluid communication with the inner volume 122. A one-way inhalation valve 124 is positioned within a sidewall of the inner housing 120. The inhalation valve 124 connects the first volume 112 and the inner volume 122. A one-way exhalation valve 126 is positioned within a sidewall of the outer housing 110 and the inner housing 120 at a third location. The exhalation valve 126 connects the inner volume 122 and the exterior of the outer housing 110. When the apparatus 100 is in an expanded state, gas is flowable from the metered dose inhaler to the first volume 112, from the first volume 112 to the inner volume 122, and from the inner volume 122 to the mouth of a user. In the expanded state, gas is also flowable from the mouth of a user to the inner volume 122 and to the exterior of the outer housing 110.

Figure 1B:
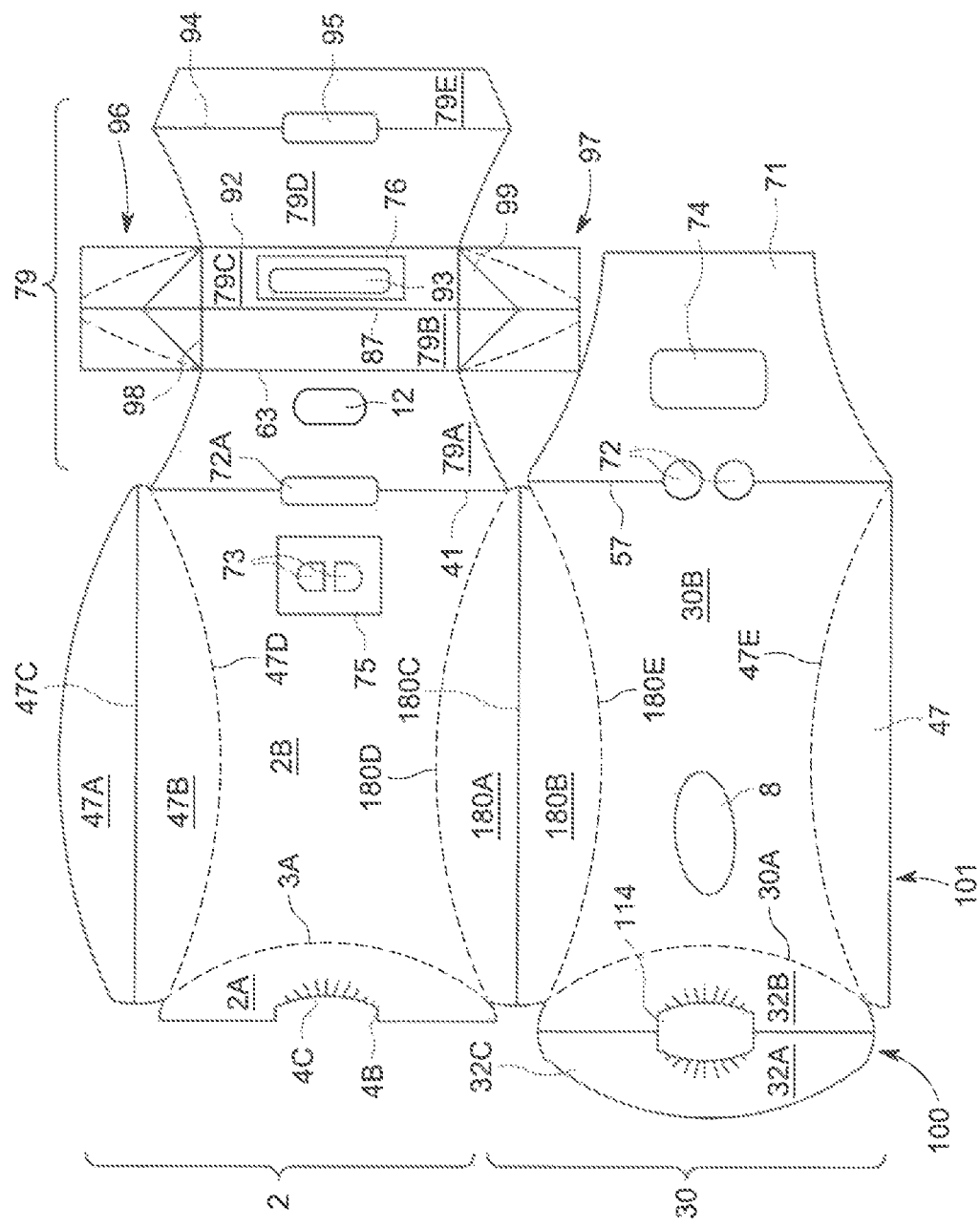
FIG. 1B is a plan view of a sheet from which the apparatus is constructed, in accordance with a first exemplary embodiment of the present disclosure.

FIG. 1B is a plan view of a sheet 101 from which the apparatus 100 is constructed, in accordance with a first exemplary embodiment of the present disclosure. The sheet 101, when assembled, pops up into the expanded state shown in FIG. 1A. FIG. 1B shows the exterior side of the sheet 101, i.e., the side that forms the exterior of the apparatus 100 as assembled. Sheet 101 includes a bottom section 2, a top section 30, an inner housing section 79, and an outer mouthpiece section 71. The inner housing 120 is formed from the panels in the inner housing section 79, while the outer housing 110 is formed from the remaining portions of the sheet 101. The bottom section 2 and top section 30 are connected by a right side section, which includes two right side panels 180A and 180B connected by a straight scored fold line 180C as shown. Right side panel 180A is connected along an arcuate "skip-scored" or perforated fold line 180D to bottom panel 2B, and right side panel 180B is connected along an arcuate skip-scored fold line 180E to top panel 30B. (A skip-scored fold line includes a sequence of scored and non-scored sections of a fold line having the appearance of dashed line).

On the top section 30, adhesive attachment panel 47 is connected by an arcuate scored or perforated fold line 47E to top panel 30B, and eventually is adhesively attached to the inner surface of left side panel 47A on bottom section 2. Left side panel 47A is connected to panel 47B, which is connected to bottom panel 2B by arcuate fold line 47D.

In one example, top panel 30B may have a window opening 8 therein, with a piece of transparent membrane adhesively attached to the inner surface of top panel 30B source to provide a sealed, transparent window into the interior of valved chamber 1A. In another example, the apparatus 100 may have no viewing window.

On the bottom section 2, the rear end portion of bottom panel 2B is connected along an arcuate skip-scored fold line 3A to an inner boot adapter panel 2A. Conversely, on the top section 30, an outer boot adapter panel 32A, B includes a panel 32A which is connected along a straight scored fold line 32C to an outer boot adapter panel 32B, which is connected along arcuate skip-scored fold line 30A to the rear end of top panel 30B. A portion of an elongated inhaler opening 114 bounded by scalloped sections 4B, which are formed by slits 4C, is aligned with a corresponding portion of half-opening 4B in inner boot adapter panel 2A.

Outer mouthpiece section 71 is connected along straight scored fold line 57 to top panel 30B. Circular openings 72 may be symmetrically formed in both top panel 30B and outer mouthpiece section 71, so as to be bisected by scored fold line 57. In another example, openings 72 may be any suitable shape, such as square, rectangle, oval, and the like. In another example, openings 72 may be located at any suitable point along top panel 30B. For instance, openings 72 may be exclusively located on top panel 30B or exclusively located on mouthpiece section 71. Or, openings 72 may be asymmetrically formed in both top panel 30B and mouthpiece section 71.

In one example, exhalation valve 126 (shown in FIG. 1A) may be formed on bottom section 2. A pair of exhalation valve openings 73 may be formed in bottom panel 2B, with an exhale membrane 75 attached along one side of exhalation valve openings 73 so as to cover them, and to flex away from exhalation valve openings 73 when a user exhales into inner volume 122 of inner housing 120. This allows exhaled breath to be exhausted through exhalation valve openings 73, and to seal them closed when the user inhales through openings 72.

Inner housing section 79 includes an elongated, trapezoidal panel 79A connected along straight scored fold line 41 to bottom panel 2B and a rectangular panel 79B connected along a straight scored fold line 63 to panel 79A. An elongated opening 12 in panel 79A becomes aligned with exhalation valve openings 73 when panel 79A is folded against the inner surface of bottom panel 2B as shown in FIG. 1A. When assembled, the portion of the apparatus 100 wherein opening 72A is located may be the mouth opening side of the apparatus 100.

In one example, an elongated rectangular opening 72A is symmetrically formed in bottom panel 2B and panel 79A so as to be bisected by fold line 41. Opening 72A may be any suitable shape to work in conjunction with openings 72. Opening 72A may comprise one or more openings to work in conjunction with openings 72. Opening 72A may be located at any point on bottom panel 2B or panel 79A to work in conjunction with openings 72. For instance, depending on the location of openings 72, opening 72A may be located entirely on bottom panel 2B, entirely on panel 79A, or asymmetrically formed within both bottom panel 2B and panel 79A.

Panel 79B is connected to another panel 79C along a straight scored fold line 87. A rectangular inhalation valve opening 93 is formed centrally in panel 79C. A rectangular inhalation membrane 76 is adhesively attached to the outer surface of the sheet 101 so as to cover inhalation valve opening 93 and flex to uncover inhalation valve opening 93 as the user inhales through openings 72 and 72A. Also, the opening of the flap necessarily causes a change in airflow direction, which has been shown to be advantageous in further reducing CPD in some papers. Panel 79E may be adhesively connected to the exterior of panel 2B upon assembly.

Panel 79C is attached to trapezoidal panel 79D along a straight skip-scored fold line 92. Preferably, inhalation valve opening 93 is as large as can be practically fit into panel 79C while nevertheless providing adequate room both for attachment of inhalation membrane 76 to panel 79C and for proper operation of inhalation membrane 76.

Trapezoidal panel 79E is connected to panel 79D along a continuously scored fold line 94. In one example, opening 95 is located symmetrically between panels 79D and 79E.

Side panels 96 and 97 are connected to panels 79B and 79C along straight, continuously-scored fold lines 98 and 99. Side panels 96 and 97, which are unique to the instant invention, and make the interface between the first volume 112 and the inner volume 122 substantially air tight, and which differentiate the instant apparatus from the LiteAire® device and apparatus disclosed in prior U.S. Pat. No. 6,679,252, are discussed in greater detail in FIG. 2, below.

It should be noted that all openings may have any size, shape, orientation, number, and placement suitable to work in conjunction with each other and to facilitate use by a user. FIGS. 1A and 1B show exemplary openings generally located centrally on the apparatus 100.

Figure 2:
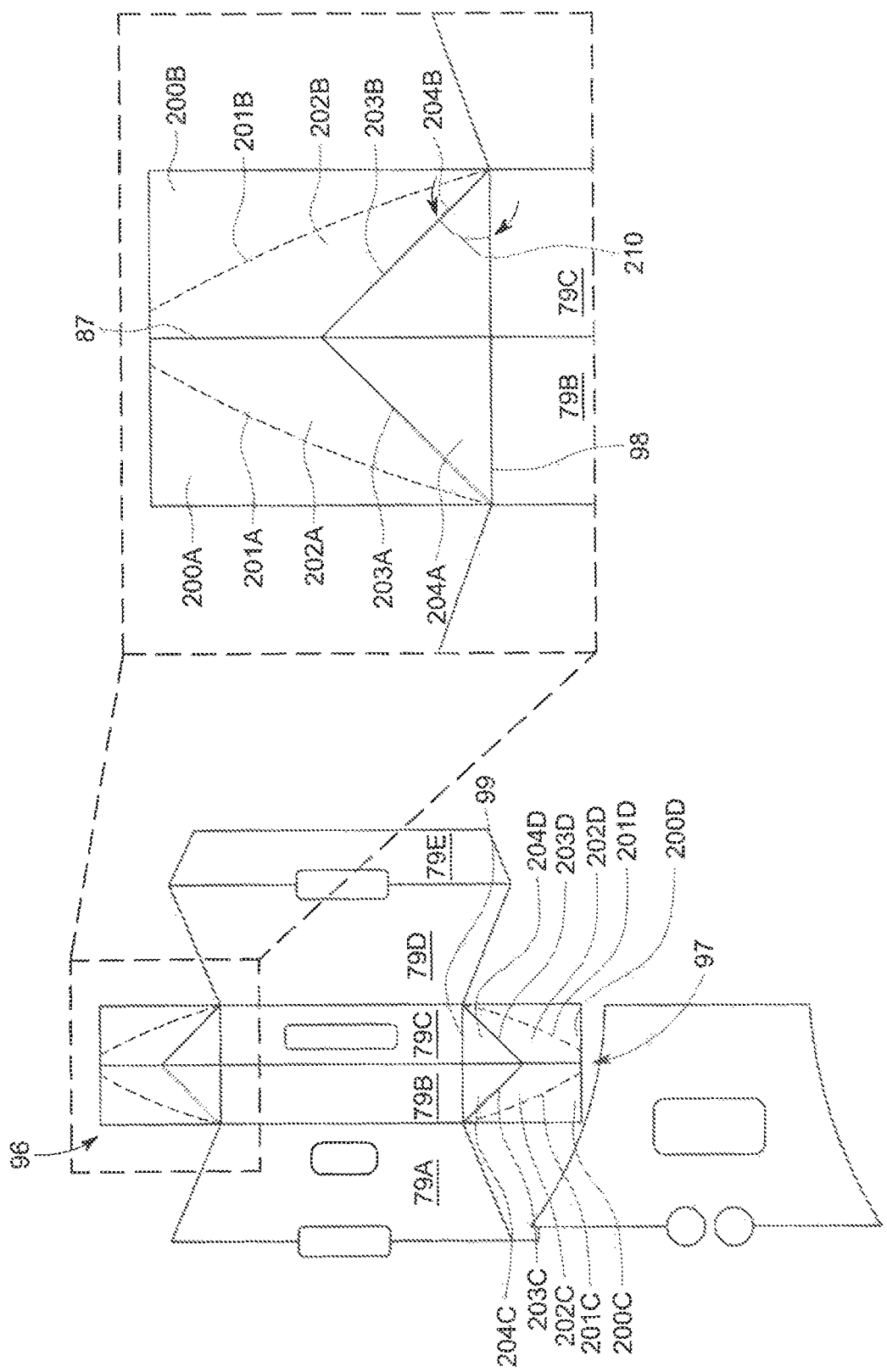
FIG. 2 is a close-up plan view of the sheet of FIG. 1B, in accordance with a first exemplary embodiment of the present disclosure.

FIG. 2 is a close-up plan view of the sheet 101 of FIG. 1B, in accordance with a first exemplary embodiment of the present disclosure. FIG. 2 shows the portion of the sheet 101 that, when assembled, forms the inner housing 120 of FIG. 1A. Panels 79A-E are shown connected by score lines. Connected to panels 79B and 79C are side panels 96 and 97. In the example shown in FIG. 2, side panels 96 and 97 are the same design on opposite sides of side panels 79B and 79C. Left and right sides of side panels 96 and 97 are also symmetrical about line 87.

Side panel 96 is shown within the close-up inset. Side panel 96 is a shown as a rectangular panel comprising several flaps differentiated by diagonal scoring or perforation lines. On the left side, flaps 200A and 202A are differentiated by skip-scored fold line 201A. Flaps 202A and 204A are differentiated by perforation or scored line 203A. And flap 204A is differentiated from panel 79B by continuous score line 98. On the right side, flaps 200B and 202B are differentiated by skip-scored fold line 201B. Flaps 202B and 204B are differentiated by perforation line 203B. And flap 204B is differentiated from panel 79C by continuous score line 98. In one example, the angle 210 between score line 98 and perforation lines 204A or 204B may be 45°. The angle 210 may be more or less depending on the size and shape of the flaps.

Side panel 97 comprises reciprocal flaps differentiated by diagonal scoring or perforation lines. On the left side, flaps 200C and 202C are differentiated by skip-scored fold line 201C. Flaps 202C and 204C are differentiated by perforation line 203C. And flap 204C is differentiated from panel 79B by continuous score line 99. On the right side, flaps 200D and 202D are differentiated by skip-scored fold line 201D. Flaps 202D and 204D are differentiated by perforation line 203D. And flap 204D is differentiated from panel 79C by continuous score line 99. In one example, the angle between score line 99 and perforation lines 204C or 204D may be 45°. The angle may be more or less depending on the size and shape of the flaps.

The left and right sides of side panels 96 and 97 are differentiated by continuous score line 87, which runs from side panel 96, between panels 79B and 79C, and through side panel 97. Each of the score or perforation lines 201A-D, 203A-D, 98, 99 runs from a point along line 87 to an outer corner of the side panel 96, 97.

When assembled, the side panels 96, 97 fold inward to create an inner housing 120. The side panels 96, 97 become sidewalls for the housing 120. While the chamber itself is not airtight, the interface between the inner volume and the outer volume is substantially airtight. Additionally, the sidewalls limit fluid connection with the first volume 112 and the ambient external environment of the apparatus 100.

Referring to FIGS. 1A-2, the apparatus 100 may be constructed from the sheet 101 as follows. For ease of description, reference will be made to the "topside" and "underside" of the panels and flaps comprising sheet 101, the "topside" being the portion of the panel or flap visible in FIGS. 1B, 2, while the "underside" is the opposite side not visible in the drawings.

In one example, the apparatus 100 is cut or punched from a single, unitary sheet 101 of suitable material, such as solid bleached sulfate paperboard, plastic, spun nonwoven polymer such as TYVEK® by DuPont, or the like. In another example, the apparatus 100 may be assembled from a plurality of pieces or sheets of suitable material. The material may be an antistatic or static dissipative paper to reduce static deposition of medicine particles on the walls of the apparatus 100. In one example, the sheet 101 may be coated in a static dissipative coating or the like. Inhalation valve 124, exhalation valve 126, and optional viewing window 8 may be first created by adhesively attaching membranes 76, 75, 8 to the appropriate surface of sheet 101 as discussed relative to FIG. 1B. The membranes 76, 75, and 8 may be any suitable material capable of creating a substantially airtight valve or window while also remaining flexible. In one example, the membranes 76, 75, and 8 may be a thin plastic, and polymer, and the like.

The inner housing 120 may be assembled next. The panels and flaps may be fixed or glued together using one or more suitable adhesives. The folding and gluing process starts by applying adhesive to the underside of panel 79A. Panel 79A is folded over so that the adhesive side contacts the underside of bottom panel 2B. Line 87 and the diagonal folds 201A-D, 203A-D run upward and toward the topside of panels 79B, 79C. Adhesive is applied to the underside of flaps 200A-D. Line 87 and lines 204A, B are used to fold panel 96 as a reverse fold to line up the undersides of panels 200A and 200B to the topsides of panels 79A and 79D, respectively. Line 87 and lines 204C, D are used to fold panel 97 as a reverse fold to line up the undersides of panels 200C and 200D to the topsides of panels 79A and 79D, respectively. Panels 79A and 79D are folded along lines 63 and 92, respectively, to bring the topsides of these panels into the corresponding undersides of panels 200A-D. Glue is applied to the topside of panel 79E. Panel 79E is folded along line 94 and glued to the topside of bottom panel 2B.

The outer housing 110 may be assembled around the inner housing 120 next. Adhesive is applied to the underside of panel 79D. The sheet 101 is folded along line 180C so that the undersides of top panel 2 and bottom panel 30 are folded toward one another. The underside of panel 79D is glued to the underside of top panel 30B. Glue is applied, in any appropriate order, to the undersides of panels 47A and 32A. Panel 47A is glued to the topside of panel 47. Panel 32A is glued to the topside of panel 2A. Glue is applied to the underside of panel 71, which is folded along line 57 and glued to the topside of bottom panel 2B over panel 79E.

Figure 3:
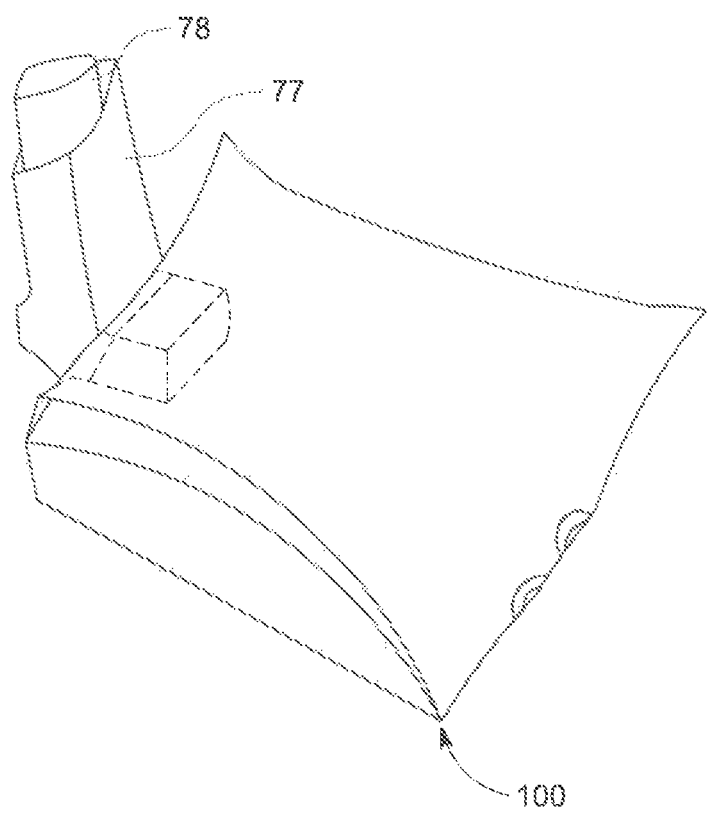
FIG. 3 is a perspective view of the apparatus in an expanded state, in accordance with a first exemplary embodiment of the present disclosure.

FIG. 3 is a perspective view of the apparatus 100 in an expanded state, in accordance with a first exemplary embodiment of the present disclosure. In the expanded state, apparatus 100 is capable of receiving the mouthpiece end of the boot adapter 77 of a conventional inhaler containing an MDI canister 78 inserted through inhaler opening 114 shown in FIG. 1A.

Referring to FIGS. 1A-3, the apparatus 100 may be expanded as follows. When the apparatus 100 is assembled as described above, it is in its flat or collapsed state. If the user presses right side panels 180A and 180B inward toward left side panels 47A and 47B so that they "unfold" along straight, scored fold lines 180C and 47C, respectively, the apparatus 100 pops up into and retains the configuration shown in FIG. 3. The fold lines 63, 87, and 92 allow panels 79B and 79C to be pulled by adhesive and 79D and the rising upper panel 30B upward from their generally horizontal position when apparatus 100 is collapsed so that the panel 79B,C is in a nearly vertical position when apparatus 100 is fully "popped up".

Figure 4:
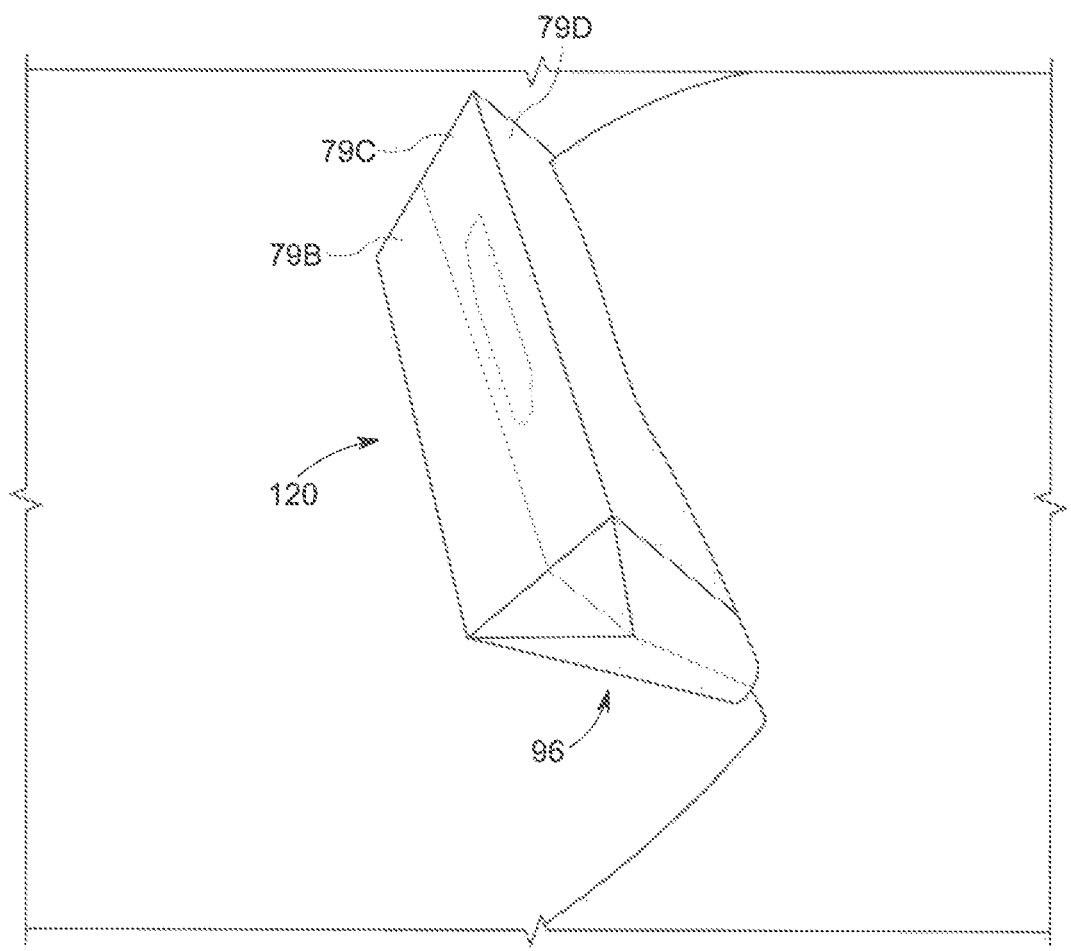
FIG. 4 is a perspective view of the inner housing in an expanded state, in accordance with a first exemplary embodiment of the present disclosure.

Additionally, when the boot adapter 77 with an MDI canister 78 therein is inserted into opening 114, that causes boot adapter panels 32A and 32B to unfold to the maximum extent FIG. 4 is a perspective view of the inner housing 120 in an expanded state, in accordance with a first exemplary embodiment of the present disclosure. In the exemplary embodiment shown in FIG. 4, inner housing 120 is a pyramid connected by panels 79D, 79C, 79B, 96, 97 (not shown), and 79A (not shown). Score line 201A is folded, where score line 203A is not folded, meaning panels 204A and 202A are coplanar, and panel 200A is roughly at a 90° angle with panels 204A and 202A. Panel 97, on the opposite side, has the same configuration. The expanded inner housing 120 may be shaped as any hollow polyhedron connected by panels. In one example, a number of the panels substantially abut portions of the outer housing 110. For instance, the inner housing 120 shown in FIG. 4 may abut the outer housing 110 at panels 96, 97, 79A, and 79D. An inner housing 120 with more sides may abut the outer housing on additional sides.

Referring to FIGS. 1A-4, the inner housing 120 may be expanded as follows. The outer housing 110 of the apparatus 100 is unfolded as described above. As this unfolding occurs, and as right side panels 180A and 180B move inward and engage side panel 97, side panel 97 also is pressed inward. Similarly, as left side panels 47A and 47B move inward and engage side panel 96, side panel 96 also is pressed inward. This causes side panels 96, 97 to fold along fold lines 98, 99 into the configuration shown in FIG. 4. Thus, side panels 96, 97 form a seal with panels 79A-D. Left side panels 47A-B and right side panels 180A-B reinforce the seal by supporting side panels 96 and 97. This effectively reduced or minimizes both inhaled air and exhaled air from bypassing the inhalation valve, substantially increasing the efficiency of the apparatus 100 by reducing or minimizing air inadvertently exhaled (rather than inhaled) by a user during activation of an MDI canister in a boot adapter from being forced around panels 79B and 79C. Additionally, this prevents the inadvertently exhaled air from forcing some of the MDI medication to leak out into the atmosphere between the periphery of opening 114 and the periphery of the MDI boot adapter. The efficiency of the apparatus 100 is thereby increased substantially.

Figure 5:
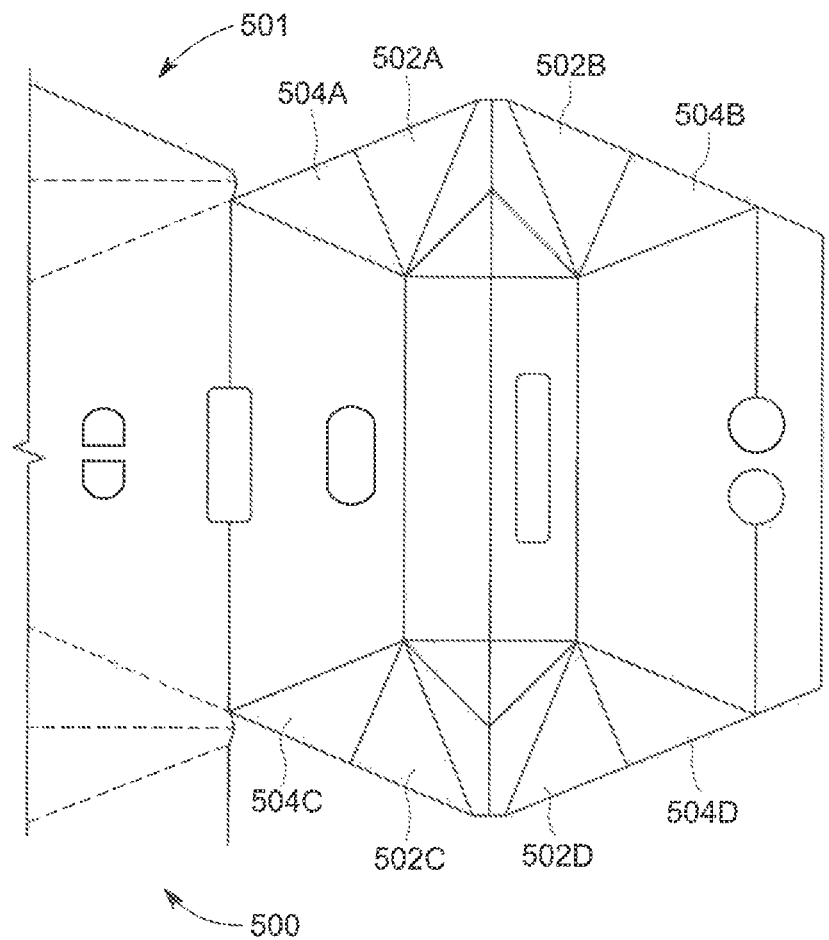
FIG. 5 is a close-up plan view of a sheet from which the apparatus is constructed, in accordance with a second exemplary embodiment of the present disclosure.

FIG. 5 is a close-up plan view of a sheet 501 from which the apparatus 500 is constructed, in accordance with a second exemplary embodiment of the present disclosure. In one example, the design of the sheet 501 may be substantially similar to sheet 101 shown in FIG. 1B, with the exception of additional flaps 502A-D, 504A-D used to form the sides of the inner housing. The additional flaps 502A-D, 504A-D are folded along the score lines shown to create webbed panels of the inner housing. These folded, webbed panels make the inner housing more airtight at the corners of the housing wall when expanded by providing a more robust seal. Other webbed panel designs may be used to provide an airtight seal at the corners of the inner housing.

FIG. 6 is a flowchart 600 describing a method of expanding a medication inhalation apparatus from an initially flat, collapsed state, in accordance with a first embodiment of the present disclosure. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

In step 610, an outer housing, an inner housing positioned within the outer housing, wherein the outer housing and the inner housing are substantially airtight when expanded, an inhaler opening formed at least partially within a sidewall of the outer housing at a first location, a mouth opening positioned within a sidewall of the outer housing and the inner housing at a second location, a one-way inhalation valve positioned within a sidewall of the inner housing, and a one-way exhalation valve positioned within a sidewall of the outer housing and the inner housing at a third location are provided in the collapsed state.

In step 620, a pair of opposite sidewall panels on the outer housing is pressed.

In step 630, the outer housing and inner housing are manually expanded to create a first volume encompassed by the outer housing and an inner volume encompassed by the inner housing, wherein the inhaler opening is in fluid communication with the first volume, wherein the mouth opening is in fluid communication with the inner volume, wherein the inhalation valve connects the first volume and the inner volume, wherein the exhalation valve connects the inner volume and the exterior of the outer housing, and wherein gas is flowable from the metered dose inhaler to the first volume, from the first volume to the inner volume, and from the inner volume to the mouth of a user.

Figure 7:
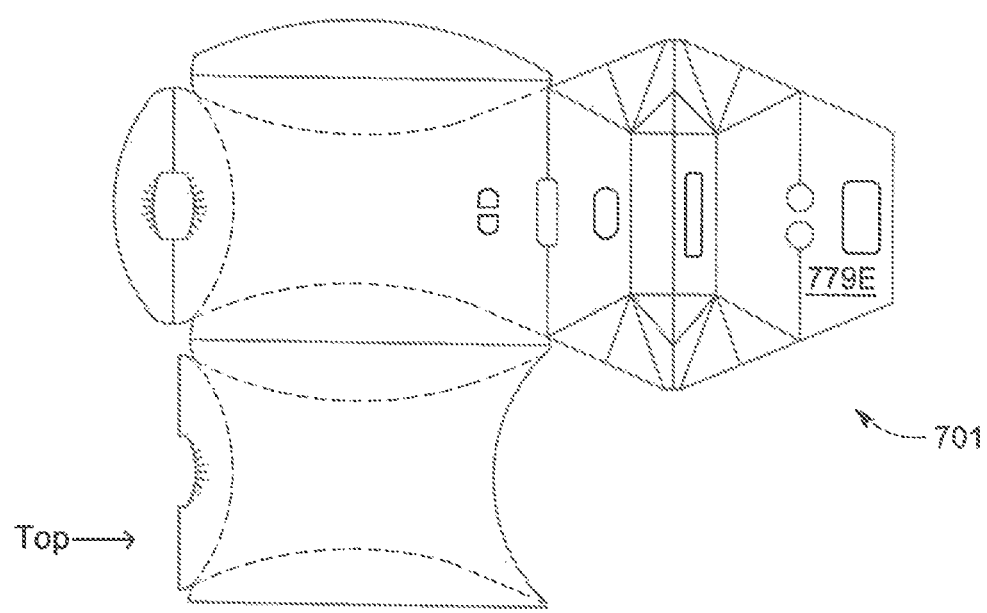
FIG. 7 is a plan view of a sheet from which the apparatus in accordance with a third embodiment of the present disclosure is constructed.

FIG. 7 is a plan view of a sheet 701 from which the apparatus is constructed, in accordance with a second exemplary embodiment of the present disclosure. In this example, the design of the sheet 701 is substantially similar to sheet 101 shown in FIG. 1B, with the additions shown in FIG. 5. However, in this case the front panel 779E for the inner housing, corresponding to panel 79E of the FIG. 2 embodiment, is elongated. Front panel 79E is used to form the mouthpiece, instead of a panel 71 from the outer housing of FIG. 1B, folding to form the mouthpiece. Other than that, the FIG. 7 embodiment is similar to the FIG. 1B embodiment.

Operating Example

The following operating example may illustrate how the apparatus 100 is used in implementation.

The apparatus 100 may be assembled as described relative to FIGS. 1A-2 above. The outer housing 110 may be expanded as described relative to FIG. 3, and the inner housing 120 expanded as described relative to FIG. 4. A user may insert the mouthpiece end of the boot adapter 77 of an inhaler container an MDI canister 78 through the inhaler opening 114 of the apparatus 100 until it fits snugly. The user may place their mouth on the mouth opening 116, and may exhale into the inner housing 120. The user's exhaled breath may exit the inner housing 120 through the exhalation valve 126. Increased pressure in the inner housing 120 may cause membrane 75 to flex away from exhalation valve openings 73, allowing the exhaled breath to escape the apparatus 100. As the user finishes exhaling, the membrane 75 may return to its "closed" position on the apparatus 100, reducing or minimizing the amount of air entering the apparatus 100. The user may next engage the MDI canister 78 to spray medicine into the first volume 112 of the outer housing 110. The medicine may briefly remain in the first volume 112. The user may inhale through the apparatus 100, causing the inhalation valve 124 to open. Membrane 76 may flex into the inner volume 122 of the inner housing 120, allowing the medicine to travel from the first volume 112 to the inner volume 122. As the user continues to inhale, the medicine may continue to travel from the inner volume 122 into the user's mouth through the mouth opening 116. After the user has finished inhaling, the membrane 76 may return to its "closed" position on the inner housing 120, reducing or minimizing the amount of air from the outer housing 110 from entering the inner housing 120.

In some examples, the user may perform some of the steps in a different order. For instance, the user may engage the MDI canister 78 to spray before exhaling, or the user may wait some time between engaging the MDI canister 78 and inhaling. The apparatus 100 is designed to deliver an effective dose even under these conditions.

Test Examples

The following test example may illustrate the effectiveness of the apparatus 100 in creating a medication inhalation apparatus with improved medication delivery.

Three units of the subject apparatus 100, made from 16 pt SBS paperboard, were tested against a Monaghan Aerochamber Z-stat, a non-disposable valved holding chamber. The particle size distributions of the two devices were compared with both coordinated and uncoordinated breathing. Coordinated breathing is defined as actuation of the MDI occurring during the onset of user inhalation. Uncoordinated breathing is defined as actuation of the MDI occurring during the onset of user exhalation. A good metric of the efficacy of the apparatus 100 to mitigate user incoordination is the amount of dose lost from the coordinated breathing test to the uncoordinated breathing test. The Aerochamber unit tested gave a 38% drop in total emitted dose from coordinated to uncoordinated breathing, while the subject apparatus 100 showed, on average, no drop from coordinated to uncoordinated breathing in total emitted dose.

Thus, the invention provides a disposable "pop up", valved apparatus 100 which also allows for natural inhalation and exhalation by a user. The described valved apparatus 100 can be maintained in a collapsed, flat configuration, suitable for storage in a pocket, pocketbook or a briefcase, and expanded just prior to use, after which it can be discarded or re-folded for later use by the same user. The described apparatus 100 may be used by health care workers to demonstrate its use to users needing to receive an aerosol medication from an MDI inhaler. The apparatus 100 also is well suited for use in hospital emergency rooms, health-care clinics, pulmonary function labs, or infirmaries. In addition, its portability and low cost make it ideal for use by relief or world health organizations, especially when aerosol vaccines become available.

A medication inhalation apparatus 800 now will be discussed relative to FIGS. 8A-8C and 9. The apparatus 800 may be formed from a sheet 801. The sheet 801 may be cut, folded, scored, perforated, secured, and formed in a similar manner to the sheet 101 in FIGS. 1A-1B and as described herein below, depending on the shape and placement of lines and perforations in the sheet 801. In one example, the sheet 801 may be made from the same materials as the sheet 101 discussed above relative to FIGS. 1A-1B, and may be secured using the same adhesives and methods. For instance, the sheet 801 may be constructed from a single piece of stock. The single piece may be sheet stock. In another example, the sheet 801 may be at least partially constructed from antistatic material.

Figure 8A:
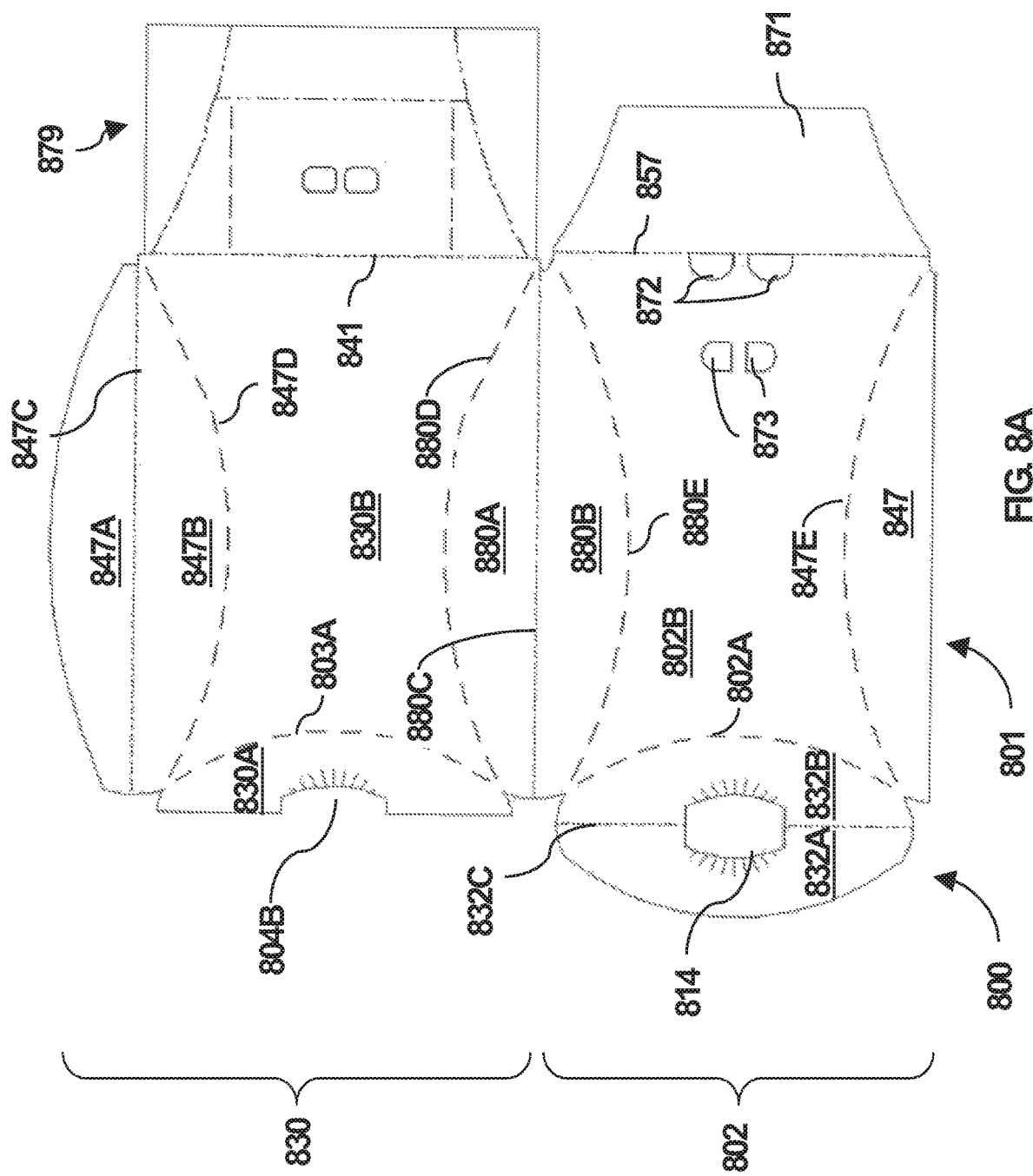
FIG. 8A is a plan view of a sheet from which a medication inhalation apparatus is constructed, in accordance with a fourth exemplary embodiment of the present disclosure.

FIG. 8A is a plan view of a sheet 801 from which the medication inhalation apparatus 800 is constructed, in accordance with a fourth exemplary embodiment of the present disclosure. The sheet 801, when assembled, pops up into the expanded state shown in FIG. 9. FIG. 8A shows the interior side of the sheet 801, i.e., the side that forms the interior of the apparatus 800 as assembled. Sheet 801 includes a bottom section 802, a top section 830, an inner flap 879, and an outer mouthpiece section 871. The inner flap 879 may form at least one boundary of a second volume within an outer housing formed by the sheet 801. The inner flap 879 is discussed in greater detail in FIG. 8B, and the second volume is discussed in greater detail in FIG. 9, below. Inner flap 879 is connected to top panel 830B along straight scored fold line 841. The bottom section 802 and top section 830 are connected by a right side section, which includes two right side panels 880A and 880B connected by a straight scored fold line 880C as shown. Right side panel 880A is connected along an arcuate "skip-scored" or perforated fold line 880D to top panel 830B, and right side panel 880B is connected along an arcuate skip-scored fold line 880E to bottom panel 802B.

On the bottom section 802, adhesive attachment panel 847 is connected by an arcuate scored or perforated fold line 847E to bottom panel 802B, and eventually is adhesively attached to the inner surface of left side panel 847A on top section 830. Left side panel 847A is connected to panel 847B across straight scored fold line 847C. Panel 847B is connected to top panel 830B by arcuate fold line 847D.

On the top section 830, the rear end portion of top panel 830B is connected along an arcuate skip-scored fold line 803A to an inner boot adapter panel 830A. Conversely, on the bottom section 802, an outer boot adapter panel 832A, B includes a panel 832A which is connected along a straight scored fold line 832C to an outer boot adapter panel 832B, which is connected along arcuate skip-scored fold line 802A to the rear end of bottom panel 802B. A portion of an elongated inhaler opening 814 bounded by scalloped sections formed by slits is aligned with a corresponding portion of half-opening 804B on top section 830A.

Outer mouthpiece section 871 is connected along straight scored fold line 857 to bottom panel 802B. Circular openings 872 may be formed in bottom panel 802B at the scored fold line 857. In another example, openings 872 may be any suitable shape, such as square, rectangle, oval, and the like. In another example, openings 872 may be located at any suitable point along bottom panel 802B. For instance, openings 872 may be exclusively located on bottom panel 802B or exclusively located on mouthpiece section 871. Or, openings 872 may be formed in both bottom panel 802B and mouthpiece section 871.

In one example, a pair of exhalation valve openings 873 may be formed in bottom panel 802B. The exhalation valve openings 873 may be covered by an exhale membrane such as the one described relative to FIGS. 1A-1B. This allows exhaled breath to be exhausted through exhalation valve openings 873, and to seal them closed when the user inhales through openings 872.

It should be noted that all openings may have any size, shape, orientation, number, and placement suitable to work in conjunction with each other and to facilitate use by a user. FIGS. 8A-8C and 9 show exemplary openings generally located centrally on the apparatus 800.

Figure 8B:
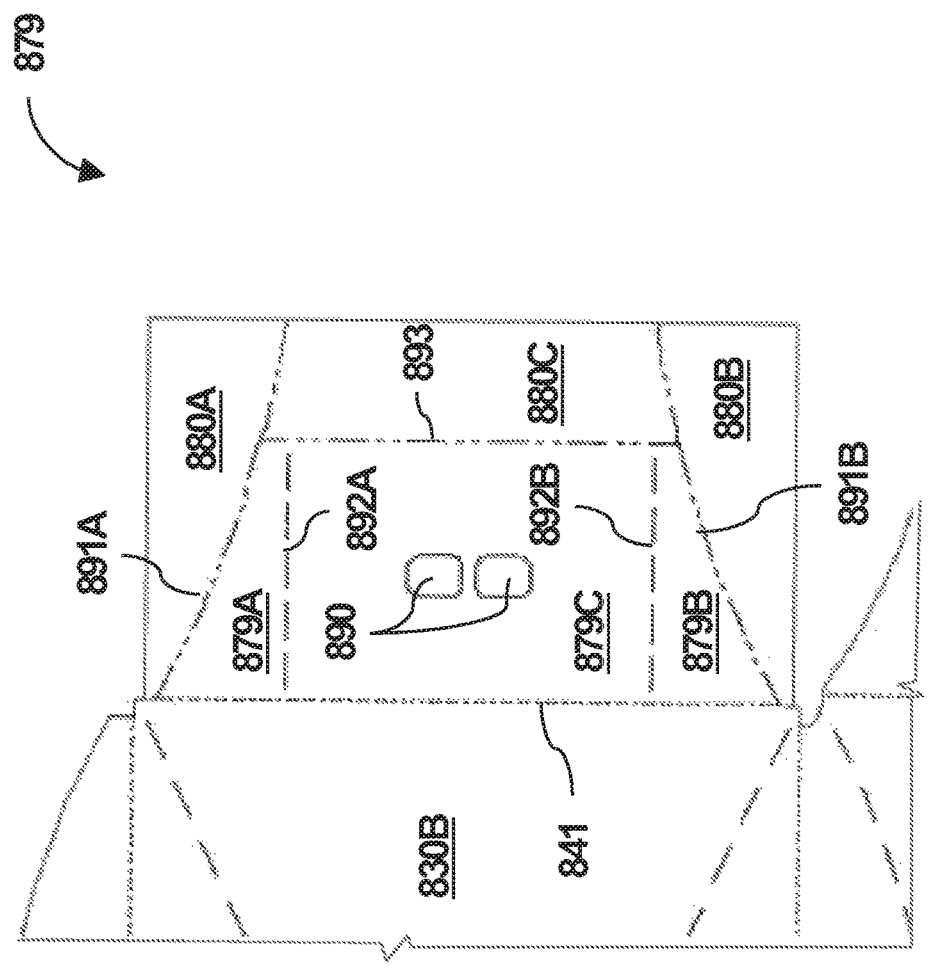
FIG. 8B is a close-up plan view of the inner flap shown in FIG. 8A, in accordance with the fourth exemplary embodiment of the present disclosure.

FIG. 8B is a close-up plan view of the inner flap 879 shown in FIG. 8A, in accordance with the fourth exemplary embodiment of the present disclosure. The inner flap 879 may be shaped as a rectangle comprising several panels joined across cut-scored or skip-scored lines. Left outer panel 880A may be connected to left inner panel 879A and center outer panel 880C by a curved cut score 891A. Likewise, right outer panel 880B may be connected to right inner panel 879B and center outer panel 880C by a mirrored curved cut score 879B. Left and right inner panels 879A, B may be connected to center inner panel 879C across straight skip score lines 892A, 892B, respectively. Center inner panel 879C may be connected to center outer panel 880C across a straight cut score line 893. Valve openings 890 may be located at any suitable position on center inner panel 879C. There may be any number, size, shape, and orientation of valve openings 890 to allow gas to flow between the chambers of the apparatus 800. The inner flap 879 may be connected to top panel 830B along scored line 841. Scored line 841 may extend across the entirety of top panel 830B.

Referring to FIGS. 8A-8B, the apparatus 800 may be folded and assembled in the following manner: The inner flap 879 may be folded and glued as described herein to create a second volume within the apparatus 800 to allow a user to exhale air and inhale medicine. The inner flap 879 may be folded along scored line 841 onto the top panel 830B. An adhesive may be applied as described in FIG. 10, below. Inner flap 879 may be adhered to bottom panel 802B along the points of adhesive. Bottom panel 802B may be folded along straight scored fold line 880C to sandwich inner flap 879 between bottom panel 802B and top panel 830B. Outer boot adapter panel 832A may be folded along straight scored fold line 832C. Adhesive may be applied to outer boot adapter panel 832A, and outer boot adapter panel 832A may be glued to the underside of inner boot adapter panel 830A to secure the inhaler side of the apparatus 800. Adhesive may be applied to left side panel 847A. Left side panel 847A may be folded along straight scored fold line 847C over adhesive attachment panel 847. Left side panel 847A may be glued to the underside of adhesive attachment panel 847 to secure the side of the apparatus 800. Adhesive may be applied to outer mouthpiece section 871. Outer mouthpiece section 871 may be folded along scored fold line 857 to contact the underside of top panel 830. Outer mouthpiece section 871 may be glued to the underside of top panel 830 to secure the mouthpiece side of the apparatus 800.

Figure 8C:
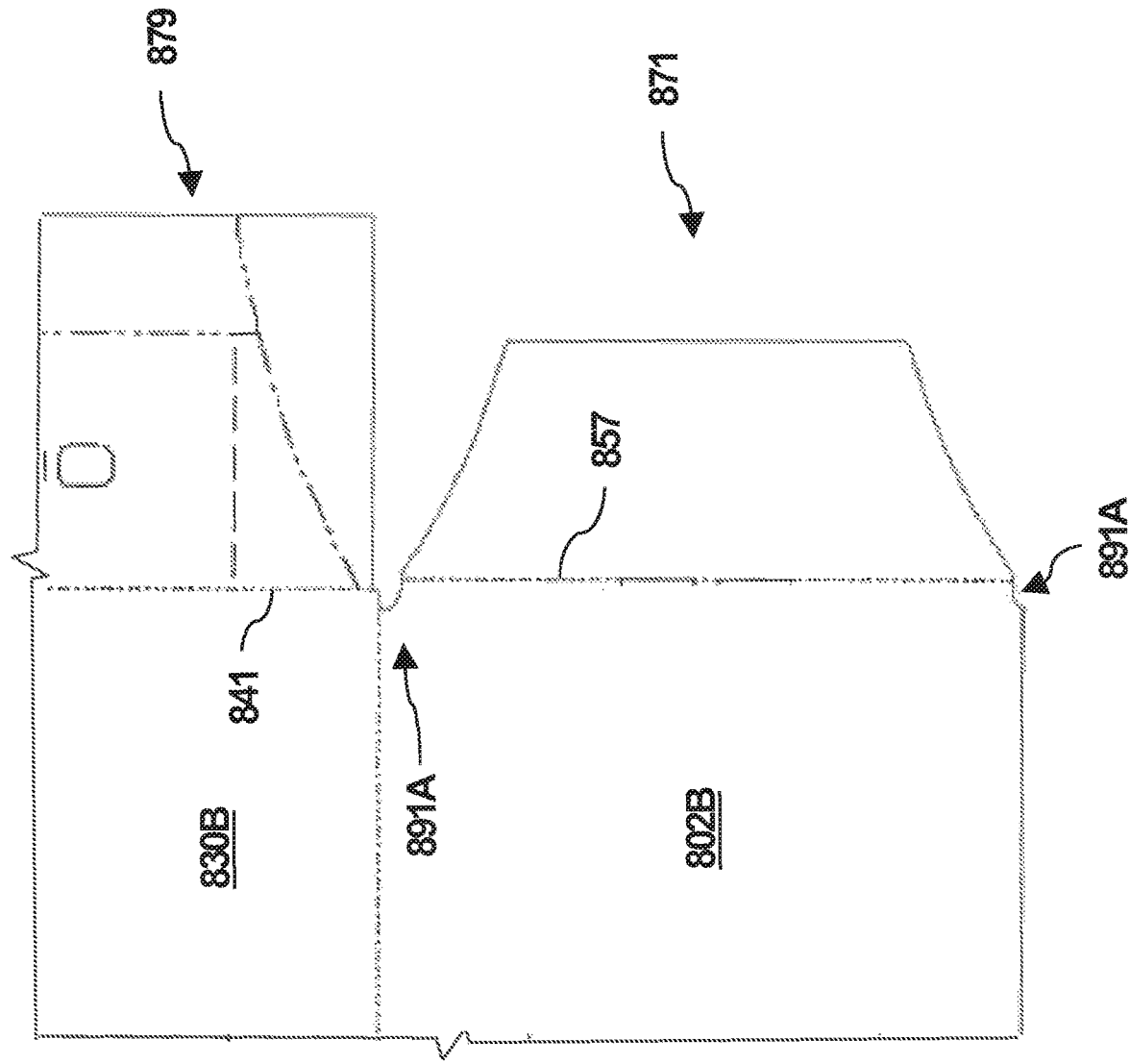
FIG. 8C is a close-up plan view of the outer mouthpiece section shown in FIG. 8A, in accordance with the fourth exemplary embodiment of the present disclosure.

FIG. 8C is a close-up plan view of the outer mouthpiece section 871 shown in FIG. 8A, in accordance with the fourth exemplary embodiment of the present disclosure. FIG. 8C shows the bottom panel 802B and the top panel 830B. The bottom panel 802B has receded corners 891A that are not squared—at a right angle—but are beveled inward toward the bottom panel 802B. When the apparatus 800 is folded, and the top panel 830B is located on top of the bottom panel 802B, the receded corners 891A allow the corners of the inner flap 879 to protrude past the corners 891A of the bottom panel 802B. This is important because when the apparatus 800 is folded and glued, there may be openings at the corners of the device. These receded corners 891A direct any air coming out of the corners out the sides of the apparatus 800 or toward the user, but not toward the first volume containing the drug. Directing the air in this way reduces the amount of air passing back into the first volume during user exhalation.

FIG. 8C also illustrates a difference in the alignment between scored line 841 and scored fold line 857. As shown in FIG. 8C, scored fold line 857 is located further to the right than scored line 841—meaning, in other words, that bottom panel 802B extends longer than top panel 830B. This may improve the shape of the inner flap 879 with respect to the second volume created when the apparatus 800 is expanded. When the apparatus 800 is expanded, the inner flap 879 is shorter than the length of the same point on the bottom panel 802B. Because of this, the inner flap 879 forms a straight line between the attachment surfaces—top and bottom panels 830B, 802B—while the bottom panel 802B matches the curved profile of perforated fold lines 880E, 847E. This creates a space between the inner panel 879 and the bottom panel 802B which may become the second volume and may be used as a mouthpiece for the apparatus 800.

There are many aspects of the design that contribute to the functioning of the apparatus 800. These design features are the receded corners on the outer flap 871, discussed above, the tension relief lines on the inner flap 879, and the perforation lines 847D, 880D near the mouthpiece. The design of the apparatus 800 means that a lot of tension exists in the inner flap 879 of the apparatus 800, namely in bending the inner flap 879 to form high points where the inner flap 879 attaches to the sides of the apparatus 800, and a low point in the middle of the inner flap 879. This type of "U" bend would be seen in the inhalation valve, which would increase the valve resistance, possibly out of specification, or cause creasing to occur around the vents 890 because they created a relief point for the tension. Both of these problems are overcome by the addition of the tension relief lines 892A, 892B. These tension relief lines 892A, B redirect the flexural tension to crease along these lines instead of across the inhalation vents. These lines may be perforated, though perforation would let a slight amount of air through the perforation cuts. A better option may be to use cut score lines instead of perforation lines. These lines may be straight, as depicted, or may also have any suitable shape or curvature.

The perforation lines 847D, 880D near the mouthpiece of the apparatus 800 are positioned so that the projected line made by the perforations meets the corners of the top panel 830B. This allows there to be little to no gap at the corner where the perforations 847D, 880D meet the corners of the top panel when the apparatus 800 is expanded. On the bottom panel, the perforations do not meet the corners, and so there is a slight opening at the corners when the apparatus 800 is expanded.

Figure 9:
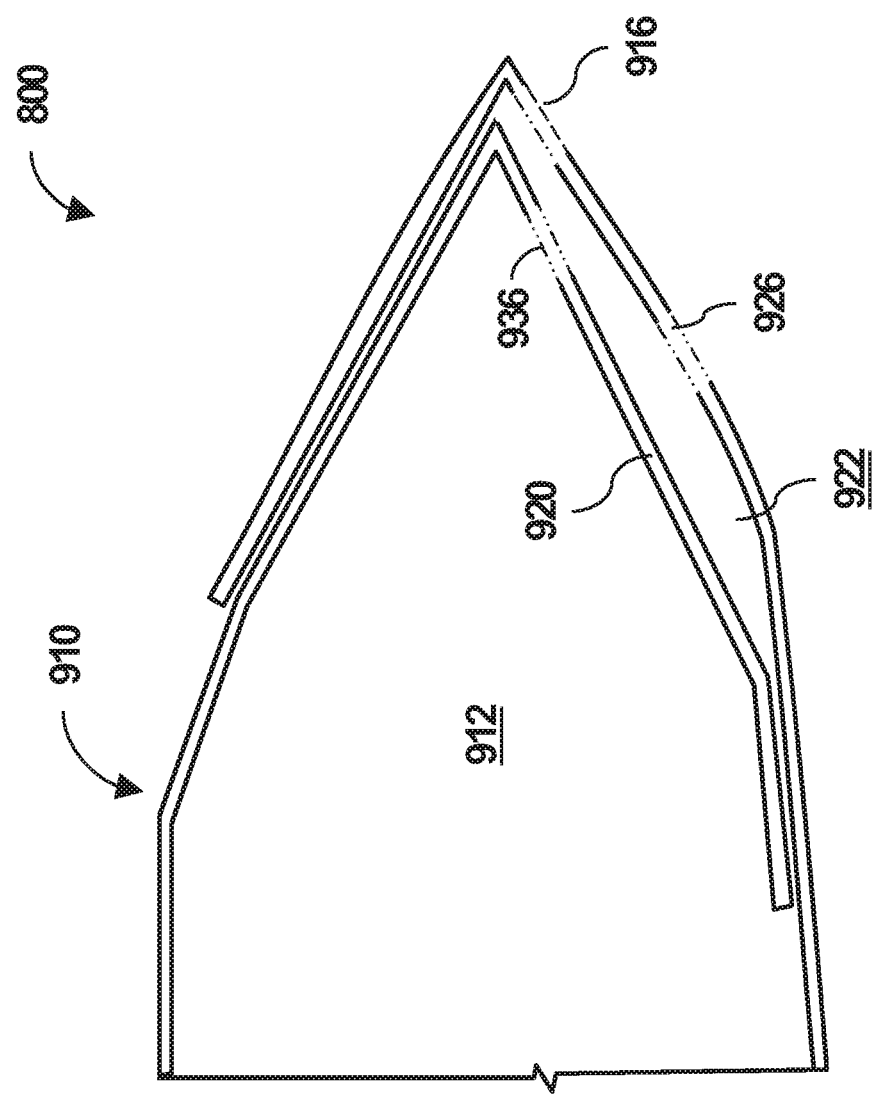
FIG. 9 is a longitudinal cross-sectional view of the medication inhalation apparatus in an expanded state, in accordance with the fourth exemplary embodiment of the present disclosure.

FIG. 9 is a longitudinal cross-sectional view of the medication inhalation apparatus 800 in an expanded state, in accordance with the fourth exemplary embodiment of the present disclosure. The expanded apparatus 800 may be discussed relative to FIGS. 1A-1B and 8A-8C. For ease of illustration, FIG. 9 shows only a portion of the expanded apparatus 800; the portion not shown, which includes the outer boot adapter panel 832A, B and inner boot adapter panel 830A, may be understood with reference to the analogous elements of FIGS. 1A-1B. It should also be understood that FIG. 9 shows folded portions of the apparatus 800 separated by a small distance. This is shown for ease of illustration only; in construction, layers of the sheet 801 folded together will be in contact with one another by adhesive or by biased force.

The apparatus 800 includes an outer housing 910 collapsible into a substantially flat configuration and expandable to bound a first volume 912 adapted to receive a plume of medication particles ejected by an MDI inhaler. An inner flap 920 is located within the outer housing 910 and, together with the outer housing 910, is expandable to bound a second volume 922 within the outer housing. A first opening, elongated inhaler opening 814 shown in FIG. 8A, is formed through a wall of the outer housing 910 at a first location in fluid communication with the first volume 912. The first opening 814 is adapted to accommodate a mouthpiece of an MDI inhaler (not shown). A second opening 916 is formed through a wall of the outer housing 910 at a second location adapted to form a user mouth opening in fluid communication with the second volume 922. A one-way inhalation valve 936 is located within the inner flap 920. The inhalation valve 936 connects the first volume 912 and the second volume 922. A one-way exhalation valve 926 is located within a wall of the outer housing 910. The exhalation valve 926 connects the second volume 922 and the exterior of the outer housing 910. In an expanded state, gas is flowable from a connected MDI to the first volume 912, from the first volume 912 to the second volume 922, and from the second volume 922 to the mouth of a user.

The outer housing 910 may be formed as described above using the top and bottom sections 830, 802. In a collapsed state, the outer housing 910 may be substantially flat, having the thickness of a few layers of the sheet 801. In an expanded state, the outer housing 910 may bound a first volume 912. The first volume 912 may be defined by the interior of the outer housing 910 and the inner flap 920. In use, the first volume 912 may be a chamber for holding medication particles sprayed from a connected MDI. The gas in the first volume 912 may remain in the first volume 912 until the user inhales the gas.

The inner flap 920 is located within the outer housing 910. The inner flap 920 extends between the top and bottom panels 830B, 802B and between side panels 847A, B and 880A, B. When the apparatus 800 is expanded, the inner flap 920 rises from a flattened configuration to a partially raised configuration, as shown in FIG. 9. When the inner flap 920 is partially raised, it creates a second volume 922 within the outer housing 910 bounded by the interior of the outer housing 910 and the inner flap 920. The second volume 922 is an intermediate volume between the first volume 912 and a user's mouth, and the user may inhale or exhale through the second volume 922 in order to receive the medication particles located in the first volume 912 or to clear the user's lungs of air before receiving the medication particles.

The first opening, which is shown in FIG. 8A as elongated inhaler opening 814, is expandable to receive an MDI inhaler. This is discussed in greater detail relative to FIG. 1A.

The second opening 916 is formed on the outer housing 910. A user may place their mouth over the second opening 916 and may inhale or exhale through the second opening 916. As discussed above, the second opening 916 may include one or more openings, such as circular openings 872, and may generally be located in close proximity to scored fold line 857. The second opening 916 may be any size, shape, or configuration of openings suitable to allow the user to inhale and exhale at sufficient flow rates through the apparatus 800. The second opening 916 is in fluid communication with the second volume 922 to allow gas to flow from the second volume 922 to the user's mouth or from the user's mouth to the exterior of the apparatus 800.

The one-way inhalation valve 936 is located on the inner flap 920. As shown in FIG. 8B, the inhalation valve 936 may include one or more openings 890 of any suitable shape, size, and configuration to allow gas to travel from the first volume 912 to the second volume 922. As described relative to FIG. 1B above, the inhalation valve 936 may include a flexible membrane (not shown) lying flat against the inner flap 920 over the one or more openings 890. The flexible membrane may flex away from the first volume 912 when a user inhales in order to allow gas from the first volume 912 to flow from the first volume 912 to the second volume 922. When the user exhales, the flexible membrane may remain flat against the inner flap 920 to cover the one or more openings 890.

The one-way exhalation valve 926 may be located on the outer housing 910 and may operate under the same principle as the inhalation valve 936. The bottom panel 802B may have one or more exhalation valve openings 873, which may be any suitable size, shape, and configuration to allow air to pass out of the apparatus 800. The exhalation valve 926 may include a flexible membrane (not shown) lying flat against the exterior side of the bottom panel 802B. The flexible membrane may flex away from the apparatus 800 when a user exhales, allowing air from the user's lungs and mouth to escape out of the apparatus. When the user inhales, the flexible membrane may remain flat against the bottom panel 802B, preventing exterior air from entering the second volume 922.

It should be noted that the one-way inhalation and exhalation valves 936, 926 may be made from any suitable materials, including plastic, paper, wood, polymer, and the like.

In use, a user may expand the apparatus 800 from its flattened state by pressing the sides of the apparatus 800, causing the top panel 830B to rise and the apparatus 800 to expand. The user may attach an MDI device to the apparatus 800. The user may press on the MDI device to release the medicine into the first volume 912. The user may place their mouth of the second opening 916 and may exhale through the second opening 916, into the second volume 922, and out the exhalation valve 926. The user may inhale, causing the medicine to travel from the first volume 912 to the second volume 922 through the inhalation valve 936, then into the user's mouth through the second opening 916.

The design relies on the tension created by mismatched geometry. When the apparatus 800 is flattened, the perforation lines 880E, 847E of the bottom panel 802B and the cut score splines 891A, B on the inner flap 879 line up, and the apparatus 800 is flat. When the apparatus 800 is expanded, the sides of the inner flap 879 stay glued to the sides of the bottom panel 802B and remain at the same height as the sides. Additionally, this causes the first volume 912 to be substantially larger than previously known designs, which may improve the holding capabilities of the first volume 912.

Figure 10:
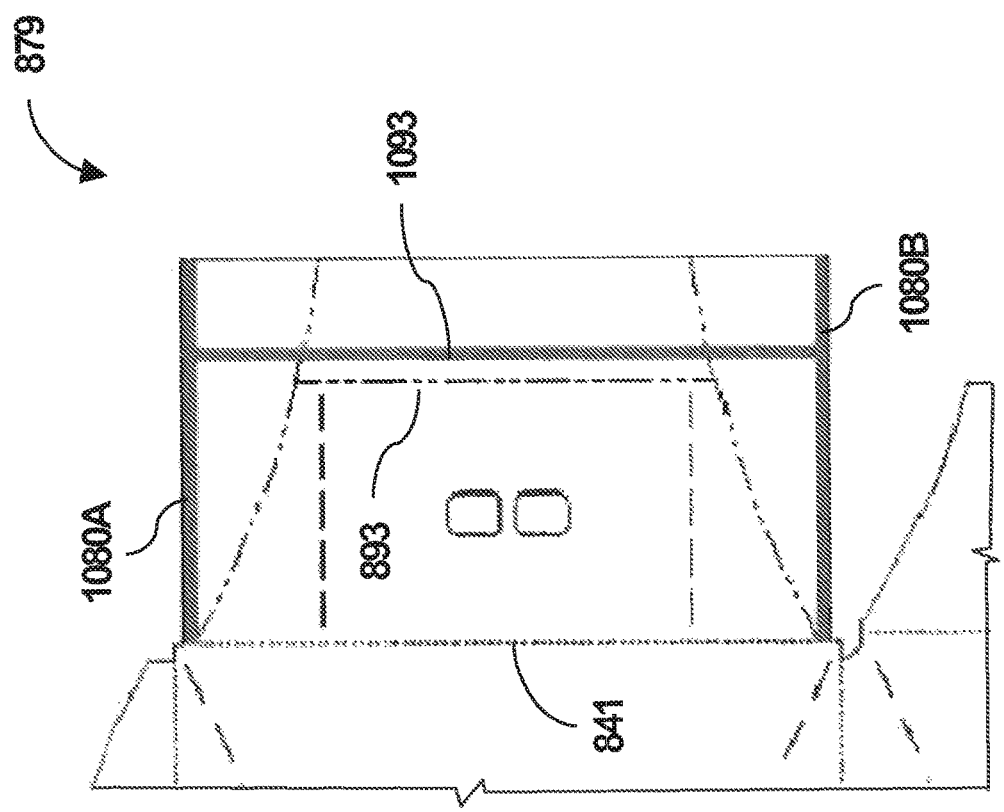
FIG. 10 is a close-up plan view of a glue pattern of the inner flap shown in FIG. 8B, in accordance with the fourth exemplary embodiment of the present disclosure.

FIG. 10 is a close-up plan view of a glue pattern of the inner flap 879 shown in FIG. 8B, in accordance with the fourth exemplary embodiment of the present disclosure. Glue or other adhesive may be applied to the inner flap 879 or to the equivalent location on the bottom panel 802B in an "H" pattern before the inner flap 879 is folded over. The glue "H" pattern shown in FIG. 10 is an exemplary pattern showing the minimum locations where glue or adhesive may be applied in order to create a proper seal between the first volume, the second volume, and the outer housing. More glue lines may be applied as long as the pattern shown herein is also followed. Additionally, depending on the manufacture, the glue "H" pattern shown herein may be applied as a series of lines, broken lines, dots, and the like, as long as the glue or adhesive is applied to substantially seal along the entire adhesive lines.

The sheet 801 may be printed and die cut. Valve holes may be cut, and the valves may be assembled as discussed above. Lines 1080A, 1080B, and 1093 may be located on the underside of the inner flap 879. They are shown with reference to the topside of inner flap 879 for ease of illustration. However, it should be understood that the adhesive or glue may be applied as an "H" pattern so as to adhere the underside of the inner flap 879 to the bottom panel 802B of the apparatus 800. The glue or adhesive may be applied along lines 1080A, 1080B, and 1093, or along the equivalent locations on bottom panel 802B. Either before or after application, the inner flap 879 may be folded over onto the top panel 830B. The bottom panel 802B may be folded onto the inner flap 879 such that the inner flap 879 is sandwiched between the top and bottom panels 830B, 802B. The rest of the apparatus 800 may be folded as described above.

Operational Examples

The usefulness of the design is readily apparent from the backflow readings taken on the apparatus 800. The apparatus 800 delivered roughly 0.15 L/min of backflow without pinching the sides of the apparatus 800, which is a significant improvement over prior devices. Backflow is a decent predictor of the ability of the apparatus 800 to mitigate a user's inability to inhale at the same time as pMDI actuation, which is one of the major functions of a VHC. This improvement also runs hand in hand with decreased complexity in manufacturing compared with the apparatus 100 shown in FIGS. 1A-1B and 2. The folding process may use mountain and valley folds, which are routinely performed on folder/gluers. The ability to entirely perform the folding and gluing of the apparatus 800 on a folder/gluer means that the cost of manufacture can be lowered and the speed of production can be increased.

Figure 11:
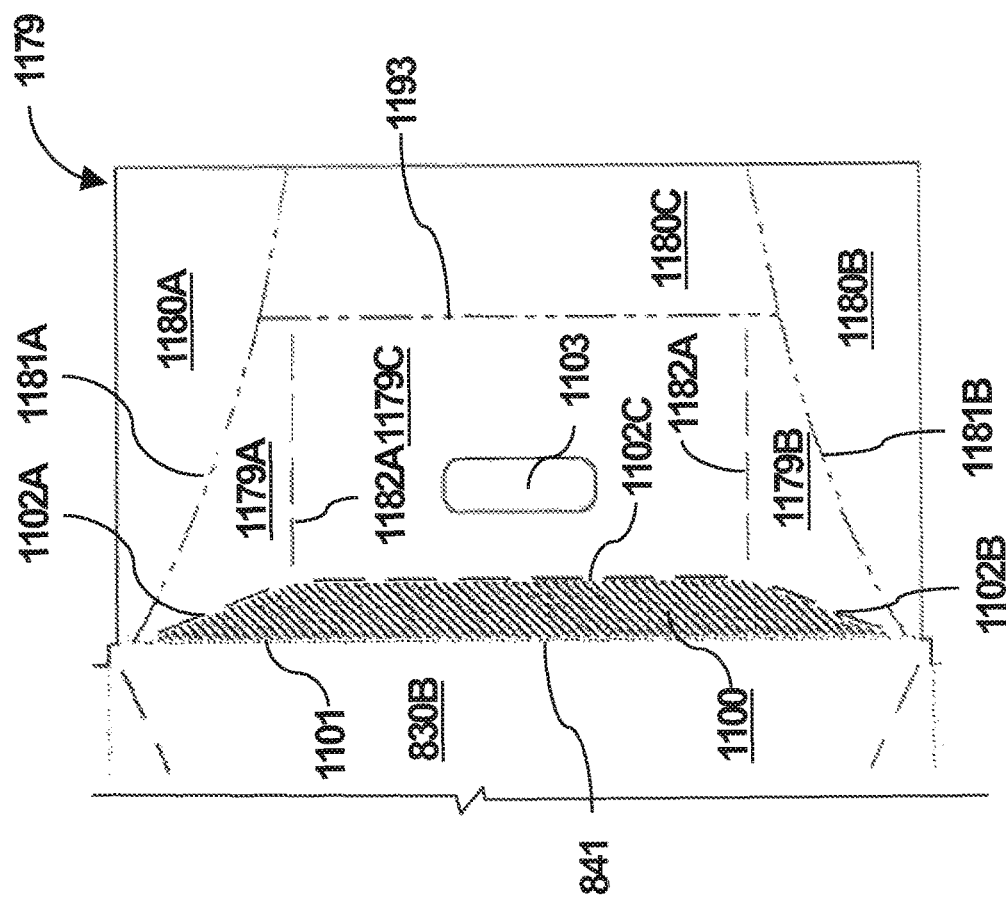
FIG. 11 is a close-up plan view of an inner flap for use in conjunction with the sheet shown in FIG. 8A, in accordance with a fifth exemplary embodiment of the present disclosure.

FIG. 11 is a close-up plan view of an inner flap 1179 for use in conjunction with the sheet 801 shown in FIG. 8A, in accordance with a fifth exemplary embodiment of the present disclosure. The inner flap 1179 may increase the size of the second volume 922 in FIG. 9 relative to the inner flap 879 shown in FIG. 8A. The inner flap 1179 may include left outer panel 1180A connected to left inner panel 1179A across skip scored fold line 1181A. Likewise, right outer panel 1180B may be connected to left inner panel 1179B across skip scored fold line 1181B. Center outer panel 1180C is connected to center middle panel 1179C across skip scored fold line 1193. Center middle panel 1179C may include one or more valve openings 1103 located on the center middle panel 1179C. Center middle panel 1179C may be connected to center inner panel 1100 across straight skip scored line 1102C. Center inner panel 1100 may be connected to top panel 830B across fold line 841 and may extend substantially across a width of the inner flap 1179.

The inner flap 1179 shown in FIG. 11 may improve airflow through the apparatus 800 in cases where a user is likely to bite down on the apparatus 800 in use. In the embodiment shown in FIGS. 8A-9, the inner flap 879 is located in close proximity to the outer housing 910 in the expanded state. In the embodiment shown in FIG. 11, the inner flap 1179 may be glued to the top panel 830B at the center inner panel 1100. The center inner panel 1100 may act as an adhesive panel, securing a portion of the inner flap 1179 to the top panel 830B. This may cause the inner flap 1179 to be oriented more vertically in an expanded state than the inner flap 879 in FIGS. 8A-9, which in turn may create more space in the second volume 922.

Figure 12A:
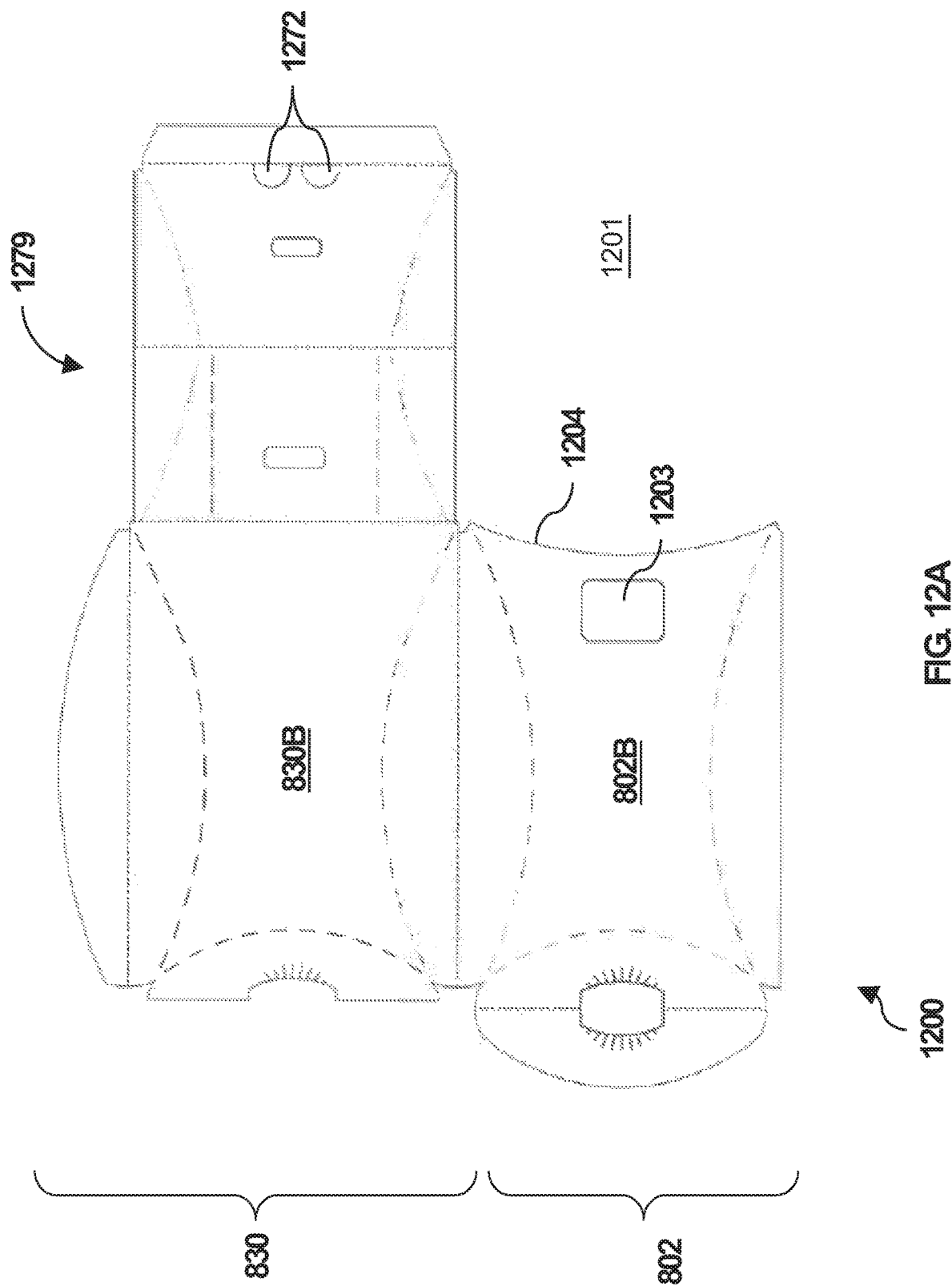
FIG. 12A is a plan view of a sheet from which a medication inhalation apparatus is constructed, in accordance with a sixth exemplary embodiment of the present disclosure.

FIG. 12A is a plan view of a sheet 1200 from which a medication inhalation apparatus 1201 is constructed, in accordance with a sixth exemplary embodiment of the present disclosure. In one example, the sheet 1200 may be include substantially the same component panels and fold lines as the sheet 801 shown in FIG. 8A, above. This may include top and bottom sections 830, 802 having top and bottom panels 830B, 802B, respectively. For ease of illustration, not all of the component panels and fold lines are given reference characters in FIG. 12A. It should be understood that except as described below, the components of the sheet 1200 are substantially the same as sheet 801 above.

Sheet 1200 may include an inner flap 1279 for creating a separate, sealed mouthpiece chamber. This is discussed in greater detail in FIG. 12B, below.

In one example, sheet 1200 may not include an outer flap, such as outer flap 871 shown in FIG. 8A. In this example, bottom panel 802B may be folded over inner flap 1279 and adhered directly to inner flap 1279. Bottom panel 802B may be arcuate along edge 1204 so as not to cover circular openings 1272 on the inner flap 1279, which allow the user to exhale into and inhale out of the apparatus 1201 in an expanded state. Bottom panel 802B may also include one or more valve openings 1203 that covers the adhesive panel of the valve, while still allowing the free edge to open freely. Any suitable shape, number and size of valve openings 1203 may be used.

Figure 12B:
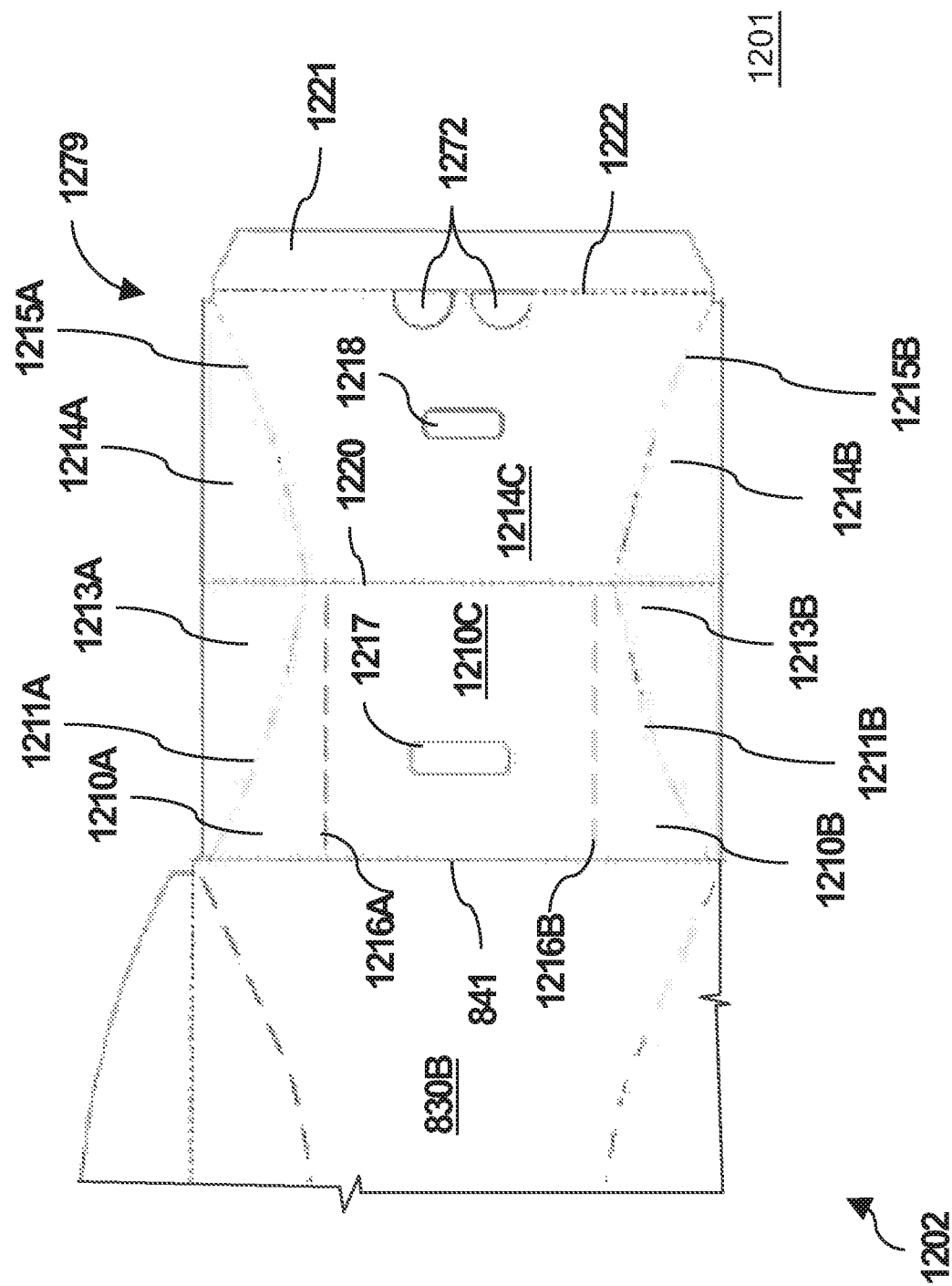
FIG. 12B is a close-up plan view of an inner flap for creating a separate mouthpiece chamber, in accordance with the sixth exemplary embodiment of the present disclosure.

FIG. 12B is a close-up plan view of an inner flap 1279 for creating a separate mouthpiece chamber 1202, in accordance with the sixth exemplary embodiment of the present disclosure. The mouthpiece chamber 1202, which may create a second volume when assembled and in an expanded state, may be a sealed chamber around which the rest of the apparatus 1201 is folded. This may improve the seal between the first volume and the second volume within the apparatus 800.

The inner flap 1279 may include left central panels 1210A and 1213A connected across cut scored line 1211A. Left central panel 1210A may be connected to central panel 1210C across skip scored fold line 1216A. Likewise, right central panels 1210B and 1213B may be connected across cut scored line 1211B. Right central panel 1210B may be connected to central panel 1210C across skip scored fold line 1216B. Central panel 1210C may include one or more valve openings 1217 located on the central panel 1210C. Left, right, and central panels 1210A, 1210B, 1210C may be connected to top panel 830B across fold line 841.

The central panels above may be connected to outer panels 1214A, 1214B, 1214C across fold line 1220, which may extend across the width of the inner flap 1279. Left outer panel 1214A and right outer panel 1214B may be connected to central panel 1214C across arcuate cut scored fold lines 1215A, 1215B, respectively. Central panel 1214C may include one or more valve openings 1218 located to align with valve opening 1203 when the apparatus 1201 is in an expanded state. Valve opening(s) 1218 may allow air to travel from the second volume, i.e., the mouthpiece chamber 1202, to the exterior of the apparatus 1201. Central panel 1214C may also include one or more circular openings 1272 to allow a user to breathe into or breathe from the apparatus 1201. The circular openings 1272 may allow air to flow between the second volume and the user's mouth.

Central panel 1214C may be connected to edge panel 1221 across fold line 1222, which may extend across the entire width of the inner flap 1279.

The apparatus 1201 may be assembled by folding the inner flap 1279 along line 841 on top of the top panel 830B. The outer panels may be folded back along line 1220, and the edge panel 1221 may be folded back along line 1222 to rest on the underside of the top panel 830B. Adhesive may be applied to the edge panel 1221 and to panels 1213A, 1213B, 1214A, 1214B. Bottom panel 802B may be folded over against top panel 830B, and the left side panel and adhesive side panel may be glued and attached as described above. The top of bottom panel 802B may be glued to the outer panels near the circular openings 1272. The boot adapter panels may be glued and attached as described above as well.

When in an expanded state, the apparatus 1201 may include an outer housing formed by the top and bottom sections 830, 802. The outer housing may be collapsible into a substantially flat configuration and expandable to bound a first volume adapted to receive a plume of medication particles ejected by an MDI inhaler. The inner flap 1279 may be located within the outer housing and may be expandable to bound a second volume within the outer housing. An edge panel 1221 of the inner flap 1279 may be adhesively affixed to a portion of the outer housing to secure the second volume. A first opening may be formed through a wall of the outer housing at a first location. The first opening may be in fluid communication with the first volume, and may be adapted to accommodate a mouthpiece of an MDI inhaler. A second opening may be formed through a wall of the outer housing at a second location and may be adapted to form a user mouth opening in fluid communication with the second volume. A one-way inhalation valve may be located within a central panel of the inner flap and may connect the first volume and the second volume. A one-way exhalation valve may be located within an outer panel of the inner flap and a wall of the outer housing. The one-way exhalation valve may connect the second volume and an exterior of the outer housing. In an expanded state, gas is flowable from a connected MDI to the first volume, from the first volume to the second volume, and from the second volume to the mouth of a user.

The separate mouthpiece chamber 1202 may improve over the art in at least two ways. In a first way, the apparatus 1201 may increase protection for the exhalation valve by providing a protective layer around valve opening 1203. The protective layer, which may essentially be the portion of the bottom panel 802B located around the valve opening 1203, may allow the exhalation valve to be recessed into the apparatus 1201. This extra layer allows the glue line of the exhalation valve to be covered and protected, and it also gives the free edge of the exhalation valve increased protection from being accidentally snagged when the apparatus 1201 is slid against other surfaces. In a second way, the application of adhesive is simplified compared to what is known in the art. Since the back of the mouthpiece is formed by a score line 1220, which blocks airflow, the only glue lines required to seal the mouthpiece chamber 1202 are the two glue lines on the side of the mouthpiece chamber 1202. This simplifies the glue pattern immensely since the gluing to form a sealed mouthpiece is no longer dependent on gluing with perpendicular glue lines, which can be difficult to perform on a folder/gluer.

FIG. 13 is a flowchart 1300 describing a method of expanding a medication inhalation apparatus from an initially flat, collapsed state, in accordance with a first embodiment of the present disclosure. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

In step 1310, an outer housing, an inner flap positioned within the outer housing, wherein the outer housing and the inner flap are substantially airtight when expanded, an inhaler opening formed at least partially within a sidewall of the outer housing at a first location, a mouth opening positioned within a sidewall of the outer housing at a second location, a one-way inhalation valve positioned within a sidewall of the inner flap, and a one-way exhalation valve positioned within a sidewall of the outer housing at a third location are provided in the collapsed state.

In step 1320, a pair of opposite sidewall panels on the outer housing is pressed.

In step 1330, the outer housing and inner flap are manually expanded to create a first volume encompassed by the outer housing and an second volume encompassed by the inner flap and the outer housing, wherein the inhaler opening is in fluid communication with the first volume, wherein the mouth opening is in fluid communication with the second volume, wherein the inhalation valve connects the first volume and the second volume, wherein the exhalation valve connects the second volume and the exterior of the outer housing, and wherein gas is flowable from the metered dose inhaler to the first volume, from the first volume to the second volume, and from the second volume to the mouth of a user.

Figure 14:
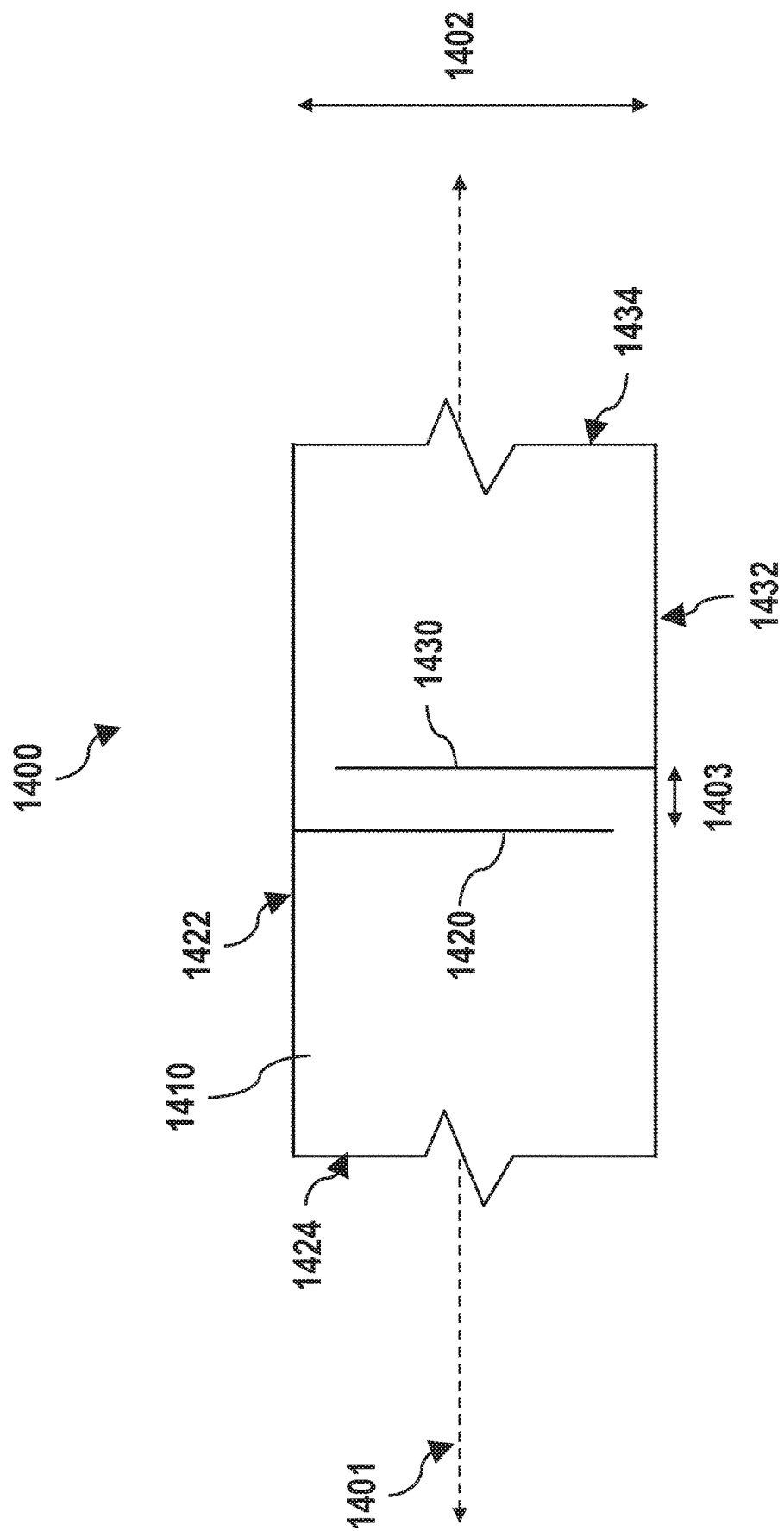
FIG. 14 is a plan view of a spring, in accordance with a seventh exemplary embodiment of the present disclosure.

FIG. 14 is a plan view of a spring 1400, in accordance with a seventh exemplary embodiment of the present disclosure. The spring 1400 includes a spring body 1410 formed of a semi-pliant material with a strength and rigidity providing limited flexibility. The spring body 1410 has an elongate axis 1401. A first separation 1420 is perpendicular to the elongate axis 1401 of the spring body 1410. The first separation 1420 extends from a first edge 1422 of the spring body 1410 across at least a portion of a width 1402 of the spring body 1410. A second separation 1430 is perpendicular to the elongate axis 1401 of the spring body 1410. The second separation 1430 extends from a second edge 1432 of the spring body 1410 across at least a portion of the width 1402 of the spring body 1410.

The spring body 1410 may be a flat, planar body formed using any of the materials discussed above, including plastic, paper, wood, polymer, paperboard, and the like. The material may be semi-pliant with strength and rigidity across the plane of the spring body 1410. The strength and rigidity may provide limited flexibility to the spring body 1410 such that the body itself may not be particularly flexible. The spring body 1410 may have an elongate axis 1401 extending across a length of the spring body 1410. In one example, the spring body 1410 may be longer along the elongate axis 1401 than in any other dimension. In a particular example, the spring body 1410 may be rectangular in shape, with the longer sides parallel to the elongate axis 1401.

A first separation 1420 may be perpendicular to the elongate axis 1401. The axis perpendicular to the elongate axis 1401 may define a width 1402 of the spring body 1410, which may, in some examples, be shorter than the length of the spring body 1410. The first separation 1420 may be a separation in the material of the spring body 1410, which may be formed by any of the methods described above, including laser cutting, die cutting, and chemical etching, among others. The thickness of the first separation 1420 may depend on the application. In one example, the first separation 1420 may be a narrow separation of less than the thickness of the spring body 1410 material. In another example, the first separation 1420 may be a wider separation. The first separation 1420 may extend from a first edge 1422 of the spring body 1410. The first edge 1422 may be parallel to the elongate axis 1401. The first separation 1420 may extend from the first edge 1422 across a portion of the width 1402 of the spring body 1410. In one example, the first separation 1420 may extend across at least half of the width 1402. In another example, the first separation 1420 may extend across a substantial portion of the width 1402 of the spring body 1410. The first separation 1420 may, in one example, be a substantially straight line. In another example, the first separation 1420 may be an angled, curved, or undulating line.

A second separation 1430 may be perpendicular to the elongate axis 1401 and parallel to the width 1402 of the spring body 1410. The second separation 1430 may include any of the characteristics discussed relative to the first separation 1420, above. The second separation 1430 may extend from a second edge 1432 of the spring body 1410. The second edge 1432 may be opposite from and parallel to the first edge 1422. The second separation 1430 may extend across at least a portion of the width 1402 of the spring body 1410. In one example, the second separation 1430 may extend across at least half of the width 1402. In another example, the second separation 1430 may extend across a substantial portion of the width 1402 of the spring body 1410.

In one example, the first and second separations 1420, 1430 may be the same length and thickness. In another example, the first and second separations 1420, 1430 may have different lengths and/or thicknesses relative to one another. This may depend on how the spring 1400 is employed in use. For instance, if an end of the spring 1400 nearer to the first separation 1420 is in communication with a hinge, while the end of the spring 1400 nearer to the second separation 1430 is in communication with an anchored flap, this may require different levels of spring return, necessitating different lengths and widths of the separations 1420, 1430.

The first and second separations 1420, 1430 may extend through at least a portion of the thickness of the spring body 1410. In one example, the first and second separations 1420, 1430 may extend through the entire thickness of the spring body 1410, i.e., as a cut or a total separation of the spring body material. In another example, the first and second separations 1420, 1430 may only extend through a portion of the spring body 1410, i.e., as a score line or indentation. The first and second separations 1420, 1430 may each extend to a different degree through the thickness of the spring body 1410. For instance, the first separation 1420 may extend entirely through the spring body 1410, while the second separation 1430 may extend partially through the spring body 1410. This may depend on the operation of the spring 1400.

The first and second separations 1420, 1430 may be spaced apart by a spaced distance 1403. The spaced distance 1403 may be any suitable distance, depending on the operation of the spring 1400. In one example, the spaced distance 1403 may be less than a length of the first and second separations 1420, 1430. In one particular example, the spaced distance 1403 may be substantially less than the length of the first and second separations 1420, 1430. The length of the spaced distance 1403 may affect the load under which the spring 1400 may perform. A shorter spaced distance 1403 may reduce the spring return, while a larger spaced distance 1403 may increase the spring return. This may depend upon the rigidity and other characteristics of the spring body 1410 material.

The spring 1400 may operate by torsion. A first end 1424 or second end 1434 of the spring 1400 may be bent orthogonal to the face of the spring body 1410 this may cause the spring body 1410 to bend at the first and second separations 1420, 1430. The portion of the spring 1400 within the spaced distance 1403 may be twisted, which may cause tension in the spring body 1410. Once the force causing the first or second ends 1424, 1434 has been removed from the spring 1400, the tension in the spaced distance 1403 may cause the first or second ends 1424, 1434 to return to their original positions. In one aspect, this may provide a mechanism to limit the distance the first or second ends 1424, 1434 may travel. The torsion in the spaced distance 1403 may provide resistance to the first or second ends 1424, 1434, which may limit travel.

The operation of the spring 1400 by torsion is novel in light of planar springs known in the art. Planar springs provide spring force only along the plane in which the spring is made, and not perpendicular to that plane. Thus the principle of operation known in the art is not torsion of the supportive beams of the spring, but a different planar force.

The spring 1400 may be used in a number of operations. In one example, the spring 1400 may be used in conjunction with a valve, such as the one-way inhalation valve 124 or the one-way exhalation valve 126 described relative to FIGS. 1A-1B, above. The spring 1400 may allow the valve to return to its original position after air is drawn through the opening covered by the valve. In one example, when the spring 1400 is used with a valve, at least one living hinge may be included to assist in the movement of the valve. This is discussed in greater detail in FIG. 16, below.

Figure 15:
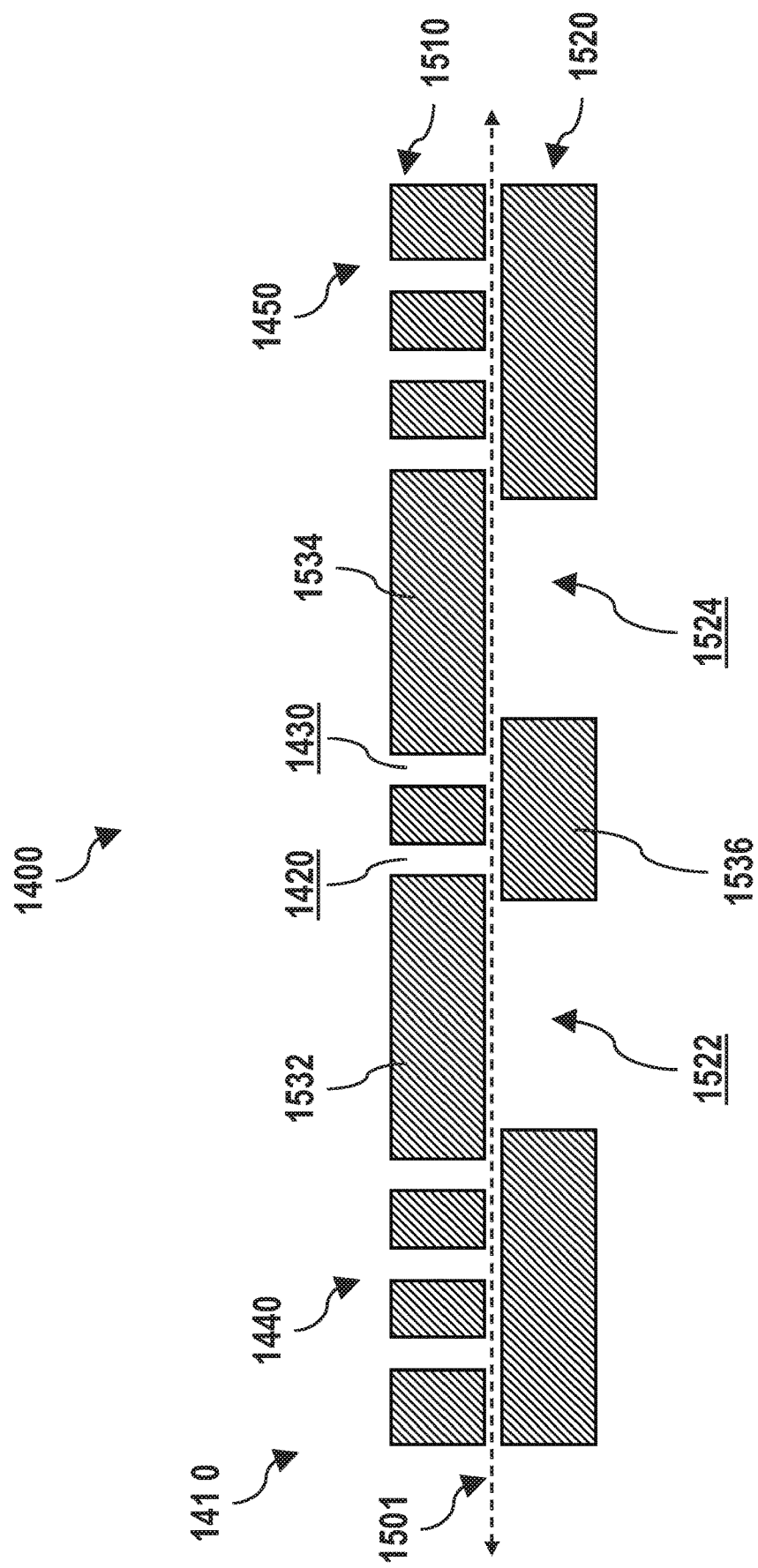
FIG. 15 is a cross-sectional diagrammatic view of the spring of FIG. 14, in accordance with the seventh exemplary embodiment of the present disclosure.

FIG. 15 is a cross-sectional diagrammatic view of the spring 1400 of FIG. 14, in accordance with the seventh exemplary embodiment of the present disclosure. The spring 1400 may include the spring body 1410, first separation 1420, and second separation 1430, as discussed above.

In one example, the spring body 1410 may have a single layer, which may be a first layer 1510. In another example, the spring body 1410 may include a first layer 1510 and a second layer 1520. The first layer 1510 may be formed from the semi-pliant material and may be sized and shaped as described above. The first layer 1510 may comprise the first and second separations 1420, 1430, which may extend through at least a portion of the thickness of the first layer 1510. In one example, the first and second separations 1420, 1430 may extend through the entire thickness of the first layer 1510.

In one example, the first layer 1510 may further include at least one living hinge 1440, 1450. For purposes of illustration, FIG. 15 shows a first living hinge 1440 located on a first side of the first and second separations 1420, 1430 and a second living hinge 1450 located on a second side of the first and second separations 1420, 1430. It should be understood that the spring 1400 may be used with one living hinge 1440 on any side of the first and second separations 1420, 1430. The living hinges 1440, 1450 are described in additional detail below. They may be formed through at least a portion of the thickness of the first layer 1510, and may operate in conjunction with the other elements of the spring 1400, for instance, when used to operate a valve.

The first layer 1510 may be affixed to the second layer 1520 along a plane 1501 extending along the elongate axis 1401. The plane 1501 may be orthogonal to the thickness of the first and second layers 1510, 1520. The first and second layers 1510, 1520 may be affixed using any suitable methods, including glues, epoxies, and other adhesives, as well as bonding methods suitable for planar materials as described herein. In one example, additional layers may be included above or below the first and second layers 1510, 1520, depending on the application of the spring 1400.

The second layer 1520 may be formed from the semi-pliant material and may generally be sized and shaped to accommodate the first layer 1510. In one example, the second layer 1520 may be the same size and shape as the first layer 1510. The second layer 1520 may include at least one cutout 1522 adjacent to the first and second separations 1420, 1430. The at least one cutout 1522 may be a portion of the second layer 1520 wherein the material has been removed. This may be accomplished by any of the methods described above, including die-cutting, laser removal, and the like. The at least one cutout 1522 may extend across at least a portion of the width of the second layer 1520. This is shown in greater detail in FIG. 16, below. The at least one cutout 1522 may have a length along the elongate axis 1401 that is longer than the first and second separations 1420, 1430.

In one example, the at least one cutout 1522 may be located within the second layer 1520 between a living hinge 1440 and the first separation 1420. The at least one cutout 1522 may have a length substantially the distance between the living hinge 1440 and the first separation 1420, i.e., the second layer 1520 may be substantially cut out between the living hinge 1440 and the first separation 1420. Where two living hinges 1440, 1450 are employed, two cutouts 1522, 1524 may be located between the first and second separations 1420, 1430 and the living hinges 1440, 1450. This may allow the spring body 1410 to maintain rigidity while utilizing the flexibility of the hinges 1440, 1450 and the spring return. The cutouts 1522, 1524 may be aligned and correspond with the rigid, uncut sections 1532, 1534 of the first layer 1510. In this example, the first and second layers 1510, 1520 may be glued or bonded together where the uncut sections 1532, 1534, 1536 overlap. This may prevent air or other gas from passing through any gaps in the layers 1510, 1520.

Figure 16:
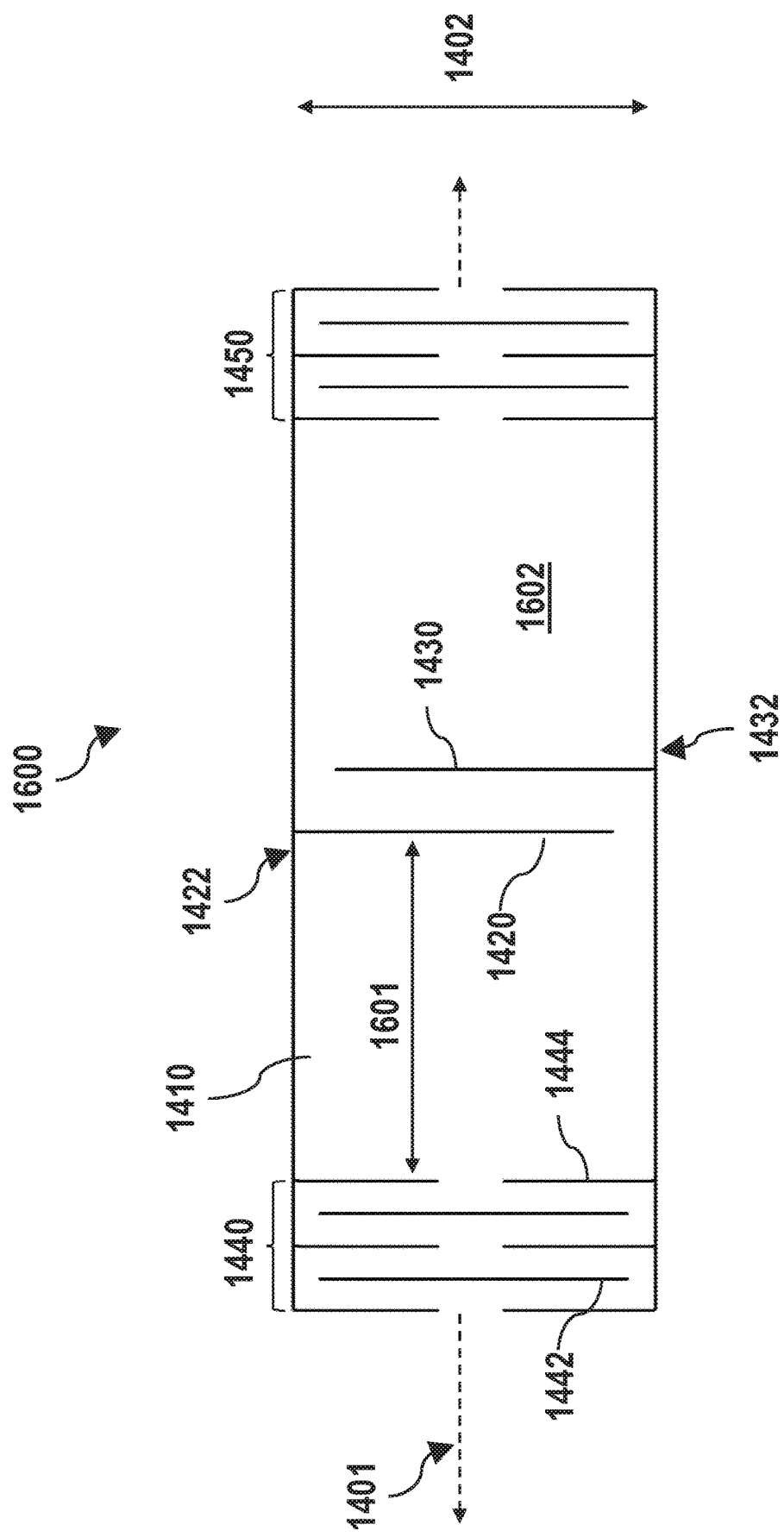
FIG. 16 is a plan view of a valve flap with a spring return, in accordance with the seventh exemplary embodiment of the present disclosure.

FIG. 16 is a plan view of a valve flap 1600 with a spring return, in accordance with the seventh exemplary embodiment of the present disclosure. The valve flap 1600 includes a spring body 1410 formed of a semi-pliant material with a strength and rigidity providing limited flexibility. The spring body 1410 has an elongate axis 1401. A first separation 1420 is perpendicular to the elongate axis 1401 of the spring body 1410. The first separation 1420 extends from a first edge 1422 of the spring body 1410 across at least a portion of a width 1402 of the spring body 1410. A second separation 1430 is perpendicular to the elongate axis 1401 of the spring body 1410. The second separation 1430 extends from a second edge 1432 of the spring body 1410 across at least a portion of the width 1402 of the spring body 1410. A living hinge 1440 is formed in the spring body 1410 and located a spaced distance 1601 from the first and second separations 1420, 1430. An uncut section 1602 is located in the spaced distance 1601 between the living hinge 1440 and the first and second separations 1420, 1430. The uncut section 1602 is positionable to prevent the flow of gas through a valve opening.

The spring body 1410 and first and second separations 1420, 1430 may be as described above relative to FIGS. 14-15. They may be sized, shaped, positioned, and manufactured according to the same parameters. In one example, the spring body 1410 may include first and second layers, as discussed in FIG. 15, wherein the first and second separations 1420, 1430 are located within the first layer, and the at least one cutout is located within the second layer.

The valve flap 1600 may include a living hinge 1440. In one example, the valve flap 1600 may include two living hinges 1440, 1450. The living hinges 1440, 1450 may be hinges formed from separations in the spring body 1410. This may include a plurality of central separations 1442 disposed between a plurality of edge separations 1444. That is, one central separation 1442 may be adjacent to an edge separation 1444, which may be adjacent to a central separation 1442, and so on. The central and edge separations 1442, 1444 may be cuts or scores made as described above. The central separations may extend perpendicular to the elongate axis 1401 of the spring body 1410. They may extend across a center of the width 1402 of the spring body 1410, that is, they may not extend from the edges 1422, 1432 of the spring body 1410. The edge separations 1444 may extend perpendicular to the elongate axis 1401 of the spring body 1410 from the first and second edges 1422, 1432 of the spring body 1410. The edge separations 1444 may extend from both edges 1422, 1432 without meeting in the center of the spring body 1410.

The living hinge 1440 may be located a spaced distance 1601 from the first and second separations 1420, 1430. It may be understood that when there are multiple living hinges 1440, 1450, each may be located a spaced distance 1601 apart from the separations 1420, 1430. In particular, the first living hinge 1440 may be located a spaced distance 1601 apart from the first separation 1420, while the second living hinge 1450 may be located a spaced distance 1601 apart from the second separation 1430. The spaced distance 1601 may be measured along the elongate axis 1401. In one example, the spaced distance 1601 between the first living hinge 1440 and the separations 1420, 1430 may be different from the spaced distance 1601 between the second living hinge 1450 and the separations 1420, 1430.

An uncut section 1602 is located in the spaced distance 1601 between the living hinge 1440 and the first and second separations 1420, 1430. The uncut section 1602 may be a portion of the spring body 1410 without cuts, grooves, or score lines. The uncut section 1602 is positionable to prevent the flow of gas through a valve opening. In other words, the uncut section 1602 may act as a barrier to gas, including air and medicament. When in use, the uncut section 1602 may provide a substantially airtight seal or may allow the flow of gas, depending on whether the valve flap 1600 is in a closed position or an open position. The valve flap 1600 may be used with any valve configuration discussed relative to FIGS. 1A-15, above.

Figure 17:
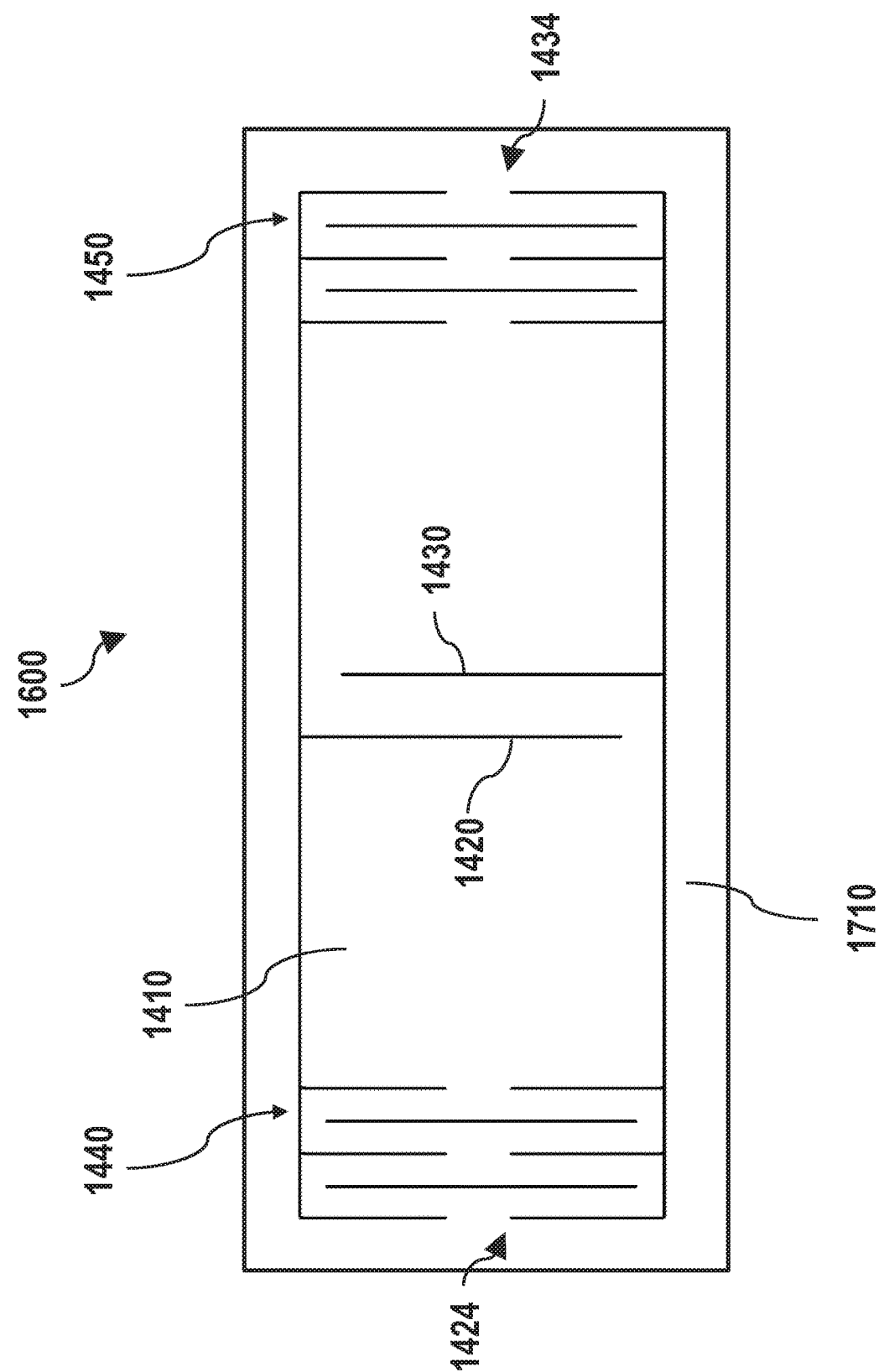
FIG. 17 is a plan view of the valve flap of FIG. 16 in use with a valve surface.

FIG. 17 is a plan view of the valve flap 1600 of FIG. 16 in use with a valve surface 1710. The living hinges 1440, 1450 may be located near first and second ends 1424, 1434 of the spring body 1410, respectively. First end 1424 may be affixed to a valve surface 1710, which may be any surface in proximity to a valve opening as described relative to any figures herein. Second end 1434 may be affixed to the valve surface 1710 as well. In one example, the spring body 1410 may be manufactured as a monolithic or unitary piece with the valve surface 1710. That is, the spring body 1410 and the valve surface 1710 may be made from the same piece of material rather than being bonded or affixed using adhesive. One or more valve openings may be located underneath the uncut sections 1602 shown in FIG. 16. In operation, the valve flap 1600 may alternate between a closed position, wherein the uncut sections 1602 lie against a valve opening to prevent the flow of gas through the valve opening, and an open position, wherein the uncut sections 1602 are spaced away from the valve opening to allow the flow of gas through the valve opening. When air is applied to the valve flap 1600, it may cause the spring body 1410 to bend. The bending may primarily occur at the living hinges 1440, 1450, which may cause the spring body 1410 to travel according to the air applied. Once the air is no longer applied, the spring return aspects of the first and second separations 1420, 1430, described above, may cause the spring body 1410 to return to its original position. Depending on how the valve flap is positioned, it may alternate between closed and open, or open and closed positions.

In one example, the valve flap 1600 may be used with only one living hinge 1440. In such an example, the first end 1424 of the spring body 1410 may be affixed to the valve surface 1710, while the second end 1434, which would not have a living hinge 1450, would also be affixed to the valve surface 1710.

In one example, the valve flap 1600 may be utilized as a vibrating element rather than an air control element. For instance, with both ends 1424, 1434 anchored to a surface, the unanchored portion of the spring body 1410 may be able to travel when air is passed over or through it. The spring return may cause the spring body 1410 to return to its original position. If air is applied at a sufficient pressure and frequency, it may cause the valve flap 1600 to vibrate. This may have a number of applications, including in generating sound or tactile response. For instance, the valve flap 1600 may act as a reed in this configuration to generate tones at particular frequencies. In another example, the valve flap 1600 may create a buzzing sensation. Materials other than paper board may be useful in these configurations.

Figure 18:
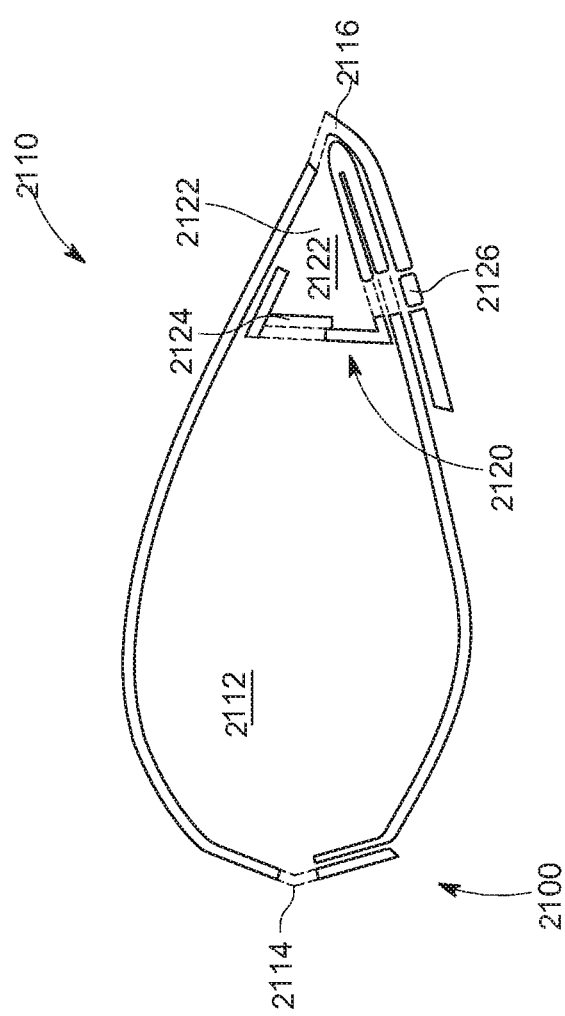
FIG. 18 is a longitudinal cross-sectional view of the apparatus in an expanded state, in accordance with a first exemplary embodiment of the present disclosure.

FIG. 18 is a longitudinal cross-sectional view of the apparatus 2100 in an expanded state, in accordance with a first exemplary embodiment of the present disclosure. The apparatus 2100 includes an outer housing 2110, movable between a collapsed state and an expanded state. The collapsed state has a substantially flat configuration. The expanded state encompasses a first volume 2112. The apparatus also includes an inner barrier 2120 positioned within the outer housing 2110, which, together with the outer housing 2110, delineates a second volume 2122. A first opening 2114 is formed at least partially within a sidewall of the outer housing 2110 at a first location, in fluid communication with the first volume 2112, and adapted to accommodate the mouthpiece of a metered dose inhaler 2277 (see FIG. 21). A second opening 2116 is formed within a sidewall of the outer housing 2110 at a second location in fluid communication with the second volume 2122, and is adapted to form an user mouth opening. A one-way inhalation valve 2124 is located on and formed integrally with the inner barrier 2120. Inhalation valve 2124 connects the first volume 2112 and the second volume 2122. A one-way exhalation valve 2126 is formed within a sidewall of the outer housing 2110 and the inner barrier 2120 at a third location, and is also formed integrally with the housing. Exhalation valve 2126 connects the second volume 2122 and the exterior of the outer housing 2110. When the apparatus 2100 is in an expanded state, gas is flowable from the metered dose inhaler to the first volume 2112, from the first volume 2112 to the second volume 2122, and from the second volume 2122 to the mouth of a user. In the expanded state, gas is also flowable from the mouth of a user to the second volume 2122 and to the exterior of the outer housing 2110.

Figure 19:
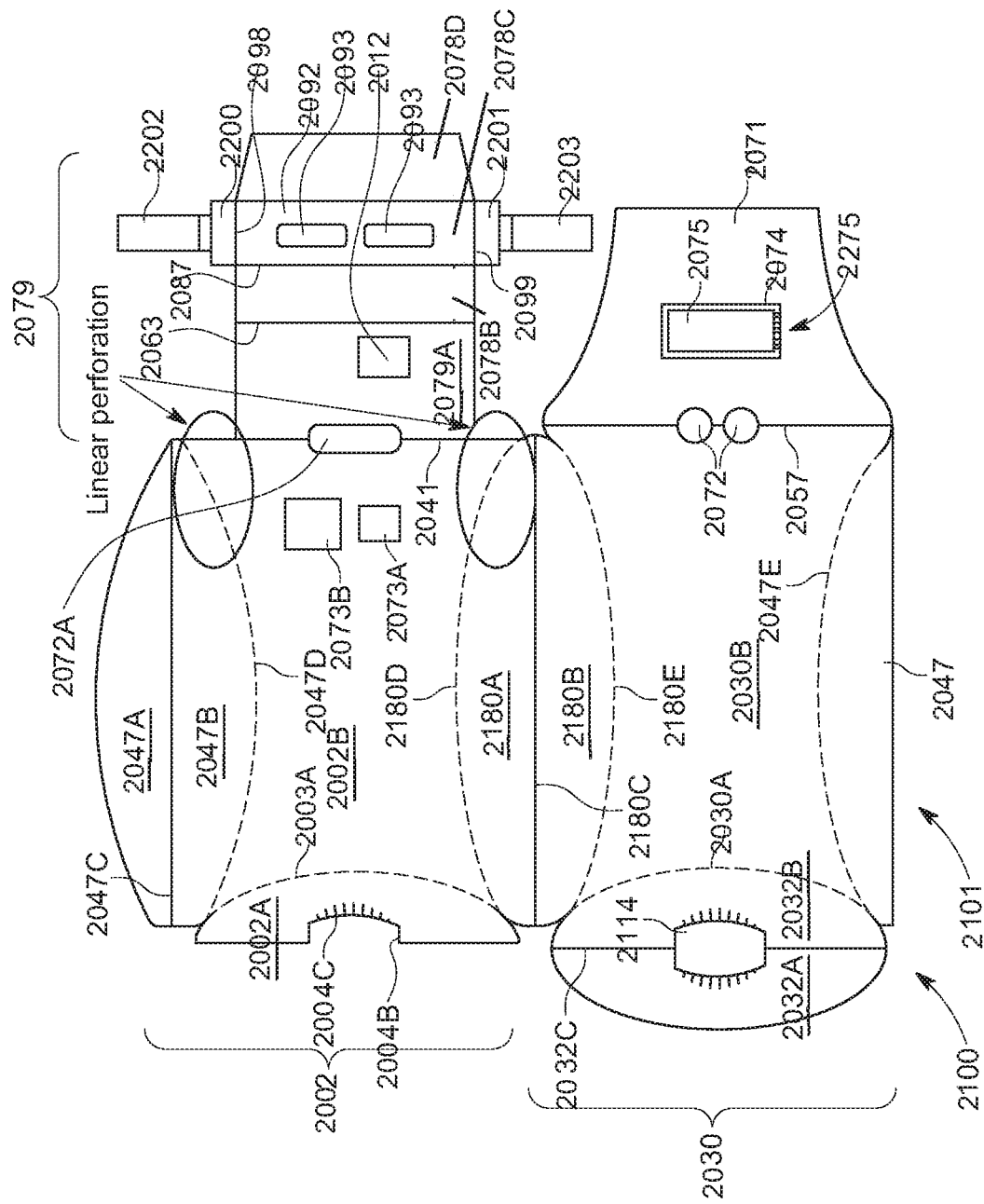
FIG. 19 is an interior plan view of a sheet from which the apparatus is constructed, in accordance with a first exemplary embodiment of the present disclosure.

FIG. 19 is a plan view of a blank or sheet 2101 from which the apparatus 2100 is constructed, in accordance with a first exemplary embodiment of the present disclosure. The sheet 2101, when expanded, takes the shape state shown in FIG. 19. FIG. 20 shows the interior side of the sheet 2101, i.e., the side that forms the interior of the apparatus 2100 as assembled. Sheet 2101 includes a bottom section 2002, a top section 2030, an inner barrier section 2079, and an outer user mouth opening section 2071. The inner barrier 2120 is formed from the panels in the inner barrier section 2079, while the outer housing 2110 is formed from the remaining portions of the sheet 2101. The bottom section 2002 and top section 2030 are connected by a side section, which includes two side panels 2180A and 2180B connected by a straight scored fold line 180C as shown. Side panel 2180A is connected along an arcuate "skip-scored" fold line 2180D to bottom panel 2002B, and side panel 2180B is connected along an arcuate skip-scored fold line 2180E to top panel 2030B. (A skip-scored fold line includes a sequence of scored and non-scored sections of a fold line having the appearance of dashed line).

On the top section 2030, adhesive attachment panel 2047 is connected by an arcuate scored fold line 2047E to top panel 2030B, and eventually is adhesively attached to the inner surface of left side panel 2047A on bottom section 2002, as will be described below. Side panel 2047A is connected to panel 2047B, which is connected to bottom panel 2002B by arcuate skip-scored fold line 2047D.

In one example, skip-scored fold lines 2047D, 2180D may only be partially arcuate. That is, the portion of the fold lines beginning near inhaler opening 2114 may be arcuate, but the portion of the fold lines near the openings 2072 may be substantially linear.

On the bottom section 2002, an end portion of bottom panel 2002B is connected along an arcuate skip-scored fold line 2003A to an inner boot adapter panel 2002A. Conversely, on the top section 2030, an outer boot adapter panel 2032A,B includes a panel 2032A which is connected along a straight scored fold line 2032C to an outer boot adapter panel 2032B, which is connected along arcuate skip-scored fold line 2030A to an end of top panel 2030B. A portion of an elongated inhaler opening 2114 bounded by scalloped sections 2004B, which are formed by slits 2004C, is aligned with a corresponding portion of half-opening 2004B in inner boot adapter panel 2002A.

User mouth opening section 2071 is connected along straight scored fold line 2057 to top panel 2030B. Circular mouth openings 2072 may be symmetrically formed in both top panel 2030B and user mouth opening section 2071, so as to be bisected by scored fold line 2057. However, user mouth openings 2072 need not be circular, but may be any suitable shape, such as square, rectangle, oval, and the like.

Also, user mouth openings 2072 may be located at any suitable point along top panel 2030B and user mouth opening section 2071. For instance, user mouth openings 2072 may be exclusively located on top panel 2030B or exclusively located on user mouth opening section 2071. Or, user mouth openings 2072 may be asymmetrically formed in both top panel 2030B and mouthpiece section 2071.

A rectangular exhalation valve flap 2075 is formed from user mouth opening section 2071. In one example, the exhalation valve flap 2075 may be cut into about the center of user mouth opening section 2071 on three sides, forming a gap 2074. On the remaining side, hinge 2275 may be cut. This is explained in greater detail with reference to FIG. 20A, below. The exhalation valve flap 2075 may be any size and shape suitable for use as an exhalation valve. The exhalation valve flap 2075 may be connected to the user mouth opening section 2071 by any suitable number and orientation of hinges cut into the sheet 2101.

In one example, exhalation valve opening 2073A is formed in bottom panel 2002B. When the apparatus 2100 is assembled, exhalation valve opening 2073A enables the second volume 2122 to be in fluid communication with the exterior of the apparatus 2100 when a user exhales. Hinge recess 2073B may be formed near to exhalation valve opening 2073A in bottom panel 2002B. When the apparatus 2100 is assembled, hinge recess 2073B enables the exhalation hinge 2275 to operate within the opening. This is discussed in greater detail with reference to FIG. 20B, below.

Inner barrier section 2079 includes a rectangular panel 2079A connected along straight scored fold line 2041 to bottom panel 2002B and a rectangular panel 2079B connected along a straight scored fold line 2063 to panel 2079A. An opening 2012 in panel 2079A is adapted to align with exhalation valve opening 2073A when panel 2079A is folded against the inner surface of bottom panel 2002B as shown in FIG. 18. When assembled, the portion of the apparatus 2100 wherein opening 2072A is located may be the opening side of the apparatus 2100.

In one example, an elongated rectangular opening 2072A is symmetrically formed in bottom panel 2002B and panel 2079A so as to be bisected by fold line 2041. Opening 2072A may be any suitable shape to work in conjunction with openings 2072. Opening 2072A may comprise one or more openings to work in conjunction with openings 2072. Opening 2072A may be located at any point on bottom panel 2002B or panel 2079A to work in conjunction with openings 2072. For instance, depending on the location of openings 2072, opening 2072A may be located entirely on bottom panel 2002B, entirely on panel 2079A, or asymmetrically formed within both bottom panel 2002B and panel 2079A. Panel 2079B is connected to another panel 2079C along a straight scored fold line 2087. Rectangular inhalation valve openings 2093 are formed in panel 2079C. Panel 2079C is attached to trapezoidal panel 2079D along a straight skip-scored fold line 2092. Preferably, inhalation valve openings 2093 are as large as can be practically fit into panel 2079C while nevertheless providing for proper operation of inhalation valve flaps 2202, 2203.

Side panels 2200 and 2201 are connected to panels 2079B and 2079C along straight, continuously-scored or perforated fold lines 2098 and 2099. The side panels 2200, 2201 fold around panel 2079C to bring inhalation valve flaps 2202, 2203 in line with inhalation valve openings 2093. When the apparatus is assembled, inhalation valve flaps 2202, 2203 cover inhalation valve opening 2093, allowing fluid communication between the first volume 2112 and the second volume 2122 when a user inhales. The inhalation valve mechanisms are discussed further in FIGS. 20A-B, below.

It should be noted that all openings may have any size, shape, orientation, number, and placement suitable to work in conjunction with each other and to facilitate use by a user. FIGS. 18 and 19 show exemplary openings generally located centrally on the apparatus 2100.

FIG. 20A is a close-up plan view of the sheet 2101 of FIG. 19, in accordance with a first exemplary embodiment of the present disclosure. FIG. 20A shows the portion of the sheet 2101 that, when assembled, forms the inner barrier 2120 of FIG. 18. Panels 2079A-D are shown connected by score lines, as discussed in FIG. 19. Connected to panel 2079C are side panels 2200 and 2201. In the example shown in FIG. 19, side panels 2200 and 2201 are the same design on opposite sides of side panel 2079C.

Side panel 2201 is shown within the close-up inset. Side panel 2201 comprises a generally rectangular panel connected to a rectangular inhalation valve flap 2203 by hinge 2205 cut into the panel 2201. Hinge 2205 comprises a series of skip scored through-cut lines in several rows. FIG. 20A shows 2003 rows of lines in a so-called running bond brick pattern. However, any number of rows or any suitable pattern may be used. The pattern cut into the panel 2201 allows the hinge portion of the panel 2201 to bend flexibly as necessary for operation of the apparatus 2100 while still maintaining structural integrity. Additionally, the hinge 2205 provides a limited spring action that returns the valve approximately to its neutral or starting position after use. Side panel 2200 is constructed the same as side panel 2201. Inhalation valve flap 2202 is connected to side panel 2200 by hinge 2204, which is shown as a running bond pattern, but may be any suitable pattern.

Skip scored lines 2047D and 2180 are shown as linear or straight, rather than arcuate lines in the visible portion of FIG. 20A. When the apparatus 2100 is assembled and expanded, the linear lines ensure that the bottom side of the apparatus 2100 remains flat, allowing the exhalation valve to remain in contact with the bottom side.

When assembled, the side panels 2079A, 2079B, 2079C, 2079D, 2200, 2201 fold inward to create an inner barrier 2120. Inhalation valve flaps 2202 and 2203 fold inward to cover inhalation valve openings 2093. When a user inhales, inhalation valve flaps 2202, 2203 bend inward to allow gas from the first volume 2112 to enter the second volume 2122. When a user is not inhaling, or when exhaling, inhalation valve flaps 2202, 2203 remain substantially sealed against panel 2079C to prevent fluid communication of the first volume 2112 and second volume 122 through inhalation valve openings 2093.

Figure 20B:
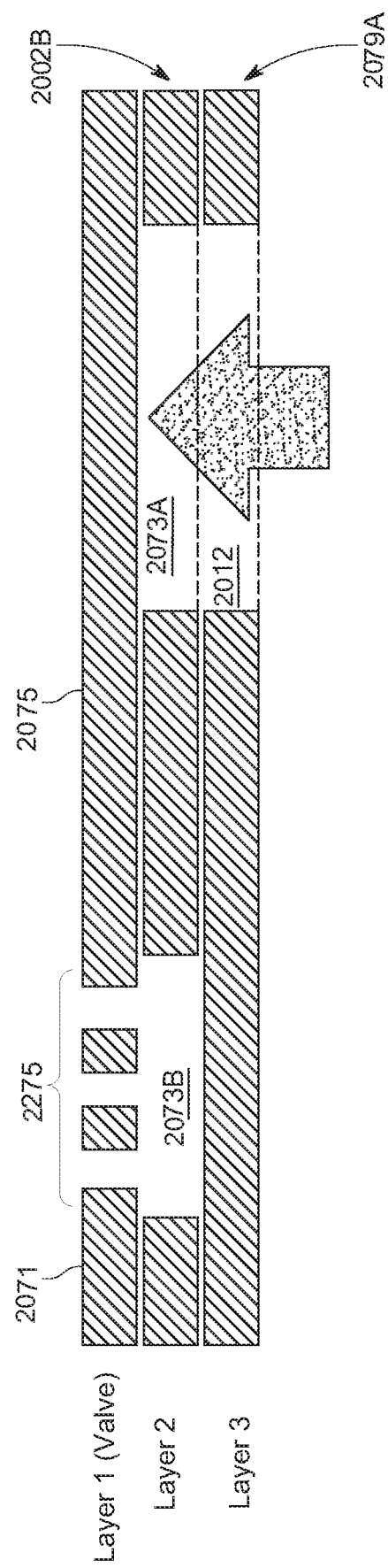
FIG. 20B is a cross-sectional view of a valve and hinge on the apparatus, in accordance with a first exemplary embodiment of the present disclosure.

FIG. 20B is a cross-sectional view of a valve and hinge on the apparatus, in accordance with a first exemplary embodiment of the present disclosure. As an example, FIG. 20B shows the exhalation valve mechanism having 2003 layers. The mechanism design may have any suitable number of layers and may be used in the inhalation valve mechanism as well. In the example shown in FIG. 20B, the outermost layer comprises outer mouth opening section 2071, connected to valve hinge 2275, which is connected to exhalation valve flap 2075. This outermost layer is folded against the exterior of bottom panel 2002B. While cutting the hinges for the valves, it is possible for excess sheet material to protrude from underneath the valves. In one example, a hinge recess 2073B may provide relief space for the hinge 2275 and any additional sheet material. This may allow the hinge 2275 to maintain the exhalation valve flap 2075 flat against the second layer 2002B. The third layer comprises panel 2079A, which is folded against bottom panel 2002B when forming the inner barrier 2120. Opening 2012 in panel 2079A aligns with exhalation valve opening 2073A to provide a channel for fluid communication from one side of the valve flap 2075 to the other.

Referring to FIGS. 18-20B, the apparatus 2100 may be constructed from the sheet 2101 as follows. Reference will be made to the "topside" and "underside" of the panels comprising sheet 2101, the "topside" being the portion of the panel or flap visible in FIGS. 19 and 20A, while the "underside" is the opposite side not visible in the drawings.

In one example, the apparatus 2100 is cut or punched from a single, unitary sheet 2101 of suitable material, such as solid bleached sulfate paperboard, plastic, spun nonwoven polymer such as TYVEK® by DuPont, or the like. The material may be an antistatic or static dissipative paper to reduce static deposition of medicine particles on the walls of the apparatus 2100. In one example, the sheet 2101 may be coated in a static dissipative coating or the like. Inhalation valves 2124 and exhalation valve 2126, including valve hinges 2204, 2205, 275 and valve flaps 2202, 2203, 2075, may be created from the unitary sheet 2101 by die cutting, punching, laser cutting, an X-Y table cutter, or a combination thereof. The apparatus 2100 may include multiple cutting steps, depending on the accuracy desired for each step. For instance, a steel rule die may not be able to accurately cut out the hinges, so a steel rule die may be used to cut out other portions of the apparatus 2100, while a laser cutter may be used for the finer cuts.

The inner barrier 2120 may be assembled next. The panels and flaps may be fixed or glued together using one or more suitable adhesives. The folding and gluing process starts by applying adhesive to the bottom side of side panels 2200, 2201. Side panels 2200, 2201 are folded over lines 2098, 2099, respectively, so that the adhesive sides contact the underside of panel 2079C. Adhesive is then applied to the topside of panel 2079A, which is folded over line 2041 so that the adhesive surface contacts the topside of bottom panel 2002B. Panel 2079B is folded outward along line 2063 so that the topside of panel 2079B is visible as in FIG. 19. Panel 2079C is then folded inward along line 2087 so that the topside of panel 2079C is not visible. Finally, panel 2079D is folded along line 2092 so that the topside of panel 2079D is visible. Top section 30 is folded over line 2180C so that the topside of top panel 30B is in contact with the topside of bottom panel 2002B. Adhesive is applied to panel 2079D, and it is glued to the topside of top panel 2030B.

The outer housing 2110 may be assembled next. Adhesive is applied to the topside of panel 2032A, which is folded over line 2032C and glued to the underside of panel 2002A. Adhesive is applied to the topside of panel 2047A, which is folded over line 2047C and glued to the underside of panel 2047. Adhesive is applied to the topside of outer mouth opening section 2071, which is folded over line 2057 and glued to the underside of bottom panel 2002B.

Figure 21:
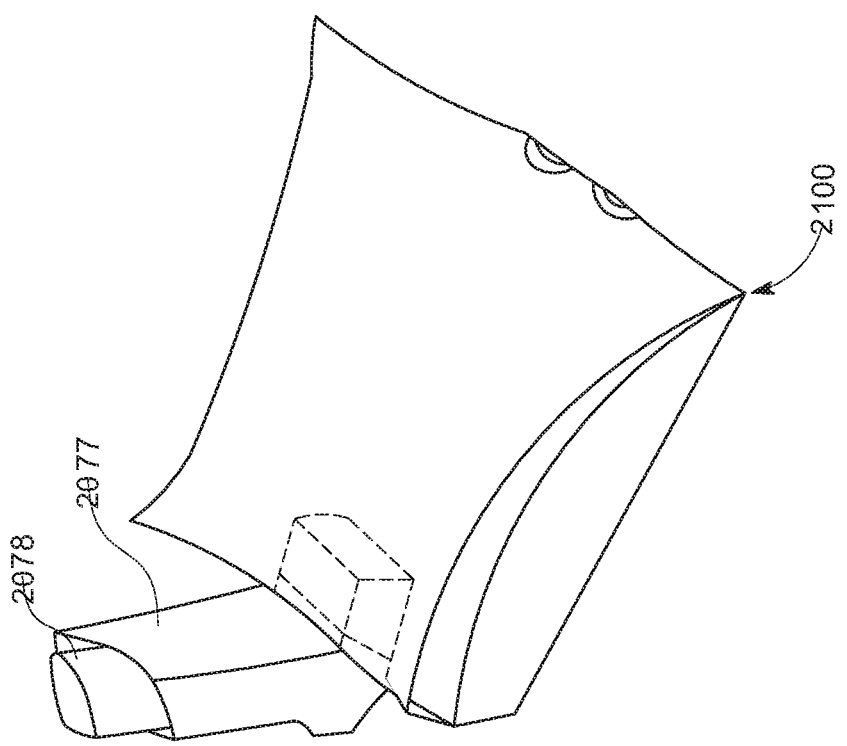
FIG. 21 is a perspective view of the apparatus in an expanded state, in accordance with a first exemplary embodiment of the present disclosure.

FIG. 21 is a perspective view of the apparatus 2100 in an expanded state, in accordance with a first exemplary embodiment of the present disclosure. In the expanded state, apparatus 100 is capable of receiving the mouthpiece end of the boot adapter 2077 of a conventional inhaler containing an MDI canister 2078 inserted through inhaler opening 2114 shown in FIG. 18.

Referring to FIGS. 18-21, the apparatus 2100 may be expanded as follows. When the apparatus 2100 is assembled as described above, it is in its flat or collapsed state. When an user presses right side panels 2180A and 2180B inward toward left side panels 2047A and 2047B so that they "unfold" along straight, scored fold lines 180C and 47C, respectively, the apparatus 2100 pops into and retains the configuration shown in FIG. 21. The fold lines 2063, 2087, and 2092 allow panels 2079B and 2079C to be pulled by adhesive and 2079D and the rising upper panel 30B upward from their generally horizontal position when apparatus 2100 is collapsed so that the panels 2079B,C are in a nearly vertical position when apparatus 2100 is fully "popped up". Furthermore, as side panels 2047A, 2047B, 2180A, 2180B are pressed inward along partially arcuate lines 2047D, 2180D, 247E, 2180E they come into contact with the sides of panels 2079B, 79C, creating delineation between the first volume 2112 and the second volume 2122 that limits airflow around the sides.

Additionally, when the boot adapter 2077 with an MDI canister 2078 therein is inserted into opening 2114, that causes boot adapter panels 2032A and 2032B to unfold to the maximum extent.

FIG. 22 is a plan view of a sheet 2499 from which the apparatus 2100 is constructed, in accordance with a second exemplary embodiment of the present disclosure. In one example, the design of the sheet 2499 may be substantially similar to sheet 2101 shown in FIG. 19, with the exception of the inhalation valve design. Instead of the inhalation valve openings 2093 located on panel 2079C, the inhalation valve flaps 2202, 2203 and valve hinges 2204, 2205 are located thereon. Side valve panels 2500, 2501 are connected to the sides of panel 2079C by lines 2098 and 99, respectively. Side valve panel 2500 comprises valve opening 2502, hinge recess 2504, and recess flap 2506. Side valve panel 2501 comprises valve opening 2503, hinge recess 2505, and recess flap 2507. When assembled, side valve panels 2500, 2501 may be folded so that the topside of side valve panels 2500, 2501 is in contact with the topside of panel 2079C, and the panels 2500, 2501, 2079C may be glued together. This causes valve openings 2502, 2503 to align with inhalation valve flaps 2202, 2203 which can open towards a user's mouth to allow gas to flow from the first volume 2112 to the second volume 2122. Recess flaps 2506, 2507 may be folded over lines 2592, 2593 so that the underside of the recess flaps 2506, 2507 is in contact with the underside of the side valve panels 2500, 2501, respectively. The recess flaps 506, 507 may be glued to the side valve panels 2500, 2501. This, along with hinge recesses 2504, 2505 creates a relief space for the valve hinges 2204, 2205 to operate, as discussed with respect to FIG. 20B, above.

It is noted that panel 2079A is shown as a trapezoid, which better conforms to the shape determined by the partially arcuate fold lines 2047A, 2047B, 2180A, 2180B when the apparatus 100 is expanded. Panel 2079A may be any suitable shape to achieve an airflow-limiting delineation between the first volume 2112 and the second volume 2122, and the trapezoidal shape is not limited to any particular embodiment.

FIG. 23 is a flowchart 2600 describing a method of expanding a medication inhalation apparatus from an initially flat, collapsed state, in accordance with a first embodiment of the present disclosure. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

In step 2610, an expandable apparatus 2100 as described above is provided in a collapsed state.

In step 2620, a pair of opposite sidewall panels on the outer housing is manually pressed toward one another, causing the outer housing and inner barrier to manually expand to create a first volume encompassed by the outer housing and a second volume delineated by the inner barrier and a mouth opening end of the outer housing (step 2630), wherein the inhaler opening is in fluid communication with the first volume, wherein the mouth opening is in fluid communication with the second volume, wherein the inhalation valve connects the first volume and the second volume, and wherein the exhalation valve connects the second volume and the exterior of the outer housing, whereupon gas is flowable from the metered dose inhaler to the first volume, from the first volume to the second volume, and from the second volume to the mouth of a user.

Operating Example

The following operating example may illustrate how the apparatus 2100 is used in implementation.

The apparatus 2100 may be assembled as described relative to FIGS. 19-20 and 22 above. The outer housing 2110 is expanded as described relative to FIG. 21. A user inserts the mouthpiece end of the boot adapter 2077 of an inhaler container an MDI canister 2078 through the inhaler opening 2114 of the apparatus 2100 until it fits snugly. The user then places his or her mouth on the mouth opening 2116, and exhales into the second volume 2122. The user's exhaled breath exits the second volume 2122 through the exhalation valve 2126. Increased pressure in the second volume 2122 causes valve flap 2075 to flex away from exhalation valve opening 2073A using valve hinge 2275, allowing the exhaled breath to escape the apparatus 2100. As the user finishes exhaling, the valve flap 2075 returns to its "closed" position on the apparatus 100, preventing air from entering the apparatus 2100. The user next engages the MDI canister 2078 to spray medicine into the first volume 2112 of the outer housing 2110. The medicine initially expands and fills the first volume 2112, as the user inhales through the apparatus 2100, causing the inhalation valve 2124 to open. Valve flaps 2202 and 2203 flex open into the second volume 2122 of the apparatus, allowing the medicine to travel from the first volume 112 to the second volume 2122. As the user continues to inhale, the medicine continues to travel from the second volume 2122 into the user's mouth through the mouth opening 2116. After the user has finished inhaling, the valve flaps 2202, 2203 returns to their "closed" position on the inner barrier 2120, preventing air from the outer housing 2110 from entering the second volume 2122.

In some cases, an user may perform some of the steps in a different order. For instance, the user may engage the MDI canister 2078 to spray before exhaling, or the user may wait some time between engaging the MDI canister 2078 and inhaling. The apparatus 2100 is designed to deliver an effective dose even under these conditions.

Test Examples

The following test example may illustrate the effectiveness of the apparatus 2100 in creating a medication inhalation apparatus with improved medication delivery.

In evaluating the efficacy of the apparatus of the present invention, two iterations of the apparatus 2100 were evaluated against the currently available Thayer Medical LiteAire®, a pop-up, disposable MDI holding chamber as described in U.S. Pat. No. 6,550,473 which had previously improved medication delivery efficacy over the prior art. One difference between the current LiteAire® device and the subject apparatus 2100 is that the current LiteAire® device uses bendable membranes glued to the sheet 2101 as inhalation and exhalation valves. Therefore, the test will show any differences in efficacy between the unitary valve design and the membrane design. For this experiment, the apparatus 2100 was made from 2016 point SBS paperboard as described above. A Trudell Fast-Screening Andersen Cascade Impactor (T-FSA) was used to measure total emitted dose (TED), coarse particle dose (CPD) and fine particle dose (FPD) delivered by both devices. The particle size distributions of the two devices were compared with both coordinated and uncoordinated breathing as well as constant inhalation. Coordinated breathing is defined as actuation of the MDI occurring during the onset of user inhalation. Uncoordinated breathing is defined as actuation of the MDI occurring during the onset of user exhalation. Constant inhalation is where the machine is simply run continuously. A good metric of the efficacy of the apparatus 2100 to mitigate user incoordination is the amount of dose lost from the coordinated breathing test to the uncoordinated breathing test.

The subject apparatus 2100 performed statistically better than the current LiteAire® device in total emitted dose for constant inhalation and coordinated breathing, as well as fine particle dose for constant inhalation. For coarse particle dose, coarse particle fraction, and fine particle fraction, the results were not statistically different on any of the breathing simulations, and the subject apparatus 2100 did not perform statistically worse than the current LiteAire® device for any attribute.

These data seem to indicate that the subject apparatus 2100 as a whole performs comparably to the current LiteAire® device, and yet is simpler, has the capability to incorporate alternative sheet material that allow it or be less costly to manufacture, or less costly to dispose or potentially more durable. It should be noted that the design for the subject apparatus 2100 also differs from the current LiteAire® device in the placement of the inner barrier 2120, which is placed nearer to the mouthpiece end of the outer housing 2110. In order to isolate the inner barrier 2120 as the cause for this improvement, a modified version of the current LiteAire® was created that placed the inner barrier the same distance away from the mouth opening as in the subject apparatus 2100. The tests were again run. The modified LiteAire® device performed slightly better than the subject apparatus 2100, indicating that the placement of the inner barrier 2120 has a positive effect on overall device efficacy.

However, the tests confirm that the subject apparatus 2100 on the whole performs comparably to the current LiteAire® device, despite the subject apparatus 2100 being made from a single, unitary sheet, including the valves. Thus, the valve design is robust enough to perform comparably to the current LiteAire® and while offering a range of other desirable characteristics.

Thus, the invention provides a disposable "pop up", valved apparatus 2100 which also allows for natural inhalation and exhalation by a user. The described valved apparatus 2100 can be maintained in a collapsed, flat configuration, suitable for storage in a suit coat pocket or a briefcase, and expanded immediately prior to use, after which it can be discarded or collapsed for later use by the same user. The described apparatus 2100 may be used by health care workers to demonstrate its use to users needing to receive an aerosol medication from an MDI inhaler. The apparatus 100 also is well suited for use in hospital emergency rooms, health-care clinics, pulmonary function labs, or infirmaries. In addition, its portability and low cost make it ideal for use by relief or world health organizations, especially when aerosol vaccines become available.

While the invention has been described with reference to several particular embodiments thereof, those skilled in the art will be able to make the various modifications to the described embodiments of the invention without departing from the true spirit and scope of the invention. It should be emphasized that the above-described embodiments of the present disclosure, particularly, any "preferred" embodiments, are merely possible examples of implementations, merely set forth for a clear understanding of the principles of the disclosure. It is intended that all elements or steps which are insubstantially different or perform substantially the same function in substantially the same way to achieve the same result as what is claimed are within the scope of the invention. For example, an exhalation valve or other port may be provided on any portion of the inner housing/outer housing. Various other ways of folding the sheet material to achieve the collapsed/expanded configurations can be provided. Different arrangements of lock tabs and lock tab receiving slots than disclosed herein could be provided, or Velcro or similar attachment materials could be used. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A medication inhalation apparatus, comprising:
   an outer housing, collapsible into a substantially flat configuration and expandable to define a first volume adapted to receive a plume of medication particles ejected by an MDI inhaler;
   a fully contained inner housing also collapsible into a substantially flat configuration, located within the outer housing and expandable to define a second volume within the outer housing;
   a first opening formed through a first wall of the outer housing at a first location, in fluid communication with the first volume, and adapted to accommodate a mouthpiece of the MIDI inhaler;
   a second and a third opening formed either through a second wall of the outer housing and the inner housing, or through a third wall of the inner housing alone, adapted to form an user mouth opening in fluid communication with the second volume; or a second opening formed through a second wall of the outer housing at a second location adapted to form a user mouth opening in fluid communication with the second volume;
   a one-way inhalation valve located within the second or third wall of the inner housing, the inhalation valve connecting the first volume and the second volume, wherein the inhalation valve comprises a valve flap with spring return, said valve flap comprising:
   a spring body formed of a paperboard material with a strength and rigidity providing limited flexibility, the spring body having an elongate axis;
   a first separation perpendicular to the elongate axis of the spring body, the first separation extending from a first edge of the spring body across at least a portion of a width of the spring body;

a second separation perpendicular to the elongate axis of the spring body, the second separation extending from a second edge of the spring body across at least a portion of the width of the spring body;

a living hinge formed in the spring body and located a spaced distance from the first and second separations; and an uncut section located in the spaced distance between the living hinge and the first and second separations, the uncut section positionable to prevent the flow of gas through a valve opening; and a one-way exhalation valve located within the second wall of the outer housing or within the outer housing and the inner housing, the exhalation valve connecting the second volume and an exterior of the outer housing, or connecting the second volume and an exterior of the outer housing;

wherein, in an expanded state, gas is flowable from a connected MDI inhaler to the first volume, from the first volume to the second volume, and from the second volume to the mouth of a user.

2. The apparatus of claim 1, characterized by one or more of the following features:
   (a) wherein the outer housing and the inner housing are constructed from a single piece of paperboard stock;
   (b) wherein the inner housing is connected to the outer housing at a fold;
   (c) wherein the outer housing and the inner housing are constructed from a single piece of paperboard sheet stock, and wherein the outer housing and the inner housing are formed by folding the sheet, and wherein the outer housing is connected to the inner housing adjacent the mouth opening side of the sheet stock;
   (d) wherein the outer housing and the inner housing are at least partially constructed from antistatic paperboard stock material;
   (e) wherein the inner housing has a polyhedron shape, when flattened having at least five sides, and wherein at least four of the at least five sides abut an interior of the outer housing;
   (f) wherein the inner housing comprises at least two integral side panels;
   (g) wherein the inner housing is formed in part from folded, webbed panels;
   (h) wherein the inhalation valve and exhalation valve are collapsible to a substantially flat configuration; and
   (i) Wherein the inhalation valve and exhalation valve are operable by a user's inhaling and exhaling.

3. The apparatus of claim 1, characterized by one or more of the following features:
   (a) wherein the outer housing and the inner flap are constructed from a single piece of paperboard stock;
   (b) wherein the inner flap is connected to the outer housing at a fold;
   (c) wherein the open housing and the inner flap are constructed from a single piece of paperboard sheet stock, and wherein the outer housing and the inner flap are formed by folding the paperboard sheet stock, and wherein the outer housing is connected to the inner flap adjacent the mouth opening side of the paperboard sheet stock;
   (d) wherein at least two corners on a bottom panel of the outer housing are receded corners;
   (e) wherein the outer housing and the inner housing are at least partially constructed from antistatic paperboard sheet material;
   (f) wherein the inner flap comprises a plurality of panels having a plurality of tension relief lines;
   (g) wherein the inner flap is adhesively attached to a bottom panel of the outer housing along at least three adhesive lines arranged in an "H" pattern;
   (h) wherein the inner flap comprises an adhesive panel adjacent to a top panel of the outer housing, and wherein the adhesive panel is adhesively attached to the top panel of the outer housing, and wherein the adhesive panel extends substantially across a width of the inner flap.

4. A method of expanding the medication inhalation apparatus of claim 1 from an initially flat, collapsed state, to an expanded state comprising the steps of:
   manually pressing a pair of opposite sidewall panels on the outer housing towards one another, whereby to force the opposite sidewall panels into positions approximately perpendicular to a top and bottom panel of the outer housing; and
   inserting the mouthpiece of the MDI inhaler into the mouth opening in the outer housing.

5. The apparatus of claim 1, characterized by one or more of the following features:
   (a) wherein the living hinge comprises a plurality of central separations disposed between a plurality of edge separations, wherein the central separations extend perpendicular to the elongate axis of the spring body across a center of the width of the spring body, and wherein the edge separations extend perpendicular to the elongate axis of the spring body from the first and second edges of the spring body;
   (b) wherein the first and second separations extend across a substantial portion of the width of the spring body;
   (c) wherein the spring body is formed from first and second adjacent layers fixed together along a plane, wherein the second layer comprises at least one cutout adjacent to the spring;
   (d) wherein the first and second separations are spaced apart by a spaced distance, wherein the spaced distance between the first and second separations is substantially less than a length of the first and second separations; and
   (e) further comprising:
      a second living hinge formed in the spring body and located a spaced distance from the first and second separations opposite the first living hinge; and
      a second uncut section located in the spaced distance between the second living hinge and the first and second separations, the second uncut section positionable to prevent the flow of gas through a valve Opening, wherein an end of the spring body near the first living hinge and an end of the spring body near the second living hinge are affixed to a valve surface.

6. A medication inhalation apparatus, comprising:
   an outer housing, collapsible into a substantially flat configuration and expandable to define a first volume adapted to receive a plume of medication particles ejected by an MDI inhaler;
   an inner flap located within the outer housing and expandable to define a second volume within the outer housing, wherein an edge panel of the inner flap is affixed to a portion of the outer housing to secure the second volume;
   a first opening formed through a wall of the outer housing at a first location, in fluid communication with the first volume, and adapted to accommodate a mouthpiece of the MDI inhaler;

a second opening formed through a wall of an outer panel of the inner flap, and adapted to form a user mouth opening in fluid communication with the second volume;

a one-way inhalation valve located within a central panel of the inner flap, the inhalation valve connecting the first volume and the second volume, wherein the inhalation valve comprises a valve flap with spring return, said valve flap comprising:

a spring body formed of a paperboard material with a strength and rigidity providing limited flexibility, the spring body having an elongate axis;

a first separation perpendicular to the elongate axis of the spring body, the first separation extending from a first edge of the spring body across at least a portion of a width of the spring body;

a second separation perpendicular to the elongate axis of the spring body, the second separation extending from a second edge of the spring body across at least a portion of the width of the spring body;

a living hinge formed in the spring body and located a spaced distance from the first and second separations; and an uncut section located in the spaced distance between the living hinge and the first and second separations, the uncut section positionable to prevent the flow of gas through a valve opening; and a one-way exhalation valve located within an outer panel of the inner flap in a second location and the wall of the outer housing, the exhalation valve connecting the second volume and an exterior of the outer housing, wherein, in an expanded state, gas is flowable from a connected MDI inhale to the first volume, from the first volume to the second volume, and from the second volume to the mouth of a user.

7. The apparatus of claim 6, characterized by one or more of the following features:

(a) wherein the outer housing and the inner flap are constructed from a single piece of paperboard stock, wherein the inner flap preferably is connected to the outer housing at a fold;

(b) wherein the outer housing and the inner flaps are constructed from a single piece of paperboard sheet stock, and wherein the outer housing and the inner flap are formed by folding the paperboard sheet stock, and wherein the outer housing is connected to the inner flap adjacent the mouth opening side of the paperboard sheet stock;

(c) wherein the outer housing and inner flap are constructed from a single piece of paperboard stock, and wherein at least two corners on a bottom panel of the outer housing are receded corners;

(d) wherein the outer housing and the inner housing are at least partially constructed from antistatic material; and (e) wherein the one-way exhalation valve comprises an exhalation valve located within the inner flap and a valve opening located within a wall of the outer housing.

8. A method of expanding a medication inhalation apparatus from an initially flat, collapsed state, to an expanded state comprising the steps of: providing in, a collapsed state, the medication inhalation apparatus, comprising:

an outer housing, collapsible into a substantially flat configuration and expandable to define a first volume adapted to receive a plume of medication particles ejected by an MDI inhaler;

a fully contained inner housing also collapsible into a substantially flat configuration, located within the outer housing and expandable to define a second volume within the outer housing;

a first opening formed through a first wall of the outer housing at a first location, in fluid communication with the first volume, and adapted to accommodate a mouthpiece of the MDI inhaler, a second and a third opening formed either through a second wall of the outer housing and the inner housing, or through a third wall of the inner housing alone, adapted to form an user mouth opening in fluid communication with the second volume; or a second opening formed through a second wall of the outer housing at a second location adapted to form a user mouth opening in fluid communication with the second volume;

a one-way inhalation valve located within the second or third wall of the inner housing, the inhalation valve connecting the first volume and the second volume, wherein the inhalation valve comprises a valve flap with spring return, said valve flap comprising:

a spring body formed of a paperboard material with a strength and rigidity providing limited flexibility, the spring body having an elongate axis;

a first separation perpendicular to the elongate axis of the spring body, the first separation extending from a first edge of the spring body across at least a portion of a width of the spring body;

a second separation perpendicular to the elongate axis of the spring body, the second separation extending from a second edge of the spring body across at least a portion of the width of the spring body;

a living hinge formed in the spring body and located a spaced distance from the first and second separations; and an uncut section located in the spaced distance between the living hinge and the first and second separations, the uncut section positionable to prevent the flow of gas through a valve opening; and a one-way exhalation valve located within the second wall of the outer housing or within the outer housing and the inner housing, the exhalation valve connecting the inner volume and the exterior of the outer housing, or connecting the second volume and an exterior of the outer housing;

manually pressing a pair of opposite sidewall panels on the outer housing towards one another, whereby to force the opposite sidewall panels into positions approximately perpendicular to a top and bottom panel of the outer housing; and inserting a mouthpiece of an MDI inhaler into an inhaler opening in the outer housing.

9. A method of expanding a medication inhalation apparatus from an initially flat, collapsed state, to an expanded state comprising the steps of:

providing, in the collapsed state, the medication inhalation apparatus having an outer housing, an inner flap located within the outer housing, wherein the outer housing and the inner flap are substantially airtight when expanded, an inhaler opening formed at least partially within a first sidewall of the outer housing at a first location, a mouth opening positioned within a second sidewall of the outer housing at a second location, a one-way inhalation valve positioned within a sidewall of the inner flap, and a one-way exhalation valve positioned within the second sidewall of the outer housing at a third location;
pressing a pair of opposite sidewall panels on the outer housing; and
manually expanding the outer housing and inner flap to create a first volume encompassed by the outer housing and a second volume encompassed by the inner flap and the outer housing, wherein the inhaler opening is in fluid communication with the first volume, wherein the mouth opening is in fluid communication with the second volume, wherein the inhalation valve connects the first volume and the second volume, wherein the exhalation valve connects the second volume and the exterior of the outer housing, and wherein gas is flowable from the inhaler to the first volume, from the first volume to the second volume, and from the second volume to the mouth of a patient.

10. A medication inhalation apparatus comprising:
an outer housing formed of paperboard, movable between a collapsed state and an expanded state, wherein the collapsed state has a substantially flat configuration, and wherein the expanded state encompasses a first volume;
an inner barrier formed of paperboard positioned within the outer housing and, together with a mouth opening end of the outer housing, delineating a second volume;
an inhaler opening formed at least partially within a wall of the outer housing at a first location, the inhaler opening in fluid communication with the first volume, wherein a mouth opening of a metered dose inhaler is insertable therein;
the mouth opening positioned within the second wall of the outer housing at a second location, the mouth opening in fluid communication with the second volume;
a one-way inhalation valve positioned within a wall of the inner barrier and connecting the first volume and the second volume, wherein the inhalation valve is formed from the inner barrier and comprises a valve flap with spring return, said valve flap comprising:
a spring body formed of a paperboard material with a strength and rigidity providing limited flexibility, the spring body having an elongate axis;
a first separation perpendicular to the elongate axis of the spring body, the first separation extending from a first edge of the spring body across at least a portion of a width of the spring body;
a second separation perpendicular to the elongate axis of the spring body, the second separation extending from a second edge of the spring body across at least a portion of the width of the spring body;
a living hinge formed in the spring body and located a spaced distance from the first and second separations; and
an uncut section located in the spaced distance between the living hinge and the first and second separations, the uncut section positionable to prevent the flow of gas through a valve opening; and
a one-way exhalation valve positioned within the second wall of the outer housing and the inner barrier at a third location, the exhalation valve connecting the second volume and the exterior of the outer housing, wherein the exhalation valve is formed from the outer housing,
wherein, in an expanded state, gas is flowable from the metered dose inhaler to the first volume, from the first volume to the second volume, and from the second volume to the mouth of a user,
wherein the apparatus is formed from a single, unitary sheet of stock.

11. The apparatus of claim 10, characterized by one or more of the following features:
(a) wherein the apparatus is constructed from a single, unitary sheet of paperboard;
(b) wherein the outer housing and the inner barrier are formed by punching or cutting and folding a sheet of paperboard;
(c) wherein the apparatus is at least partially constructed from antistatic sheet stock;
(d) wherein the inhalation valve and exhalation valve are collapsible to a substantially, flat configuration;
(e) wherein the inhalation valve comprises at least one flap connected to the inner barrier by at least a first hinge, and wherein the exhalation valve comprises at least one flap connected to the outer housing by at least a second hinge, and wherein the at least first and second hinges sit over at least first and second hinge recesses, respectively;
(f) wherein the inhalation valve and exhalation valve are operable by a user's inhaling and exhaling; and
(g) wherein a bottom side of the mouth opening end of the outer housing is substantially flat, and further comprising at least two scored or perforated fold lines along the bottom side of the mouth opening end, wherein the at least two scored fold lines are substantially linear at the mouth opening end of the outer housing and arcuate thereafter.

12. A medication inhalation apparatus, comprising:
an outer housing, collapsible into a substantially flat configuration and expandable to define a first volume adapted to receive a plume of medication particles ejected by an MDI inhaler;
an inner flap located within the outer housing and, together with the outer housing, expandable to define a second volume within the outer housing, wherein the inner flap includes panels connected to one another along straight scored fold lines;
a first opening formed through a first wall of the outer housing at a first location, in fluid communication with the first volume, and adapted to accommodate a mouthpiece of the MDI inhaler;
a second opening formed through the second wall of the outer housing at a second location adapted to form a user mouth opening in fluid communication with the second volume;
a one-way inhalation valve located within the inner flap, the inhalation valve connecting the first volume and the second volume, wherein the inhalation valve comprises a valve flap with spring return, said valve flap comprising:
a spring body formed of a paperboard material with a strength and rigidity providing limited flexibility, the spring body having an elongate axis;
a first separation perpendicular to the elongate axis of the spring body, the first separation extending from a first edge of the spring body across at least a portion of a width of the spring body;
a second separation perpendicular to the elongate axis of the spring body, the second separation extending from a second edge of the spring body across at least a portion of the width of the spring body;
a living hinge formed in the spring body and located a spaced distance from the first and second separations; and an uncut section located in the spaced distance between the living hinge and the first and second separations, the uncut section positionable to prevent the flow of gas through a valve opening; and a one-way exhalation valve located within the second wall of the outer housing or within the outer housing and the inner housing, the exhalation valve connecting the second volume and an exterior of the outer housing, or connecting the second volume and an exterior of the outer housing;

wherein, in an expanded state, gas is flowable from a connected MDI inhaler to the first volume, from the first volume to the second volume, and from the second volume to the mouth of a user.

13. The apparatus of claim 12, characterized by one or more of the following features:
    (a) wherein the outer housing and the inner housing are constructed from a single piece of paperboard stock;
    (b) wherein the inner housing is connected to the outer housing at a fold;
    (c) wherein the outer housing and the inner housing are constructed from a single piece of paperboard sheet stock, and wherein the outer housing and the inner housing are formed by folding the sheet, and wherein the outer housing is connected to the inner housing adjacent the mouth opening side of the sheet stock;
    (d) wherein the outer housing and the inner housing are at least partially constructed from antistatic paperboard stock material;
    (e) wherein the inner housing has a polyhedron shape, when flattened having at least five sides, and wherein at least four of the at least five sides abut an interior of the outer housing;
    (f) wherein the inner housing comprises at least two integral side panels;
    (g) wherein the inner housing is formed in part from folded, webbed panels;
    (h) wherein the inhalation valve and exhalation valve are collapsible to a substantially flat configuration; and
    (i) wherein the inhalation valve and exhalation valve are operable by a user's inhaling and exhaling.

14. The apparatus of claim 12, characterized by one or more of the following features:
    (a) wherein the outer housing and the inner flap are constructed from a single piece of paperboard stock;
    (b) wherein the inner flap is connected to the outer housing at a fold;
    (c) wherein the open housing and the inner flap are constructed from a single piece of paperboard sheet stock, and wherein the outer housing and the inner flap are formed by folding the paperboard sheet stock, and wherein the outer housing is connected to the inner flap adjacent the mouth opening side of the paperboard sheet stock;
    (d) wherein at least two corners on a bottom panel of the outer housing are receded corners;
    (e) wherein the outer housing and the inner housing are at least partially constructed from antistatic paperboard sheet material;
    (f) wherein the inner flap comprises a plurality of panels having a plurality of tension relief lines;
    (g) wherein the inner flap is adhesively attached to a bottom panel of the outer housing along at least three adhesive lines arranged in an "H" pattern;
    (h) wherein the inner flap comprises an adhesive panel adjacent to a top panel of the outer housing, and wherein the adhesive panel is adhesively attached to the top panel of the outer housing, and wherein the adhesive panel extends substantially across a width of the inner flap.

15. A method of expanding the medication inhalation apparatus of claim 12 from an initially flat, collapsed state, to an expanded state comprising the steps of:
    manually pressing a pair of opposite sidewall panels on the outer housing towards one another, whereby to force the opposite sidewall panels into positions approximately perpendicular to a top and bottom panel of the outer housing; and
    inserting the mouthpiece of the MDI inhaler into the mouth opening in the outer housing.

16. The apparatus of claim 12, characterized by one or more of the following features:
    (a) wherein the living hinge comprises a plurality of central separations disposed between a plurality of edge separations, wherein the central separations extend perpendicular to the elongate axis of the spring body across a center of the width of the spring body, and wherein the edge separations extend perpendicular to the elongate axis of the spring body from the first and second edges of the spring body;
    (b) wherein the first and second separations extend across a substantial portion of the width of the spring body;
    (c) wherein the spring body is formed from first and second adjacent layers fixed together along a plane, wherein the second layer comprises at least one cutout adjacent to the spring;
    (d) wherein the first and second separations are spaced apart by a spaced distance, wherein the spaced distance between the first and second separations is substantially less than a length of the first and second separations; and
    (e) further comprising:
        a second living hinge formed in the spring body and located a spaced distance from the first and second separations opposite the first living hinge; and
        a second uncut section located in the spaced distance between the second living hinge and the first and second separations, the second uncut section positionable to prevent the flow of gas through a valve opening, Wherein an end of the spring body near the first living hinge and an end of the spring body near the second living hinge are affixed to a valve surface.

17. A method of expanding a medication inhalation apparatus from an initially flat, collapsed state, to an expanded state comprising the steps of:
    providing, in the collapsed state, the medication inhalation apparatus, comprising:
    an outer housing, collapsible into a substantially flat configuration and expandable to define a first volume adapted to receive a plume of medication particles ejected by an MDI inhaler;
    an inner flap located within the outer housing and, together with the outer housing, expandable to define a second volume within the outer housing, wherein the inner flap includes panels connected to one another along straight scored fold lines;
    a first opening formed through a first wall of the outer housing at a first location, in fluid communication with the first volume, and adapted to accommodate a mouthpiece of the MDI inhaler;
    a second opening formed through the second wall of the outer housing at a second location adapted to form a user mouth opening in fluid communication with the second volume;

a one-way inhalation valve located within the inner flap, the inhalation valve connecting the first volume and the second volume, wherein the inhalation valve comprises a valve flap with spring return, said valve flap comprising:
a spring body formed of a paperboard material with a strength and rigidity providing limited flexibility, the spring body having an elongate axis;
a first separation perpendicular to the elongate axis of the spring body, the first separation extending from a first edge of the spring body across at least a portion of a width of the spring body;
a second separation perpendicular to the elongate axis of the spring body, the second separation extending from a second edge of the spring body across at least a portion of the width of the spring body;
a living hinge formed in the spring body and located a spaced distance from the first and second separations; and
an uncut section located in the spaced distance between the living hinge and the first and second separations, the uncut section positionable to prevent the flow of gas through a valve opening; and
a one-way exhalation valve located within the second wall of the outer housing or within the outer housing and the inner housing, the exhalation valve connecting the inner volume and the exterior of the outer housing, or connecting the second volume and an exterior of the outer housing;
manually pressing a pair of opposite sidewall panels on the outer housing towards one another, whereby to force the opposite sidewall panels into positions approximately perpendicular to a top and bottom panel of the outer housing; and
inserting the mouthpiece of the MDI inhaler into the inhaler opening in the outer housing.

* * * * *